(12) United States Patent
Chen-Kiang et al.

(10) Patent No.: US 9,259,399 B2
(45) Date of Patent: Feb. 16, 2016

(54) TARGETING CDK4 AND CDK6 IN CANCER THERAPY

(75) Inventors: Selina Chen-Kiang, New York, NY (US); Maurizio Di Liberto, Rivervale, NJ (US); Xiangao Huang, New York, NY (US)

(73) Assignee: Cornell University, Ithaca, NY (US)

( * ) Notice: Subject to any disclaimer, the term of this patent is extended or adjusted under 35 U.S.C. 154(b) by 963 days.

(21) Appl. No.: 12/741,884

(22) PCT Filed: Oct. 1, 2008

(86) PCT No.: PCT/US2008/011331
§ 371 (c)(1),
(2), (4) Date: Sep. 17, 2010

(87) PCT Pub. No.: WO2009/061345
PCT Pub. Date: May 14, 2009

(65) Prior Publication Data
US 2011/0009353 A1 Jan. 13, 2011

Related U.S. Application Data

(60) Provisional application No. 60/986,176, filed on Nov. 7, 2007.

(51) Int. Cl.
| | |
|---|---|
| *A01N 43/54* | (2006.01) |
| *A61K 31/505* | (2006.01) |
| *A01N 43/40* | (2006.01) |
| *A61K 31/445* | (2006.01) |
| *A61K 31/00* | (2006.01) |
| *A61K 31/4025* | (2006.01) |
| *A61K 31/416* | (2006.01) |
| *A61K 31/4439* | (2006.01) |
| *A61K 31/506* | (2006.01) |
| *A61K 31/519* | (2006.01) |
| *G01N 33/50* | (2006.01) |

(52) U.S. Cl.
CPC ............. *A61K 31/00* (2013.01); *A61K 31/4025* (2013.01); *A61K 31/416* (2013.01); *A61K 31/445* (2013.01); *A61K 31/4439* (2013.01); *A61K 31/506* (2013.01); *A61K 31/519* (2013.01); *G01N 33/5011* (2013.01); *G01N 33/5044* (2013.01)

(58) Field of Classification Search
USPC .................................................. 514/272, 275
See application file for complete search history.

(56) References Cited

U.S. PATENT DOCUMENTS

| | | | |
|---|---|---|---|
| 6,608,053 B2 | 8/2003 | Hayakawa et al. |
| 2005/0059670 A1 | 3/2005 | Beylin et al. |
| 2006/0004000 A1 | 1/2006 | D'Orchymont et al. |
| 2014/0017265 A1 | 1/2014 | Yurkovetskiy et al. |
| 2014/0271460 A1 | 9/2014 | Sharpless et al. |
| 2014/0271466 A1 | 9/2014 | Sharpless et al. |
| 2014/0288116 A1 | 9/2014 | Bandla et al. |
| 2015/0030583 A1 | 1/2015 | Moore et al. |
| 2015/0125474 A1 | 5/2015 | Smith et al. |
| 2015/0140036 A1 | 5/2015 | Mannick et al. |
| 2015/0148345 A1 | 5/2015 | Lannutti et al. |

FOREIGN PATENT DOCUMENTS

| | | | |
|---|---|---|---|
| WO | WO-2005/094830 A1 | 10/2005 |
| WO | WO-2009061345 A2 | 5/2009 |
| WO | WO-2009061345 A2 | 12/2009 |
| WO | WO 2010/065824 A2 | 6/2010 |
| WO | WO-2011/068560 A1 | 6/2011 |
| WO | WO-2012/078492 A1 | 6/2012 |
| WO | WO-2012/125510 A1 | 9/2012 |
| WO | WO-2014/089241 A2 | 6/2014 |
| WO | WO-2014/100767 A1 | 6/2014 |
| WO | WO-2014/177915 A1 | 11/2014 |
| WO | WO-2014/205136 A1 | 12/2014 |
| WO | WO-2014/205138 A1 | 12/2014 |
| WO | WO-2015/073644 A1 | 5/2015 |
| WO | WO-2015/081127 A2 | 6/2015 |
| WO | WO-2015/084892 A1 | 6/2015 |

OTHER PUBLICATIONS

Shah et al. (Cyclin-dependent kinases as targets for cancer therapy, Cancer Chemother Biol Response Modif. 2003;21:145-70).*
"Pfizer Announces PALOMA-3 Trial for IBRANCE® (Palbociclib) Stopped Early Due to Efficacy Seen in Patients With HR+, HER2- Metastatic Breast Cancer Whose Disease Has Progressed Following Endocrine Therapy", Pfizer Inc. Press Release, (Apr. 15, 2015), 4 pgs.
Altenburg, Jeffrey D., et al., "The potential role of PD0332991 (Palbociclib) in the treatment of multiple myeloma", (Abstract), *Expert Opin Investig Drugs*, 24(2), (2015), 261-271, 1 pg.
Chiron, David, et al., "Cell-Cycle Reprogramming for PI3K Inhibition Overrides a Relapse-Specific C481S *BTK* Mutation Reveled by Longitudinal Functional Genomics in Mantle Cell Lymphoma", *Cancer Discovery*, 4(9), (2014), 1022-1035.
Chiron, David, et al., "Induction of prolonged early $G_1$ arrest by CDK4/CDK6 inhbition reprograms lymphoma cells for durable PI3Kδ inhibition through PIK3IP1", *Cell Cycle*, 12(12), (2013), 1892-1900.
Garber, Ken, "The cancer drug that almost wasn't", *Science*, 345(6199), (2014), 365-867.
Huang, Xiangao, et al., "Prolonged early $G_1$ arrest by selective CDK4/CDK6 inhibition sensitizes myeloma cells to cytotoxic killing through cell cycle-coupled loss of IRF4.", Blood, 120(5),(2012). 1095-1106.

(Continued)

*Primary Examiner* — Layla Soroush
(74) *Attorney, Agent, or Firm* — Schwegman Lundberg & Woessner, P.A.

(57) ABSTRACT

The invention involves methods of inhibiting the cancer cell cycle to make cancer cells more susceptible to chemotherapeutic agents. In particular, inhibition of CDK4 and/or CDK6 inhibits cell cycle progression in cancer cells. When combined with chemotherapy such cell cycle inhibition can effectively treat even aggressive cancer types that are drug-resistant and intractable to most chemotherapies.

12 Claims, 45 Drawing Sheets

(56) References Cited

OTHER PUBLICATIONS

Jares, Pedro, et al., "Genetic and molecular pathogenesis of mantle cell lymphoma: perspectives for new targeted therapeutics", *Nature Reviews Cancer*, 7, (Oct. 2007), 750-762.

Leonard, John P., et al., "Selective CDK4/6 inhibition with tumor responses by PD0332991 in patients with mantle cell lymphoma". *Blood*, 119(20), (2012), 4597-4607.

Menu, Eline, et al., "A Novel Therapeutic Combination Using PD 0332991 and Bortezornib: Study in the 5T33MM Myeloma Model", *Cancer Res*, 68(14), (2008), 5519-5523.

Rocca, Andrea, et al., "Palbociclib (PD 0332991): targeting the cell cycle machinery in breast cancer", *Expert Opin Pharmacother* 15(3), (2014), 407-420.

Sawai, Catherine M., et al., "Therapeutic Targeting of the Cyclin D3:CDK4/6 Complex in T Cell Leukemia", *Cancer Cell*, 22, (2012), 452-465.

Wang, Michael L., et al., "Targeting BTK with Ibrutinib in Relapsed or Refractory Mantle-Cell Lymphoma", *The New England Journal of Medicine*, 369(6), (2013), 507-516.

Yang, Chenyl, et al., "CDK4/6 inhibitor PD 0332991 sensitizes acute myeloid leukemia to cytarabine-mediated cytotoxicity", *Cancer Res*, 75(9), (2015), 1-30.

"International application serial No. PCT/US2008/011331 Invitation to Pay Add'l Fees and Partial Search Rpt mailed May 25, 2009", 9 pgs.

"International Application Serial No. PCT/US2008/011331, Search Report mailed Oct. 12, 2009".

"International Application Serial No. PCT/US2008/011331, Written Opinion mailed Oct. 12, 2009".

Baughn, Linda B, et al., "A novel orally active small molecule potently induces GI arrest in primary myeloma cells and prevents tumor growth by specific inhibition of Cdk4/6.", vol. 108, No. 11, (Nov. 2006), 113A-114A.

Dai, Y, et al., "Bortezomib and flavopiridol interact synergistically to induce apoptosis in chronic myeloid leukemia cells resistant to imatinib mesylate through both Bcr/Abl-dependent and independent mechanisms", BLOOD Jul. 15, 2004 US, vol. 104, No. 2 (Jul. 15, 2004), 509-518.

El-Deiry, W S., "Meeting Report: The International Conference Tumor Progression and Therapeutic Resistance", *Cancer Research 2005*; 65:(11), (Jun. 1, 2005), 4475-4484.

Fischer, P M, et al., "Recent progress in the discovery and development of cyclin-dependent kinase inhibitors", *Expert Opinion on Investigational Drugs* Apr. 2005 GB, vol. 14, No. 4,, (Apr. 4, 2005), 457-477.

Fry, D.W, et al., "Specific inhibition of cyclin-dependent kinase 4/6 by PD 0332991 and associated antitumor activity in human tumor xenografts", *Molecular Cancer Therapeutics, American Association of Cancer Research*, US. vol. 3, No. 11, (Nov. 1, 2004), 1427-1438.

Grant, S, et al., "The use of cyclin-dependent kinase inhibitors alone or in combination with established cytotoxic drugs in cancer chemotherapy", *Drug Resistance Updates* Feb. 2003 GB, vol. 6, No. 1, (Feb. 2003), 15-26.

Li, L., et al., "A Small Molecule Smac Mimic Potentiates TRAIL- and TNFalpha-Mediated Cell Death", *Science*, vol. 305, (2004), 1471-1474.

Malumbres, M., et al., "CDK inhibitors in cancer therapy: what is next?" *TRENDS in Pharmacological Sciences*, 29(1), (2007), 16-21.

Petersen, S. L., et al., "Autocrine TNFalpha Signalling Renders Human Cancer Cells Susceptible to Smac-Mimetic-Induced Apoptosis", *Cancer Cell*, 12, (2007), 445-456.

Schwartz, G K, et al., "Targeting the cell cycle: A new approach to cancer therapy", *Journal of Clinical Oncology 2005 US*, vol. 23, No. 36., (2005), 9408-9421.

Yoshi, K. S., et al., "In vitro antitumor properties of a novel cyclin-dependent kinase inhibitor, P276-00", *Mol. Cancer Ther..* 6(3), (2007), 918-925.

\* cited by examiner

TARGETING CDK4 AND CDK6 IN CANCER THERAPY

This application is a U.S. National Stage filing under 35 U.S.C. §371 from International Application No. PCT/US2008/011331, filed Oct. 1, 2008, published on May 14, 2009 as WO 2009/061345 A2, which claims priority to U.S. Provisional Application Ser. No. 60/986,176, filed Nov. 7, 2007, which applications are incorporated herein in their entirety.

This invention was made with U.S. Government support under grant numbers R01 AR 49436 and 1R01CA 120531, from the National Institutes of Health. As a result the U.S. government has certain rights in the invention.

BACKGROUND

Cancers occur and progress due to loss of both cell cycle and apoptotic controls. Currently, cancer chemotherapies center on the use of cytotoxic agents, which kill cancer cells but do not prevent them from dividing. This approach is often insufficient to control the rapid expansion of cancer cells during aggressive tumor growth and relapse. No anti-cancer compounds are currently available that also selectively inhibit the cell cycle. Consequently devastating cancers such as multiple myeloma are generally fatal.

SUMMARY OF THE INVENTION

According to the invention, cyclin-dependent kinase (CDK)4 and the closely related CDK6 are essential for control of cell cycle reentry and progression through G1 phase of the cell cycle. Aberrant expression of CDK4 and CDK6 is a hallmark of cancer. As demonstrated herein, treatment of cancer cells with inhibitors of CDK4 and/or CDK6 makes those cancer cells more vulnerable to chemotherapeutic agents. Thus, when CDK4 and/or CDK6 inhibitors are administered, lower concentrations of chemotherapeutic agents are needed to effectively treat cancer. Even drug-resistant cancers exhibit significantly reduced cell growth and greater susceptibility to chemotherapeutic agents. Use of CDK4 and/or CDK6 inhibitors also promotes cancer cell apoptosis and inhibits osteoclast differentiation, thereby reducing the incidence of metastasis of cancer cells to bone and destruction of bone.

Therefore, one aspect of the invention involves a method of sensitizing cancer and/or tumor cells in a mammal to a chemotherapeutic agent comprising: administering to the mammal an inhibitor of CDK4 and/or CDK6 in an amount sufficient to arrest the cancer and/or tumor cell cycle at G1 to thereby sensitize the cancer and/or tumor cells in the mammal to a chemotherapeutic agent. Cell cycle inhibition is achieved by administering at least one CDK4 small molecule inhibitor, CDK6 small molecule inhibitor, CDK4 inhibitory nucleic acid, CDK6 inhibitory nucleic acid (generally referred to herein collectively as "CDK4 and/or CDK6 inhibitors"), or a combination thereof.

One aspect of the invention is a method of sensitizing cancer and/or tumor cells in a mammal to a chemotherapeutic agent or to radiation comprising: administering to the mammal an inhibitor of CDK4 and/or CDK6 in an amount sufficient to arrest the cancer and/or tumor cell cycle at G1 to thereby sensitize the cancer and/or tumor cells in the mammal to a chemotherapeutic agent or to radiation. The method can further comprise administering to the mammal a chemotherapeutic agent in an amount sufficient to inhibit growth of the cancer and/or tumor cells in the mammal. Alternatively, the method can further comprise treating the mammal with radiation in an amount sufficient to inhibit growth of the cancer and/or tumor cells in the mammal. In some embodiments, an amount of chemotherapeutic agent or radiation is used that is sufficient to induce apoptosis in the cancer and/or tumor cells in the mammal.

The inhibitor of CDK4 and/or CDK6 is administered for several days to several weeks. For example, the inhibitor of CDK4 and/or CDK6 can be administered from about one to about seven days prior to administration of the chemotherapeutic agent or the radiation. In other embodiments, the inhibitor of CDK4 and/or CDK6 is administered for about one to twelve days. In further embodiments, the inhibitor of CDK4 and/or CDK6 is administered for at least about three days prior to administration of the chemotherapeutic agent or the radiation. The method involving administration of the inhibitor of CDK4 and/or CDK6 followed by administration of a chemotherapeutic agent and/or radiation can be repeated at least two times. In some embodiments, the method is repeated indefinitely until remission of the cancer or tumor. Thus, numerous cycles of administration of the CDK4 and/or CDK6 inhibitor(s) with a chemotherapeutic agent or radiation can be performed.

The inhibitor of CDK4 and/or CDK6 can be administered at a dosage of about 0.1 mg/Kg to about 500 mg/Kg per day. In other embodiments, the inhibitor of CDK4 and/or CDK6 is administered at a dosage of about 50 mg to about 150 mg per day.

Examples of CDK4 and/or CDK6 inhibitors that can be used include compounds of formulae I or II:

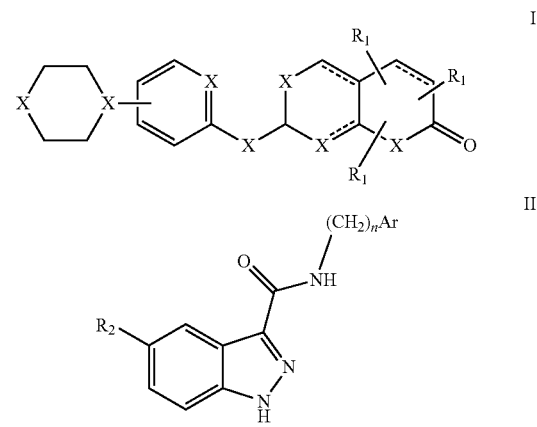

wherein:

X is a heteroatom; and each $R_1$ is independently a hydrogen, lower alkyl, carboxy-lower alkyl, oxygen, or cycloalkyl;

$R_2$ is a hydrogen or halogen atom, an $NH_2$, $NHR_2$, $NHCOR_2$, $NO_2$, CN, $CH_2NH_2$ and $CH_2NHR_2$; or phenyl or heteroaromatic group, wherein the phenyl or heteroaromatic group is optionally substituted with 1-3 lower alkyl, carboxy-lower alkyl, oxygen, or cycloalkyl groups;

Ar is phenyl or heteroaromatic group, wherein the phenyl or heteroaromatic group is optionally substituted with 1-3 lower alkyl, carboxy-lower alkyl (—(C=O)-lower alkyl), oxygen (=O), or cycloalkyl groups; and n is 0, 1, 2 or 3.

In some embodiments, X is N or NH.

Other examples of CDK4 and/or CDK6 inhibitors include compounds with the following structures:

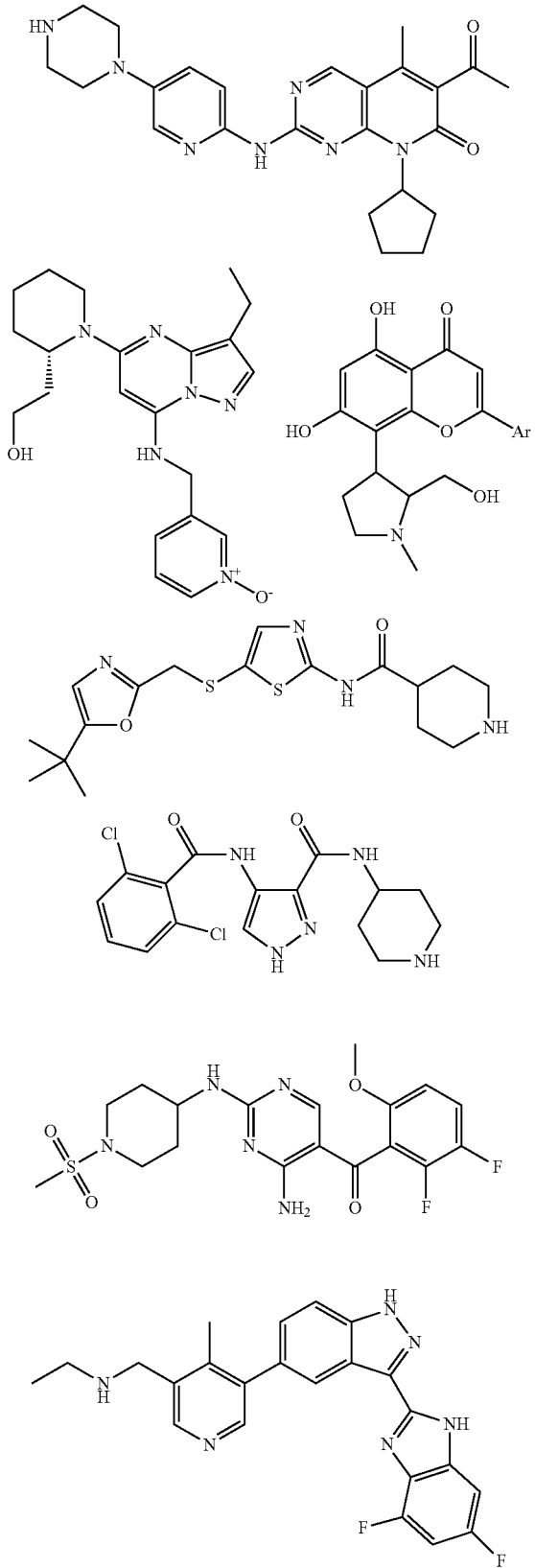

wherein Ar is phenyl or heteroaromatic group that is optionally substituted with 1-3 lower alkyl, carboxylower alkyl, oxygen, or cycloalkyl groups.

In other embodiments, the inhibitor of CDK4 and/or CDK6 is an inhibitory nucleic acid that can reduce the expression and/or activity of a CDK4 and/or CDK6 mRNA, comprising a nucleic acid that is complementary to SEQ ID NO:1 or 3. For example, the inhibitory nucleic acid can be a shRNA with sequence CCGGACAGTTCGTGAG GTGGCTTTACTCGAGTAAAGCCA CCTCACGAACTGTTTTTT (SEQ ID NO:5), CCGGGACCTGGAAAGGT GCAAAGAACTCGAGTTCTTTGC ACCTTTCCAGGTCTTTTTG (SEQ ID NO:6), or a combination thereof.

The methods of the invention have particular utility for treating cancer cells and/or tumor cells that are already resistant to a chemotherapeutic drug.

Examples of chemotherapeutic agents that can be used in the methods of the invention include a proteasome inhibitor, steroid, cytotoxic agent, photosensitizing agent, folate antagonist, pyrimidine antimetabolite, purine antimetabolite, 5-aminolevulinic acid, alkylating agent, platinum anti-tumor agent, anthracycline, DNA intercalator, epipodophyllotoxin, DNA topoisomerase inhibitor, microtubule-targeting agent, vinca alkaloid, SMAC mimetic, taxane, epothilone, an asparaginase or a combination thereof. In some embodiments, the chemotherapeutic agent is bortezomib, dexamethasone, CEP 18770, carfilzomib, cytosine arabinoside or a combination thereof. The chemotherapeutic agent can be administered at a dosage of about 0.001 mg/Kg to about 100 mg/Kg per day. Alternatively, the chemotherapeutic agent is administered at a dosage of about 0.01 mg/Kg to about 5 mg/Kg per day. In many embodiments, the amount of chemotherapeutic agent administered is lower than that used when the inhibitor of CDK4 and/or CDK6 is not administered.

The methods of the invention can be used to treat any type of cancer or tumor. Examples of cancer and/or tumor cells that can be treated include cancer cells and/or tumor cells in which the retinoblastoma gene (Rb) is expressed. In some embodiments, the cancer and/or tumor cells are hematopoietic/blood cancer cells. Examples of cancer and/or tumor cells that can be treated with the methods of the invention include mantle cell lymphoma cells, diffused large B cell lymphoma cells, acute myeloid leukemia cells, chronic lymphatic leukemia cells, chronic myelocytic leukemia cells, polycythemia vera cells, malignant lymphoma cells, multiple myeloma cells, Hodgkin's lymphoma cells, non-Hodgkin's lymphoma cells or combinations thereof. Other examples include breast cancer, glioblastoma, and metastatic lung adenocarcinoma, where CDK4 is overexpressed or the levels of physiologic inhibitors of CDK4 or CDK6 are insufficient. In some embodiments, the cancer and/or tumor cells treated with the methods of the invention are myeloma cells.

The methods of the invention reduce the growth of the cancer and/or tumor cells or kill the cancer and/or tumor cells. In some embodiments, the methods of the invention induce apoptosis in the cancer and/or tumor cells. Moreover, the methods of the invention can also inhibit osteoclast differentiation, which can inhibit metastasis of the cancer and/or tumor cells to the bone.

In general, the methods of the invention have fewer side effects than methods where the chemotherapeutic agent is administered without administration of the inhibitor of CDK4 and/or CDK6.

In some embodiments, the chemotherapeutic agent or radiation is administered while administering the inhibitor of CDK4 and/or CDK6. Moreover, the chemotherapeutic agent or radiation can be administered while administering the inhibitor of CDK4 and/or CDK6 but after administration of the inhibitor of CDK4 and/or CDK6 for at least two days.

Another aspect of the invention is an ex vivo cell culture system that recapitulates a patient's tumor cell drug sensitivity and/or tumor cell drug resistance, which comprises:
  primary cancer or tumor cells isolated from the patient;
  HS-5 or HS-27A human stromal cells; and
  an amount of human interleukin-6 (IL-6) and human insulin-like growth factor-1 (IGF-1) effective for maintaining proliferation of the cancer or tumor cells.

In some embodiments, the cell culture system includes about 1:1 to about 3:1 cancer/tumor cells to HS-5/HS-27A cells. The HS-5 or HS-27A human stromal cells can also be treated with mitomycin C to inhibit replication; In addition, the cell culture system can include about 10 to about 80 units IL-6 per ml, as well as about 30 to about 200 ng insulin-like growth factor-1 per ml.

Another aspect of the invention is a method of identifying a chemotherapeutic agent effective for treatment of a cancer or tumor in a mammal comprising:
  isolating primary cancer or tumor cells from the mammal;
  co-culturing the primary cancer or tumor cells with HS-5 or HS-27A human stromal cells to form a mixed cell culture;
  incubating the mixed cell culture with an inhibitor of CDK4 and/or CDK6, wherein the inhibitor is present in an amount sufficient to arrest the primary cancer or tumor cells at cell cycle phase G1, to thereby form an arrested cell culture;
  adding a test chemotherapeutic agent to the arrested cell culture to form a test culture; and
  observing whether the cancer or tumor cells in the test culture undergo apoptosis, to thereby identify a chemotherapeutic agent effective for treatment of a cancer or tumor in a mammal.

Another aspect of the invention is a method of identifying an effective dosage range of a chemotherapeutic agent for treatment of a cancer or tumor in a mammal comprising:
  isolating primary cancer or tumor cells from the mammal;
  co-culturing the primary cancer or tumor cells with HS-5 or HS-27A human stromal cells to form a mixed cell culture;
  incubating the mixed cell culture with an inhibitor of CDK4 and/or CDK6, wherein the inhibitor is present in an amount sufficient to arrest the primary cancer or tumor cells at cell cycle phase G1, to thereby form an arrested cell culture;
  adding a test amount of a chemotherapeutic agent to the arrested cell culture to form a test culture; and
  observing what amounts of the chemotherapeutic agent induce apoptosis of the cancer or tumor cells in the test cell culture and converting those amounts into a dosage amount, to thereby identify an effective dosage range of a chemotherapeutic agent for treatment of a cancer or tumor in the mammal.

In some embodiments, the methods of identifying effective chemotherapeutic agents and effective dosages thereof include use of about 1:1 to about 3:1 cancer/tumor cells to HS-5/HS-27A cells. The mixed cell culture can also contain an amount of human IL-6 and human insulin-like growth factor-1 effective for proliferation of the cancer or tumor cells. For example, about 10 to about 80 units IL-6 per ml as well as about of 30 to about 200 ng insulin-like growth factor-1 per ml can be included.

The inhibitor of CDK4 and/or CDK6 used in these methods of identifying effective chemotherapeutic agents and effective dosages thereof can be any of the CDK4 and/or CDK6 inhibitors described herein.

The method of identifying effective chemotherapeutic agents and an effective dosages thereof can involve addition of the inhibitor of CDK4 and/or CDK6 to the culture from 4 to 24 hours prior to addition of the chemotherapeutic agent. In some embodiments, the inhibitor of CDK4 and/or CDK6 is removed from the culture prior to addition of the chemotherapeutic agent. These methods are useful for primary cancer or tumor cells from the mammal that are resistant to one or more chemotherapeutic agents. The chemotherapeutic agent to be tested or evaluated can, for example, be a proteasome inhibitor, steroid, cytotoxic agent, photosensitizing agent, folate antagonist, pyrimidine antimetabolite, purine antimetabolite, 5-aminolevulinic acid, alkylating agent, platinum anti-tumor agent, anthracycline, DNA intercalator, epipodophyllotoxin, DNA topoisomerase inhibitor, microtubule-targeting agent, vinca alkaloid, taxane, epothilone and/or asparaginase.

Another aspect of the invention is an inhibitory nucleic acid that can reduce the expression and/or activity of a CDK4 and/or CDK6 mRNA, comprising a nucleic acid that is complementary to SEQ ID NO:1 or 3. For example, the inhibitory nucleic acid can be a shRNA with sequence CCGGACAGTTCGTGAGGTGGCTTTACTCGAGT AAAG CCACCTCACGAACTGTTTTT (SEQ ID NO:5) or CCGGGACCTGG AAAGGTGCAAAGAACTCGAGTTCTTTGCACCTTTCCAGGTCTTTTTG (SEQ ID NO:6).

Another aspect of the invention is a method of treating cancer or tumors in a mammal comprising: (a) administering at least one CDK4 and/or CDK6 inhibitor on days one (1) to fourteen (14); and (b) administering one or more chemotherapeutic agents, or radiation, periodically after about day three (3), for several weeks (e.g., about 2 to about 6 weeks). Administration of the chemotherapeutic agent(s) and the radiation can then be stopped at least temporarily. In some embodiments, this method is repeated after cessation of the chemotherapeutic agent or radiation, for example, at least two times. In some embodiments, the method is repeated indefinitely. In other embodiments, the method is repeated for ten to fifty times.

DESCRIPTION OF THE FIGURES

FIG. 1A is a schematic diagram of reversible inhibition of CDK4/6 by PD 0332991 (PD) (cyclin D is "D"). MM1.S cells were cultured with PD 0332991 for 24 hours (h) before removal of PD 0332991 and incubated further in fresh media. MM1.S and MM1.R human myeloma cell lines (HMCLs) are described in Greenstein et al. (Exper. Hematol. 31: 271-282 (2003)). FIG. 1B shows the percentage of dividing cells (detected with BrdU) and the cell cycle phase after treatment with PD for 24 hours (PD was removed at time 0). BrdU was added at time indicated (*) for 30 min before FACS analysis of BrdU uptake and DNA content. sub-G1

(<2N), G1 (2N), S (>2N<4N) and G2/M (4N). Numbers indicate the percentage of BrdU-positive cells. FIG. 1C illustrates the viability of MM1.S cells cultured with PD 0332991 for the number of days (d) indicated. FIG. 1D illustrates the mitochondrial membrane potential (MT$^-$) of MM1.S cells cultured with PD 0332991 for the number of days indicated. FIG. 1E illustrates FACS analysis of BrdU-uptake (using BrdU exposure for 30 minutes) and the DNA content per cell at the indicated times after incubation with, or removal of, PD 0332991. FIG. 1F-J illustrate the effect of the anti-cancer agent, bortezomib, upon myeloma cells when cells were also treated with PD 0332991. At 0, 4, 8 or 12 h after PD 0332991 removal, cells were incubated in the absence or presence of 250 nM bortezomib for 1 h. At 6 hr after removal of bortezomib (total 7 h), loss of mitochondrial membrane potential (MT$^-$) [or mitochondrial membrane depolarization (MMD)] by MitoTracker Red CMXRos (FIG. 1F), percentage viable cells (FIG. 1G), as well as BrdU uptake and DNA content (FIG. 1H) were monitored. The number of viable cells was determined by trypan blue exclusion staining in triplicate and presented as the percentage of the number of cells at the start of the experiment (% input). FIG. 1I shows the loss of mitochondrial membrane potential (MT$^-$) and FIG. 1J shows the percent cell viability in MM1.S cells after treatment and removal of PD 0332991, followed by incubation with bortezomib at the indicated concentrations for 12 h before analysis of MT$^-$ and viability. Data are representative of 3 independent experiments.

FIG. 2A shows the percentage of viable MM1.S cells relative to input after culturing as diagrammed. FIG. 2N shows the mitochondrial membrane potential (MT$^-$) of dexamethasone-sensitive MM1.S cells after treatment with PD and dexamethasone (dex) at the indicated concentrations as detected by JC-1. Data are representative of 3 independent experiments.

FIG. 3A shows the mitochondrial membrane potential (MT$^-$) of dexamethasone-sensitive MM1.S cells after culture in media or with HS-5 cells, with or without 24 h PD 0332991 (2 μM) pretreatment and 24 h bortezomib incubation. FIG. 3B shows the viability of dexamethasone-sensitive MM1.S cells after culture in media or with HS-5 cells, with or without 24 h PD 0332991 (2 μM) pretreatment and 24 h bortezomib incubation. FIGS. 3C and 3D show the viability of primary CD138$^+$ BM myeloma cells (BMM) isolated from patients (MM1 and MM16, respectively) that were co-cultured with HS-5 cells in the presence or absence of 2 μM PD 0332991 for 24 h before addition of bortezomib at indicated concentration for 24 h. FIG. 3E shows BrdU-uptake in primary myeloma cells isolated from patient MM16 during the initial 16 hr of PD 0332991 incubation. FIG. 3F shows the viability of primary CD138$^+$ human BM myeloma (BMM) cells from different patients (MM) treated with different amounts of bortezomib. BMMs were incubated with PD 0332991 for time indicated before treatment with bortezomib for 24 h and analysis of cell viability. Data represent mean±s.d. in triplicate. p-value was determined by two-tailed or *one-tailed t-test. FIG. 3G further illustrates the cell viability of BMM cells from various patients (MM) where the cells were treated with PD 0332991 and bortezomib as indicated for 24 h. FIG. 3H-J also illustrates the viability of BMM cells from various patients (MM), where the cells were pre-treated with PD 0332991 (2 μM) for 24 h, or left untreated, and incubated with bortezomib at indicated concentrations for 24 h and analyzed for viable cells. Data represent mean±s.d. in triplicate. p-value was determined by two-tailed or *one-tailed t-test.

" FIGS. 4C and 4D illustrate the viability of the BMM cells from MM8 (also shown in FIG. 4B) immediately after isolation (−24), at 24 h after incubation in the presence or absence of PD 0332991 (0), and at 24 h and 48 h after addition of bortezomib (4 nM). Cell death was determined by labeling DNA with To-Pro-3 at 48 h of incubation with bortezomib and indicated by the numbers shown (right). Data represent mean±s.d. in triplicate. p-value was determined by two-tailed t-test. FIG. 4E illustrates synergistic tumor suppression by the combination of PD 0332991 and bortezomib using serial noninvasive bioluminescence imaging (BLI) to visualize tumor mass on day 8 of NOD/SCID mice treated with PD 0332991 and bortezomib as diagrammed in FIG. 5A. V, ventral; D, dorsal.

FIG. 5A is a schematic diagram illustrating the timing of agents administered to, followed by bioluminescence imaging (BLI) and MT$^-$ (FACS) analyses of, NOD/SCID mice that developed aggressive tumors after injection with Luc+GFP+M1.S cells. Mice were treated with PD 0332991 (150 mg/Kg) and bortezomib (0.25 mg/Kg) on the days shown. FIG. 5B graphically illustrates the fold of tumor growth as observed by BLI on day 9, relative to day 1 for the same mice. FIG. 5C shows a FACS analysis of GFP+ MM1.S cells and BM cells that were flushed from mouse femurs on day 11 (after treatment as described in FIG. 5A), and stained with MitoTracker Red CMXRos. The percentage of MT⁻ (mean±s.d.) is as indicated. FIG. 5D shows a schematic diagram of the experimental treatment received by mice injected with NOD/SCID mice, after early in tumor development. Mice received PD 0332991 (80 mg/kg) and bortezomib (0.25 mg/Kg) at the indicated times. FIG. 5E shows bioluminescence images of tumors in mice on days 1 and 22, after treatment as indicated in FIG. 5D. FIG. 5F shows the tumor mass in mice treated as indicated and described in FIG. 5D. Bioluminescence was used as a measure of tumor mass (photons/s/cm$^2$/steradian) on days indicated. V, ventral; D, dorsal. p-value was determined by two-tailed or *one-tailed t-test. Data are representative of 3 independent experiments. FIG. 5G-H illustrate activation of caspase-8, but not TRAIL, by PD 0332991-bortezomib. FIG. 5G shows a FACS analysis of activated caspase-8 while FIG. 5H shows a q-RT-PCR analysis of TRAIL mRNA in MM1.S cells treated as described in FIG. 5A.

FIG. 6A shows an immunoblot of proteins from MM1.S cells, illustrating caspase-8,-9 and PARP cleavage in MM1.S cells cultured in media or with HS-5 cells in the presence of absence of bortezomib (4 nM) for 12 h, with or without PD 0332991 (0.25 μM) pretreatment for 24 h. FIG. 6B shows an immunoblot of BMM cellular proteins, illustrating PARP cleavage in the BMM cells shown in FIG. 4A, with or without PD 0332991 pretreatment for 17 h. FIG. 6C shows a FACS analysis of surface IL-6Rα and gp130 in MM1.S cells treated with increasing concentrations of PD 0332991 for 36 h (upper panels), or with 0.25 μM PD 0332991 for 20 h before bortezomib (4 nM) was added for 16 h (lower panels). FIG. 6D shows an immunoblot of proteins from MM1.S cells, illustrating Tyr 705 phosphorylated Stat3 (p-Stat3) and total Stat 3 in MM1.S cells cultured as shown in the lower panel of FIG. 6C and treated with 5 ng/ml human IL-6 for 10 min. FIG. 6E graphically illustrates the relative p-Stat3 levels in the lanes shown in FIG. 6D, as determined by dividing the p-Stat3 level by the total Stat3 level in each culturing condition and compared to that of IL-6 stimulation alone (lane 5). FIG. 6F-G illustrate gp130 expression, the percentage of MT⁻ cells and cell viability as detected by FACS analysis after 15 h of bortezomib treatment and knocking down gp130 expression using gp130 shRNAs (n-t shRNA is a non-target shRNA). FIG. 6H illustrates relative mRNA levels of Bim, Noxa, Mcl-1 and Bcl-2 mRNAs after 13 hr of bortezomib treatment as detected by q-RT-PCR. For FIG. 6F-H, bortezomib (4 nM) was added at 72 h post transduction of MM1.S cells with gp130 shRNA lentiviral particles. gp130 expression and the percentage of MT⁻ cells were analyzed by FACS at 15 h of bortezomib treatment (FIG. 6F-G), and q-RT-PCR analysis of Bim, Noxa, Mcl-1 and Bcl-2 mRNAs was performed at 13 hr (FIG. 6H).

FIG. 7A illustrates the relative mRNA levels of the indicated genes in MM1.S cells that were incubated with bortezomib (4 nM) for 12 h, with or without pretreatment with PD 0332991 (0.25 μM) for 24 hr as detected by q-RT-PCR analysis. FIG. 7B shows an immunoblots where a family of Bcl-2 proteins were detected. FIG. 7C illustrates immunoprecipitation (IP) and immunoblotting of Bim and proteins that interact with Bim. FIG. 7D is a schematic diagram illustrating transfection of MM1.S cells with Bim or non-targeting (n-t) siRNA and the time of addition of PD 0332991 and bortezomib, as well as the time for immunoblotting (IB) and FACS analysis of MT⁻. FIG. 7E shows an immunoblot of cellular proteins from these myeloma cells, where Bim isoforms were detected at 72 h post-transfection in the absence of PD 0332991 treatment. FIG. 7F shows the viability of MM1.S cells transduced with Bim or non-targeting (n-t) siRNA. FIG. 7G shows a FACS analysis of MT⁻ in cells treated as shown in FIG. 7D with bortezomib and PD 0332991. Data are representative of 4 independent experiments. p-value was determined by two-tailed t-test.

FIG. 8A shows an immunoblot of cellular proteins from these MM1.S cells where Bak and Bak dimer are detected in Bak immune complexes.

DETAILED DESCRIPTION OF THE INVENTION

Figure 1A:
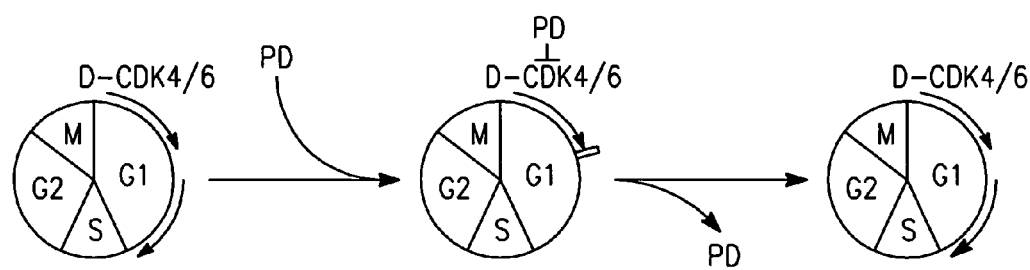
FIG. 1A-J illustrate that PD 0332991 induces G1 arrest and synchronous cell cycle progression, which primes myeloma cells for cytotoxic killing.

The invention involves methods and compositions for treating cancer that include use of CDK4 and/or CDK6 inhibitors. In some embodiments, the CDK4 and/or CDK6 inhibitors are used in combination with other chemotherapeutic agents. For example, the CDK4 and/or CDK6 inhibitors can be used prior to treatment with cytotoxic chemotherapeutic agents. Such pre-treatment with CDK4 and/or CDK6 inhibitors arrests the cancerous cell cycle (e.g., at the G1 or G1-S phase of the cell cycle). When the CDK4 and/or CDK6 inhibitors are no longer administered, the cancer cells synchronously begin to proceed through the cell cycle. However, according to the invention, the cancer cells become particularly vulnerable to cytotoxins just as they are released from the cell cycle blockade. Hence, a greater proportion of cancer cells are killed when the CDK4 and/or CDK6 inhibitors are used (e.g. before administering an chemotherapeutic agent) than when no CDK4 and/or CDK6 inhibitors are used.

Thus, the combination therapy both prevents tumor cell replication and induces synergistic killing of tumor cells. The combination therapy as invented is based on two principles.

First, prolonging the inhibition of G1 cell cycle progression can disrupt the coupling between cellular function and cell cycle progression, thereby preferentially sensitizing cycling cancer or tumor cells to killing by a cytotoxic agent.

Second, inhibition of G1 cell cycle progression can lead to synchronous S phase entry, thereby enhancing the killing of replicating cancer or tumor cells by a cytotoxic agent.

CDK4 and CDK6

Dysregulation of the cyclin-dependent kinase (CDK)4 and CDK6 activity by gain of function or loss of inhibition is one of the most frequent aberrations in cancer (Malumbres and Barbacid, 2007). Together with the regulatory D-type cyclin, CDK4 and CDK6 promote cell cycle entry and progression through G1 by antagonizing the INK4 family of CDK inhibitors (CKI)s and titrating the Cip/Kip CKIs that inhibit CDK2- cyclin E and CDK2-cyclin A (Sherr and Roberts, 1999). For example, CDK6 over-expression has been reported in hematopoietic malignancies such as lymphoma and leukemia as well as melanoma. While germline mutation of CDK4 is rare in human cancer, rare cases of hereditary melanoma do arise. Moreover, amplification of CDK4 and deletion of CDK4/6-specific CKIs, p16$^{INK4a}$ and p15$^{INK4b}$, are among the most common genomic alternations in human lung adenocarcinoma (Weir et al., 2007). Emerging evidence further suggests that a related CKI p18$^{INK4e}$ (Guan et al., 1994; Hirai et al., 1995), which suppresses pituitary adenoma development in mice (Franklin et al., 1998), is a tumor suppressor gene for human glioblastoma development (Wiedemeyer et al., 2008). CDK4 and CDK6 are dispensable during embryonic development, although they are required for the expansion of hematopoietic progenitors in mice (Malumbres et al., 2004). In preclinical models, disruption of CDK4 function protects mice from developing mammary and breast tumors induced by ErbB-2 and Ras (Landis et al., 2006; Yu et al., 2006). Thus, increasing the expression and/or function of CDK4 and/or CDK6 can give rise to cancer.

According to the invention, inhibition of CDK4 and CDK6 can significantly improve cancer therapeutic outcome by halting unscheduled cancer cell division, especially aggressive and relapsed tumors. However, targeting the cell cycle in cancer with pan-CDK inhibitors has achieved modest success so far, in part due to lack of selectivity and high toxicity (Malumbres et al., 2008). PD 0332991 is a cell permeable pyridopyrimidine with oral bioavailability. Unlike other broad-spectrum CDK inhibitors, at concentrations specific for inhibition of CDK4 and CDK6 (below 5 µM) PD 0332991 has little or no activity against at least thirty-eight other types of kinases, including CDK2 (Fry et al., 2004).

Deregulation of CDK4 and CDK6 is correlated with the loss of cell cycle control in multiple myeloma (MM), the second most common hematopoietic malignancy that is rapidly rising in incidence but remains incurable. In MM, malignant plasma cells retain self-renewing potential in contrast to normal plasma cells, which are permanently arrested in G1 due to inhibition of CDK4 and CDK6 by p18$^{INK4c}$ (Morse et al., 1997; Tourigny et al., 2002). During the stable phase of the disease, myeloma cells accumulate in the bone marrow (BM) mainly because of impaired apoptosis. However, they inevitably re-enter the cell cycle and proliferate without restraint during relapse (Chen-Kiang, 2003). While the genetic basis for cell cycle deregulation in MM remains undefined, deletion and inactivation of p18$^{INK4c}$ and other INK4 CKIs have been noted (Dib et al., 2006; Ng et al., 1997), and cyclin D is frequently overexpressed (Chesi et al., 1996; Shaughnessy et al., 2001). Gain of cyclin D expression alone, however, is insufficient to drive cell cycle progression in MM. Instead, proliferation of primary CD138+ human bone marrow myeloma (BMM) cells in vivo is preceded by mutually exclusive co-activation of CDK4-cyclin D1 or CDK6-cyclin D2 specific for each case of MM (Ely et al., 2005), suggesting that CDK4 and CDK6 are promising targets for cell cycle control in MM.

Cyclin-dependent kinase (CDK)4 and CDK6 associate with the D-type cyclin to promote cell cycle entry and progression through G1 by inactivating the retinoblastoma protein Rb and antagonizing the INK4 family of CDK inhibitors (CKI)s. They also function to titrate the Cip/Kip CKIs that inhibit CDK2-cyclin E and CDK2-cyclin A (Sherr and Roberts, 1999).

Inhibition of CDK4 and CDK6 by PD 0332991 in freshly isolated primary human BMM cells and myeloma cell lines (HMCL)s ex vivo (IC$_{50}$, 0.06 µM) led to exclusive G1 arrest in the absence of apoptosis. Additionally, PD 0332991 effectively inhibited CDK4/6 in mantle cell lymphoma (MCL) and acute myeloid leukemia cells (AML) ex vivo (Marzec et al., 2006; Wang et al., 2007), and suppressed tumor growth in myeloma, AML and solid tumor xenograft models (Baughn et al., 2006; Fry et al., 2004; Wang et al., 2007). However, myeloma tumor growth resumed upon discontinuation of PD 0332991 (Baughn et al., 2006). Therefore, administration of PD 0332991 alone is not sufficient.

CDK4 and/or CDK6 Inhibitors

According to the invention, arrest of the cell cycle, for example, using inhibitors of cyclin-dependent kinase 4 (CDK4) and/or cyclin-dependent kinase 6 (CDK6) primes cancer cells to cytotoxic killing.

A variety of CDK4 and/or CDK6 inhibitors can be used in the compositions and methods of the invention. For example, in some embodiments, the inhibitor can be a compound of formula I:

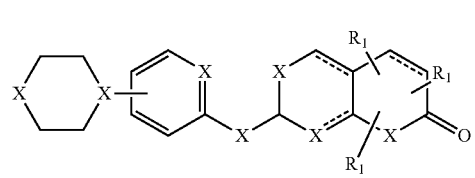

wherein:

X is a heteroatom (e.g., O, N, NH, or S);

each R$_1$ is independently a hydrogen, lower alkyl, carboxy-lower alkyl (—(C═O)-lower alkyl), oxygen (═O), or cycloalkyl groups.

PD 0332991 is one example of a compound of formula I with excellent inhibitory activity against CDK4 (IC$_{50}$, 0.011 µmol/L) and CDK6 (IC$_{50}$, 0.016 µmol/L). Moreover, PD 0332991 has little or no activity against other protein kinases. The chemical name for PD 0332991 is 6-acetyl-8-cyclopentyl-5-methyl-2-[5-piperazin-1-yl-pyridin-2-ylamino)-8H-pyrido[2,3-d]pyrimidin-7-one. The structure for PD 0332991 is shown below.

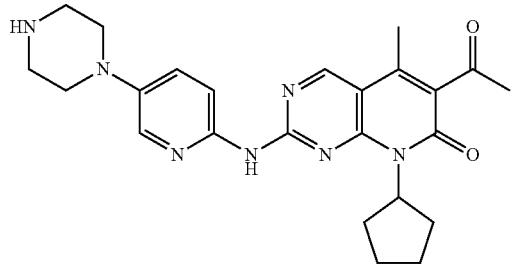 [SMILES: CC(=O)c1c(C)c2cnc(Nc3ccc(N4CCNCC4)cn3)nc2n(C2CCCC2)c1=O]

PD 0332991 is a potent anti-proliferative agent, for example, against retinoblastoma (Rb)-positive tumor cells, inducing an exclusive G$_1$ arrest, with a concomitant reduction of phosphorylation of the Ser$^{780}$/Ser$^{795}$ residues on the retinoblastoma (Rb) protein. Further information on PD 0332991 and related compounds can be found in the Examples of this application and in U.S. Application Publication 2005/0059670, the contents of which are specifically incorporated herein in their entirety.

In other embodiments, the inhibitor can be a compound of formula II:

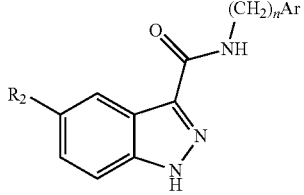

wherein:

R$_2$ is a hydrogen or halogen atom, an NH$_2$, NHR$_2$, NHCOR$_2$, NO$_2$, CN, CH$_2$NH$_2$ and CH$_2$NHR$_2$; or phenyl or heteroaromatic group, wherein the phenyl or heteroaromatic group is optionally substituted with 1-3 lower alkyl, carboxy-lower alkyl (—(C═O)-lower alkyl), oxygen (═O), or cycloalkyl groups;

Ar is phenyl or heteroaromatic group, wherein the phenyl or heteroaromatic group is optionally substituted with 1-3 lower alkyl, carboxy-lower alkyl (—(C═O)-lower alkyl), oxygen or cycloalkyl groups; and n is 0, 1, 2 or 3.

Examples of CDK4 and/or CDK6 inhibitors that can be used in the compositions and methods of the invention also include the following:

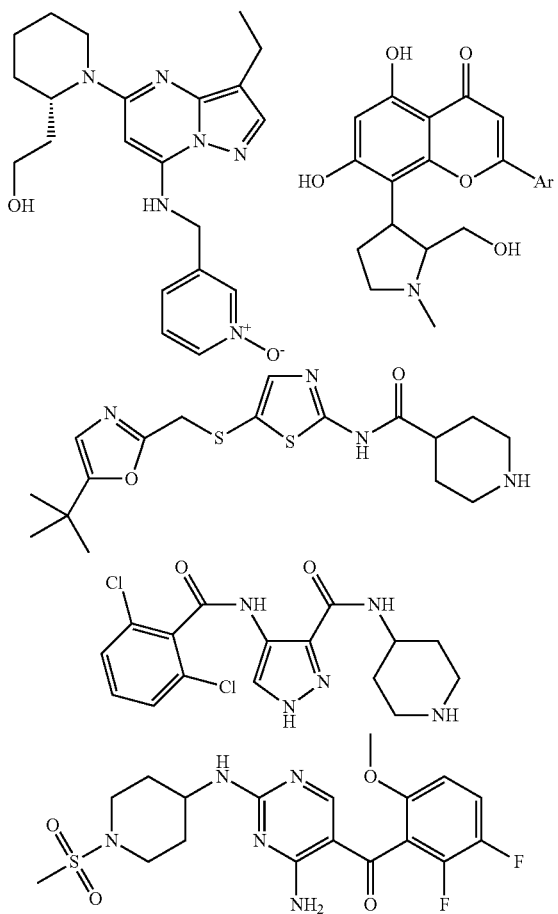

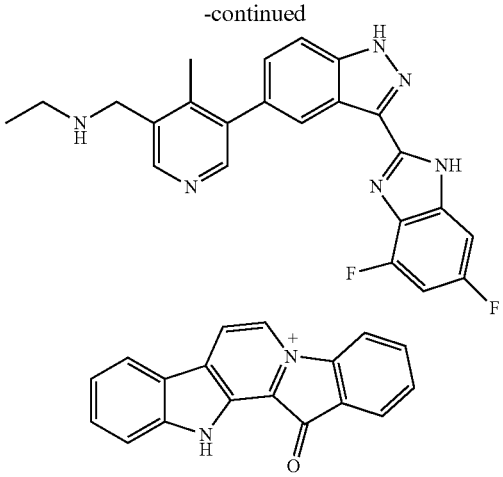

wherein Ar is phenyl or heteroaromatic group, wherein the phenyl or heteroaromatic group is optionally substituted with 1-3 lower alkyl, carboxy-lower alkyl (—(C═O)-lower alkyl), oxygen (═O), or cycloalkyl groups.

For further information on CDK4 and/or CDK6 inhibitors see, Malumbres et al., TRENDS PHARM. SCI. 29(1): 16-21 (2008); Joshi et al., MOL. CANCER THER. 6(3): 918-25 (2007, the contents of which are specifically incorporated herein in their entireties.

In cases where compounds are sufficiently basic or acidic to form acid or base salts, use of the compounds as salts may be appropriate. Examples of acceptable salts are organic acid addition salts formed with acids which form a physiological acceptable anion, for example, tosylate, methanesulfonate, acetate, citrate, malonate, tartarate, succinate, benzoate, ascorbate, ÿ-ketoglutarate, and ÿ-glycerophosphate. Suitable inorganic salts may also be formed, including hydrochloride, sulfate, nitrate, bicarbonate, and carbonate salts.

Acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Alkyl includes straight or branched C$_{1-10}$ alkyl groups, e.g., methyl, ethyl, propyl, butyl, pentyl, isopropyl, isobutyl, 1-methylpropyl, 3-methylbutyl, hexyl, and the like. Lower alkyl includes straight or branched C$_{1-6}$ alkyl groups, e.g., methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, and the like.

The term "alkylene" refers to a divalent straight or branched hydrocarbon chain (e.g., ethylene: —CH$_2$—CH$_2$—).

Cycloalkyl includes groups such as, cyclopropyl, cyclopentyl, cyclohexyl, cycloheptyl, and the like, and alkyl-substituted cycloalkyl group, preferably straight or branched C$_{1-6}$ alkyl group such as methyl, ethyl, propyl, butyl or pentyl. In some embodiments, the cycloalkyl is C$_{3-7}$ cycloalkyl, and in other embodiments the cycloalkyl is a C$_{5-7}$ cycloalkyl group such as, cyclopentyl or cyclohexyl, and the like.

Lower alkoxy includes C$_{1-6}$ alkoxy groups, such as methoxy, ethoxy or propoxy, and the like. Lower alkanoyl includes C$_{1-6}$ alkanoyl groups, such as formyl, acetyl, propanoyl, butanoyl, pentanoyl or hexanoyl, and the like. Lower alkoxycarbonyl includes $C_{2-7}$ alkoxycarbonyl groups, such as methoxycarbonyl, ethoxycarbonyl or propoxycarbonyl, and the like. Lower alkylamino group means amino group substituted by $C_{1-6}$ alkyl group, such as, methylamino, ethylamino, propylamino, butylamino, and the like. Lower alkylcarbamoyl group means carbamoyl group substituted by $C_{1-6}$ alkyl group (e.g., methylcarbamoyl, ethylcarbamoyl, propylcarbamoyl, butylcarbamoyl). Halogen atom means halogen atom such as fluorine atom, chlorine atom, bromine atom or iodine atom.

Aryl refers to a $C_{6-10}$ monocyclic or fused cyclic aryl group, such as phenyl, indenyl, or naphthyl, and the like. $C_{7-11}$ aroyl, includes groups such as benzoyl or naphthoyl.

Heterocyclic or heterocycle refers to monocyclic saturated heterocyclic groups, or unsaturated monocyclic or fused heterocyclic group containing at least one heteroatom, e.g., 0-3 nitrogen atoms (—$NR^d$— where $R^d$ is H, alkyl), 0-1 oxygen atom (—O—), and 0-1 sulfur atom (—S—). Non-limiting examples of saturated monocyclic heterocyclic group includes 5 or 6 membered saturated heterocyclic group, such as tetrahydrofuranyl, pyrrolidinyl, morpholinyl, piperidyl, piperazinyl or pyrazolidinyl. Non-limiting examples of unsaturated monocyclic heterocyclic group includes 5 or 6 membered unsaturated heterocyclic group, such as furyl, pyrrolyl, pyrazolyl, imidazolyl, thiazolyl, thienyl, pyridyl or pyrimidinyl. Non-limiting examples of unsaturated fused heterocyclic groups includes unsaturated bicyclic heterocyclic group, such as indolyl, isoindolyl, quinolyl, benzothizolyl, chromanyl, benzofuranyl, and the like.

In addition, as illustrated herein, nucleic acids that can inhibit the expression and/or translation of CDK4 and/or CDK6 can also be used as inhibitors of CDK4 and/or CDK6. Such inhibitory nucleic acids can hybridize to a CDK4 and/or CDK6 nucleic acid under intracellular or stringent conditions. The inhibitory nucleic acid is capable of reducing expression or translation of a nucleic acid encoding the CDK4 and/or CDK6. A nucleic acid encoding a CDK4 and/or CDK6 may be genomic DNA as well as messenger RNA. It may be incorporated into a plasmid vector or viral DNA. It may be single strand or double strand, circular or linear. Examples of nucleic acids encoding CDK4 and CDK6 are set forth in SEQ ID NO:1 and SEQ ID NO:2.

Nucleic acid and amino acid sequences for CDK4 and CDK6 can be found in the art, for example, in the database maintained by the National Center for Biotechnology Information (NCBI). See website at ncbi.nlm.nih.gov. For example, one nucleic acid sequence for human CDK4 is provided below for easy reference as SEQ ID NO:1 (NCBI accession number NM 000075; gi: 16936531).

```
  1  AGCCCTCCCA GTTTCCGCGC GCCTCTTTGG CAGCTGGTCA
 41  CATGGTGAGG GTGGGGGTGA GGGGGCCTCT CTAGCTTGCG
 81  GCCTGTGTCT ATGGTCGGGC CCTCTGCGTC CAGCTGCTCC
121  GGACCGAGCT CGGGTGTATG GGGCCGTAGG AACCGGCTCC
161  GGGGCCCCGA TAACGGGCCG CCCCCACAGC ACCCCGGGCT
201  GGCGTGAGGG TCTCCCTTGA TCTGAGAATG GCTACCsTCTC
241  GATATGAGCC AGTGGCTGAA ATTGGTGTCG GTGCCTATGG
281  GACAGTGTAC AAGGCCCGTG ATCCCCACAG TGGCCACTTT
321  GTGGCCCTCA AGAGTGTGAG AGTCCCCAAT GGAGGAGGAG
361  GTGGAGGAGG CCTTCCCATC AGCACAGTTC GTGAGGTGGC
```

```
 401  TTTACTGAGG CGACTGGAGG CTTTTGAGCA TCCCAATGTT
 441  GTCCGGCTGA TGGACGTCTG TGCCACATCC CGAACTGACC
 481  GGGAGATCAA GGTAACCCTG GTGTTTGAGC ATGTAGACCA
 521  GGACCTAAGG ACATATCTGG ACAAGGCACC CCCACCAGGC
 561  TTGCCAGCCG AAACGATCAA GGATCTGATG CGCCAGTTTC
 601  TAAGAGGCCT AGATTTCCTT CATGCCAATT GCATCGTTCA
 641  CCGAGATCTG AAGCCAGAGA ACATTCTGGT GACAAGTGGT
 681  GGAACAGTCA AGCTGGCTGA CTTTGGCCTG GCCAGAATCT
 721  ACAGCTACCA GATGGCACTT ACACCCGTGG TTGTTACACT
 761  CTGGTACCGA GCTCCCGAAG TTCTTCTGCA GTCCACATAT
 801  GCAACACCTG TGGACATGTG GAGTGTTGGC TGTATCTTTG
 841  CAGAGATGTT TCGTCGAAAG CCTCTCTTCT GTGGAAACTC
 881  TGAAGCCGAC CAGTTGGGCA AAATCTTTGA CCTGATTGGG
 921  CTGCCTCCAG AGGATGACTG GCCTCGAGAT GTATCCCTGC
 961  CCCGTGGAGC CTTTCCCCCC AGAGGGCCCC GCCCAGTGCA
1001  GTCGGTGGTA CCTGAGATGG AGGAGTCGGG AGCACAGCTG
1041  CTGCTGGAAA TGCTGACTTT TAACCCACAC AAGCGAATCT
1081  CTGCCTTTCG AGCTCTGCAG CACTCTTATC TACATAAGGA
1121  TGAAGGTAAT CCGGAGTGAG CAATGGAGTG GCTGCCATGG
1161  AAGGAAGAAA AGCTGCCATT TCCCTTCTGG ACACTGAGAG
1201  GGCAATCTTT GCCTTTATCT CTGAGGCTAT GGAGGGTCCT
1241  CCTCCATCTT TCTACAGAGA TTACTTTGCT GCCTTAATGA
1281  CATTCCCCTC CCACCTCTCC TTTTGAGGCT TCTCCTTCTC
1321  CTTCCCATTT CTCTACACTA AGGGGTATGT TCCCTCTTGT
1361  CCCTTTCCCT ACCTTTATAT TTGGGGTCCT TTTTTATACA
1401  GGAAAAACAA AACAAAGAAA TAATGGTCTT TTTTTTTTTT
1441  TTAAAAAAAA AAAAAAAAA AAAAAAAAA AAAA
```

The CDK4 protein encoded by SEQ ID NO:1 has NCBI accession number NM 000066 (gi: 4502735) and is provided below for easy reference (SEQ ID NO:2).

```
  1  MATSRYEPVA EIGVGAYGTV YKARDPHSGH FVALKSVRVP
 41  NGGGGGGGLP ISTVREVALL RRLEAFEHPN VVRLMDVCAT
 81  SRTDREIKVT LVFEHVDQDL RTYLDKAPPP GLPAETIKDL
121  MRQFLRGLDF LHANCIVHRD LKPENILVTS GGTVKLADFG
161  LARIYSYQMA LTPVVVTLWY RAPEVLLQST YATPVDMWSV
201  GCIFAEMFRR KPLFCGNSEA DQLGKIFDLI GLPPEDDWPR
241  DVSLPRGAFP PRGPRPVQSV VPEMEESGAQ LLLEMLTFNP
281  HKRISAFRAL QHSYLHKDEG NPE
```

One example of a nucleic acid sequence for human CDK6 is provided below for easy reference as SEQ ID NO:3 (NCBI accession number NM 001259; gi: 45827787).

```
   1 GGCTTCAGCC CTGCAGGGAA AGAAAAGTGC AATGATTCTG
  41 GACTGAGACG CGCTTGGGCA GAGGCTATGT AATCGTGTCT
  81 GTGTTGAGGA CTTCGCTTCG AGGAGGGAAG AGGAGGGATC
 121 GGCTCGCTCC TCCGGCGGCG GCGGCGGCGG CGACTCTGCA
 161 GGCGGAGTTT CGCGGCGGCG GCACCAGGGT TACGCCAGCC
 201 CCGCGGGGAG GTCTCTCCAT CCAGCTTCTG CAGCGGCGAA
 241 AGCCCCAGCG CCCGAGCGCC TGAGCCGGCG GGGAGCAAGT
 281 AAAGCTAGAC CGATCTCCGG GGAGCCCCGG AGTAGGCGAG
 321 CGGCGGCCGC CAGCTAGTTG AGCGCACCCC CCGCCCGCCC
 361 CAGCGGCGCC GCGGCGGGCG GCGTCCAGGC GGCATGGAGA
 401 AGGACGGCCT GTGCCGCGCT GACCAGCAGT ACGAATGCGT
 441 GGCGGAGATC GGGGAGGGCG CCTATGGGAA GGTGTTCAAG
 481 GCCCGCGACT TGAAGAACGG AGGCCGTTTC GTGGCGTTGA
 521 AGCGCGTGCG GGTGCAGACC GGCGAGGAGG GCATGCCGCT
 561 CTCCACCATC CGCGAGGTGG CGGTGCTGAG GCACCTGGAG
 601 ACCTTCGAGC ACCCCAACGT GGTCAGGTTG TTTGATGTGT
 641 GCACAGTGTC ACGAACAGAC AGAGAAACCA AACTAACTTT
 681 AGTGTTTGAA CATGTCGATC AAGACTTGAC CACTTACTTG
 721 GATAAAGTTC CAGAGCCTGG AGTGCCCACT GAAACCATAA
 761 AGGATATGAT GTTTCAGCTT CTCCGAGGTC TGGACTTTCT
 801 TCATTCACAC CGAGTAGTGC ATCGCGATCT AAAACCACAG
 841 AACATTCTGG TGACCAGCAG CGGACAAATA AAACTCGCTG
 881 ACTTCGGCCT TGCCCGCATC TATAGTTTCC AGATGGCTCT
 921 AACCTCAGTG GTCGTCACGC TGTGGTACAG AGCACCCGAA
 961 GTCTTGCTCC AGTCCAGCTA CGCCACCCCC GTGGATCTCT
1001 GGAGTGTTGG CTGCATATTT GCAGAAATGT TCGTAGAAA
1041 GCCTCTTTTT CGTGGAAGTT CAGATGTTGA TCAACTAGGA
1081 AAAATCTTGG ACGTGATTGG ACTCCCAGGA GAAGAAGACT
1121 GGCCTAGAGA TGTTGCCCTT CCCAGGCAGG CTTTTCATTC
1161 AAAATCTGCC CAACCAATTG AGAAGTTTGT AACAGATATC
1201 GATGAACTAG GCAAAGACCT ACTTCTGAAG TGTTTGACAT
1241 TTAACCCAGC CAAAAGAATA TCTGCCTACA GTGCCCTGTC
1281 TCACCCATAC TTCCAGGACC TGGAAAGGTG CAAAGAAAAC
1321 CTGGATTCCC ACCTGCCGCC CAGCCAGAAC ACCTCGGAGC
1361 TGAATACAGC CTGAGGCCTC AGCAGCCGCC TTAAGCTGAT
1401 CCTGCGGAGA ACACCCTTGG TGGCTTATGG GTCCCCCTCA
1441 GCAAGCCCTA CAGAGCTGTG GAGGATTGCT ATCTGGAGGC
1481 CTTCCAGCTG CTGTCTTCTG GACAGGCTCT GCTTCTCCAA
1521 GGAAACCGCC TAGTTTACTG TTTTGAAATC AATGCAAGAG
1561 TGATTGCAGC TTTATGTTCA TTTGTTTGTT TGTTTGTCTG
1601 TTTGTTTCAA GAACCTGGAA AAATTCCAGA AGAAGAGAAG
1641 CTGCTGACCA ATTGTGCTGC CATTTGATTT TTCTAACCTT
1681 GAATGCTGCC AGTGTGGAGT GGGTAATCCA GGCACAGCTG
1721 AGTTATGATG TAATCTCTCT GCAGCTGCCG GGCCTGATTT
1761 GGTACTTTTG AGTGTGTGTG TGCATGTGTG TGTGTGTGTG
1801 TGTGTGTGTG TGTGTGTATG TGAGAGATTC TGTGATCTTT
1841 TAAAGTGTTA CTTTTTGTAA ACGACAAGAA TAATTCAATT
1881 TTAAAGACTC AAGGTGGTCA GTAAATAACA GGCATTTGTT
1921 CACTGAAGGT GATTCACCAA AATAGTCTTC TCAAATTAGA
1961 AAGTTAACCC CATGTCCTCA GCATTTCTTT TCTGGCCAAA
2001 AGCAGTAAAT TTGCTAGCAG TAAAAGATGA AGTTTTATAC
2041 ACACAGCAAA AAGGAGAAAA AATTCTAGTA TATTTTAAGA
2081 GATGTGCATG CATTCTATTT AGTCTTCAGA ATGCTGAATT
2121 TACTTGTTGT AAGTCTATTT TAACCTTCTG TATGACATCA
2161 TGCTTTATCA TTTCTTTTGG AAAATAGCCT GTAAGCTTTT
2201 TATTACTTGC TATAGGTTTA GGGAGTGTAC CTCAGATAGA
2241 TTTTAAAAAA AAGAATAGAA AGCCTTTATT TCCTGGTTTG
2281 AAATTCCTTT CTTCCCTTTT TTGTTGTTG TTATTGTTGT
2321 TTGTTGTTGT TATTTTGTTT TTGTTTTTAG GAATTTGTCA
2361 GAAACTCTTT CCTGTTTTGG TTTGGAGAGT AGTTCTCTCT
2401 AACTAGAGAC AGGAGTGGCC TTGAAATTTT CCTCATCTAT
2441 TACACTGTAC TTTCTGCCAC ACACTGCCTT GTTGGCAAAG
2481 TATCCATCTT GTCTATCTCC CGGCACTTCT GAAATATATT
2521 GCTACCATTG TATAACTAAT AACAGATTGC TTAAGCTGTT
2561 CCCATGCACC ACCTGTTTGC TTGCTTTCAA TGAACCTTTC
2601 ATAAATTCGC AGTCTCAGCT TATGGTTTAT GGCCTCGATT
2641 CTGCAAACCT AACAGGGTCA CATATGTTCT CTAATGCAGT
2681 CCTTCTACCT GGTGTTTACT TTTGCTACCC AAATAATGAG
2721 TAGGATCTTG TTTTCGTATA CCCCCACCAC TCCCATTGCT
2761 ACCAACTGTC ACCTTGTGCA CTCCTTTTTT ATAGAAGATA
2801 TTTTCAGTGT CTTTACCTGA GGGTATGTCT TTAGCTATGT
2841 TTTAGGGCCA TACATTACT CTATCAAATG ATCTTTTCTC
2881 CATCCCCCAG GCTGTGCTTA TTTCTAGTGC CTTGTGCTCA
2921 CTCCTGCTCT CTACAGAGCC AGCCTGGCCT GGGCATTGTA
2961 AACAGCTTTT CCTTTTTCTC TTACTGTTTT CTCTACAGTC
3001 CTTTATATTT CATACCATCT CTGCCTTATA AGTGGTTTAG
3041 TGCTCAGTTG GCTCTAGTAA CCAGAGGACA CAGAAAGTAT
3081 CTTTTGGAAA GTTTAGCCAC CTGTGCTTTC TGACTCAGAG
3121 TGCATGCAAC AGTTAGATCA TGCAACAGTT AGATTATGTT
3161 TAGGGTTAGG ATTTTCAAAG AATGGAGGTT GCTGCACTCA
3201 GAAAATAATT CAGATCATGT TTATGCATTA TTAAGTTGTA
```

```
3241 CTGAATTCTT TGCAGCTTAA TGTGATATAT GACTATCTTG
3281 AACAAGAGAA AAAACTAGGA GATGTTTCTC CTGAAGAGCT
3321 TTTGGGGTTG GGAACTATTC TTTTTTAATT GCTGTACTAC
3361 TTAACATTGT TCTAATTCAG TAGCTTGAGG AACAGGAACA
3401 TTGTTTTCTA GAGCAAGATA ATAAAGGAGA TGGGCCATAC
3441 AAATGTTTTC TACTTTCGTT GTGACAACAT TGATTAGGTG
3481 TTGTCAGTAC TATAAATGCT TGAGATATAA TGAATCCACA
3521 GCATTCAAGG TCAGTCTAC TCAAAGTCTC ACATGGAAAA
3561 GTGAGTTCTG CCTTTCCTTT GATCGAGGGT CAAAATACAA
3601 AGACATTTTT GCTAGGGCCT ACAAATTGAA TTTAAAAACT
3641 CACTGCACTG ATTCATCTGA GCTTTTTGGT TAGTATTCAT
3681 GGCTAGAGTG AACATAGCTT TAGTTTTTGC TGTTGTAAAA
3721 GTGTTTTCAT AAGTTCACTC AAGAAAAATG CAGCTGTTCT
3761 GAACTGGAAT TTTTCAGCAT TCTTTAGAAT TTTAAATGAG
3801 TAGAGAGCTC AACTTTTATT CCTAGCATCT GCTTTTGACT
3841 CATTTCTAGG CAGTGCTTAT GAAGAAAAAT TAAAGCACAA
3881 ACATTCTGGC ATTCAATCGT TGGCAGATTA TCTTCTGATG
3921 ACACAGAATG AAAGGGCATC TCAGCCTCTC TGAACTTTGT
3961 AAAAATCTGT CCCCAGTTCT TCCATCGGTG TAGTTGTTGC
4001 ATTTGAGTGA ATACTCTCTT GATTTATGTA TTTTATGTCC
4041 AGATTCGCCA TTTCTGAAAT CCAGATCCAA CACAAGCAGT
4081 CTTGCCGTTA GGGCATTTTG AAGCAGATAG TAGAGTAAGA
4121 ACTTAGTGAC TACAGCTTAT TCTTCTGTAA CATATGGTTT
4161 CAAACATCTT TGCCAAAAGC TAAGCAGTGG TGAACTGAAA
4201 AGGGCATATT GCCCCAAGGT TACACTGAAG CAGCTCATAG
4241 CAAGTTAAAA TATTGTGACA GATTTGAAAT CATGTTTGAA
4281 TTTCATAGTA GGACCAGTAC AAGAATGTCC CTGCTAGTTT
4321 CTGTTTGATG TTTGGTTCTG GCGGCTCAGG CATTTTGGGA
4361 ACTGTTGCAC AGGGTGCAGT CAAAACAACC TACATATAAA
4401 AATTACATAA AAGAACCTTG TCCATTTAGC TTTCATAAGA
4441 AATCCCATGG CAAAGAGTAA TAAAAAGGAC CTAATCTTAA
4481 AAATACAATT TCTAAGCACT TGTAAGAACC CAGTGGGTTG
4521 GAGCCTCCCA CTTTGTCCCT CCTTTGAAGT GGATGGGAAC
4561 TCAAGGTGCA AGAACCTGT TTTGGAAGAA AGCTTGGGGC
4601 CATTTCAGCC CCTGTATTC TCATGATTTT CTCTCAGGAA
4641 GCACACACTG TGAATGGCAG ACTTTTCATT TAGCCCCAGG
4681 TGACTTACTA AAAATAGTTG AAAATTATTC ACCTAAGAAT
4721 AGAATCTCAG CATTGTGTTA AATAAAAATG AAAGCTTTAG
4761 AAGGCATGAG ATGTTCCTAT CTTAAATAAA GCATGTTTCT
4801 TTTCTATAGA GAATGTATA GTTTGACTCT CCAGAATGTA
4841 CTATCCATCT TGATGAGAAA ACTCTTAAAT AGTACCAAAC
4881 ATTTTGAACT TTAAATTATG TATTTAAAGT GAGTGTTTAA
4921 GAAACTGTAG CTGCTTCTTT TACAAGTGGT GCCTATTAAA
4961 GTCAGTAATG GCCATTATTG TTCCATTGTG GAAATTAAAT
5001 TATGTAAGCT TCCTAATATC ATAAACATAT TAAAATTCTT
5041 CTAAAATATT GCTTTTCTTT TAAGTGACAA TTTGACTATT
5081 CTTATGATAA GCACATGAGA GTGTCTTACA TTTTCCAAAA
5121 GCAGGCTTTA ATTGCATAGT TGAGTCTAGG AAAAAATAAT
5161 GTTAAAAGTG AATATGCCAC CATAATTACT TAATTATGTT
5201 AGTATAGAAA CTACAGAATA TTTACCCTGG AAAGAAAATA
5241 TTGGAATGTT ATTATAAACT CTTAGATATT TATATAATTC
5281 AAAAGAATGC ATGTTTCACA TTGTGACAGA TAAAGATGTA
5321 TGATTTCTAA GGCTTTAAAA ATTATTCATA AAACAGTGGG
5361 CAATAGATAA AGGAAATTCT GGAGAAAATG AAGGTATTTA
5401 AAGGGTAGTT TCAAAGCTAT ATATATTTTG AAGGATATAT
5441 TCTTTATGAA CAAATATATT GTAAAAATTT ATACTAAGGT
5481 CATCTGGTAA CTGTGGGATT AATATGGTCG AAAACAAATG
5521 TTATGGAGAA GCTGTCCCAA GCAAACTAAA TTACCTGTAC
5561 TTTTTTCCCA TTTCAAGGGA AGAGGCAACC ACATGAAGCA
5601 ATACTTCTTA CACATGCCTA AGAACGTTCA TTGAAAAAAT
5641 AAATTTTTAA AAGGCATGTG TTTCCTATGC CACCAATACT
5681 TTTGAAAAAT TGTGAACCTT ACCCAAAACC ATTTATCATG
5721 TCCATTAAGT ATATTTGGGT ATATAATTAG GAAGATATTT
5761 ACATGTTCCA TCTCCACAGT GGAAAAACTT ATTGAGGCTA
5801 CCAAAGTGTG CCAAGAAATG TAAGTCCTTA GAGTAATTAG
5841 AAATGCTGTT TTCCTCAAAA GCATGAGAAA CTAGCATTTT
5881 CATTTCTTAT TTACTCCCTT TCTATATCAA TGCAATTCAC
5821 AACCCAATTT TAATACATCC CTATATCTCA AGCATTTCTA
5861 TCTTGTACTT TTTCAGAAAA TAAACCAAAA ATAATCCTTT
6001 GGTCTCTCTA TCTTCTGACC TTTGTAAGCA ACAGAAATGT
6041 AAAAACAGAA GGGGTCCAAT TTTTACACGT TTTTTTCTCA
6081 AGTAGCCTTT CTGGGGATTT TTATTTTCTT AATGAAGTGC
6121 CAATCAGCTT TTCAAAATGT TTTCTATTTC TCAGCATTTC
6161 CAGGAAGTGA TAACGTTTAG CTAAATGAGT AGAAGTGGAC
6201 TTCCTTCAAC ATATTGTTAC CTTGTCTAGC CTTAGGAAGA
6241 AAACAAGAGC CACCTGAAAA TAAATACAGG CTCTTTTCGA
6281 GCATCTGCTG AAATACTGTT ACAGCAATTT GAAGTTGATG
6321 TGGTAGGAAA GGAAGGTGAC TTTTCTTGCA AAAGTCTTTC
6361 TAAACATTCA CACTGTCCTA AGAGATGAGC TTTCTTGTTT
6401 TATTCCGGTA TATTCCACAA GGTGGCACTT TTAGAGAAAA
6441 ACAAATCTGA TGAAGACTAA AGAGGTACTT CTAAAAGAGA
```

-continued

```
6481 TTTCATTCTA ACTTTATTTT TCTGCGCATA TTTAACTCTT
6521 TCCTAGCACT TGTTTTTTGG GATGATTAAT AGTCTCTATA
6561 ATGTTCTGTA ACTTCAATAT TTTACTTGTT ACCTAGGTTC
6601 TGAACAATTG TCTGCAAATA AATTGTTCTT AAGGATGGAT
6641 AATACACCCA TTTTGATCAT TTAAGTAAAG AAAGCCTAGT
6681 CATTCATTCA GTCAAGAAAA AATTTTTGAA GTACCCAGTT
6721 ACCTTACTTT TCTAGATTAA AACAGGCTTA GTTACTAAAA
6761 AGGCAGTCCT CATCTGTGAA CAGGATAGTT TCGTTAGAAG
6801 TATAAAACTC CTTTAGTGGC CCCAGTTAAA ACACACATAC
6841 CCTCTCTGCT GCTTTCAAAT TCCCTAGCAT GGTGGCCTTT
6881 CAACATTGAT TAAATTTTAA AATCCTAATT TAAAGATCAG
6921 GTGAGCAAAA TGAGTAGCAC ATCAGTAATT CAGTAGACAA
6961 AACTTTTGTC TGAAAAATTG CTGTATTGAA ACAGAGCCCT
7001 AAAATACCAA AAGACCAGGT AATTTTAACA TTTGTGGAAT
7041 CACAAATGTA AATTCATAAG AAGCTCTAAT TAAAAAAAAA
7081 AAGTCTGAAG TATATGAGCA TAACAACTTA GGAGTGTGTC
7121 TACATACTTA ACTTTTGAAG TTTTTTGGCA ACTTTATATA
7161 CTTTTTTTAA ATTTACAAGT CTACTTAAAG ACTTCTTATA
7201 CCCCAAATGA TTAAGTTAAT TTTAGAGGTC ACCTTTCTCA
7241 CAGCAGTGTC ACTTGAAATT TAGTAGGGAA GGATATTGCA
7281 GTATTTTCA GTTTCCTTAG CACAGCACCA CAGAAAGCAG
7321 CTTATTCCTT TGAGTGGCA GACACTCGAC GGTGCCTGCC
7361 CAACTTTCCT CCTGAGTGGC AAGCAGATGA GTCTCAGTAA
7401 TTCATACTGA ACCAAAATGC CACATACACT AGGGGCAGTC
7441 AGAAACTGGC TGAGAAATCC CCCGCCTCAT TCGCCCCTCT
7481 GCTCCCAGGA ACTAGAGTCC AGTTAAAGCC CCTATGCGAA
7521 AGGCCGAATT CCACCCCAGG GTTTGTTATA ACAGTGGCCA
7561 GTCTGAACCC CATTTGCTCG TGCTCAAAAC TTGATTCCCA
7601 CTTGAAAGCC TTCCGGGCGC GCTGCCTCGT TGCCCCGCCC
7641 CTTTGGCAGG AGAGAGGCAG TGGGCGAGGC CGGGCTGGGG
7681 CCCCGCCTCC CACTCACCTG CCGGTGCCTG AAATTATGTG
7721 CGGCCCCGCG GGCTGCTTTC CGAGGTCAGA GTGCCCTGCT
7761 GCTGTCTCAG AGGCATCTGT TCTGCAAATC TTAGGAAGAA
7801 AAATGTCCCT AGTAGCAAAC GGGTGTCTTC TGTGCATAAA
7841 TAAGTACAAC ACAATTCTCC GAAAGTTCGG GTAAAAAGAG
7881 ATGCGGTAGC AGCTGCCCTG TGTGAAGCTG TCTACCCCGC
7921 ATCTCTCAGG CGCTAAGCTC AGTTTTTGTT TTTGTTTTTG
7961 TTTTTTTAAA GAAAAGATGT ATAATTGCAG GAATTTTTTT
8001 TTATTTTTTT ATTTTCCATC ATTCTATATA TGTGATGGTG
8041 AAAGATATGC CTGGAAAAGT TTTGTTTTGA AAAGTTTATT
8081 TTCTGCTTCG TCTTCAGTTG GCAAAAGCTC TCAATTCTTT
```

```
8121 AGCTTCCAGT TTCTTTTCTC TCTTTTTCTT TGTTAGGTAA
8161 TTAAAGGTAT GTAAACAAAT TATCTCATGT AGCAGGGGAT
8201 TTTCATGTTG AGAGGAATCT TCCGTGTGAG TTGTTTGGTC
8241 ACACAAATAA CCCTTTCTCA ATTTTAGGAG TTTGGATTGT
8281 CAAATGTAGG TTTTTCTCAA AGGGGCATA TAACTACATA
8321 TTGACTGCCA AGAACTATGA CTGTAGCACT AATCAGCACA
8361 CATAGAGCCA CACAATTATT TAATTTCTAA CTCTCTGTGG
8401 TCCCTAGAAA AATTCCGTTG ATGTGCTTAG GTTAAAGTTC
8441 TGAAGATACC CGTTGTACCC TTACTTGAAA GTTTCTAATC
8481 TTAAGTTTTA TGAAATGCAA TAATATGTAT CAGCTAGCAA
8521 TATTTCTGTG ATCACCAACA ACTCTCAGTT TGATCTTAAA
8561 GTCTGAATAA TAAAACAAAT CCCAGCAGTA ATACATTTCT
8601 TAAACCTCAC AGTGCATGAT ATATCTTTTC ATTCTGATCC
8641 TGTGTTTGCA AAAATATACA CATGTATATC ATAGTTCCTC
8681 ACTTTTTATT CATTTGTTTT CCTATTACCT GTAGTAAATA
8721 TATTAGTTAG TACATGGAAT TTATAGCATC AGCTACCCCC
8761 AGGAACAGCA CCTGACAGGC GGGGGATTTT TTTTCAAGTT
8801 GTTCTACATT TGCATAAATT ATTTCTATTA TTATTCATGT
8841 ATGTTATTTA TTTCTGAATC ACACTAGTCC TGTGAAAGTA
8881 CAACTGAAGG CAGAAAGTGT TAGGATTTTG CATCTAATGT
8921 TCATTATCAT GGTATTGATG GACCTAAGAA AATAAAAATT
8961 AGACTAAGCC CCCAAATAAG CTGCATGCAT TTGTAACATG
9001 ATTAGTAGAT TTGAATATAT AGATGTAGTA TTTTGGGTAT
9041 CTAGGTGTTT TATCATTATG TAAAGGAATT AAAGTAAAGG
9081 ACTTTGTAGT TGTTTTTATT AAATATGCAT ATAGTAGAGT
9121 GCAAAAATAT AGCAAAAATA AAAACTAAAG GTAGAAAAGC
9161 ATTTTAGATA TGCCTTAATT TAGAAACTGT GCCAGGTGGC
9201 CCTCGGAATA GATGCCAGGC AGAGACCAGT GCCTGGGTGG
9241 TGCCTCCTCT TGTCTGCCCT CATGAAGAAG CTTCCCTCAC
9281 GTGATGTAGT GCCCTCGTAG GTGTCATGTG GAGTAGTGGG
9301 AACAGGCAGT ACTGTTGAGA GGAGAGCAGT GTGAGAGTTT
9361 TTCTGTAGAA GCAGAACTGT CAGCTTGTGC CTTGAGGCTT
9401 CCAGAACGTG TCAGATGGAG AAGTCCAAGT TTCCATGCTT
9441 CAGGCAACTT AGCTGTGTAC AGAAGCAATC CAGTGTGGTA
9481 ATAAAAGCA AGGATTGCCT GTATAATTTA TTATAAAATA
9521 AAAGGGATTT TAACAACCAA CAATTCCCAA CACCTCAAAA
9561 GCTTGTTGCA TTTTTTGGTA TTTGAGGTTT TTATCTGAAG
9601 GTTAAAGGGC AAGTGTTTGG TATAGAAGAG CAGTATGTGT
9641 TAAGAAAAGA AAAATATTGG TTCACGTAGA GTGCAAATTA
9681 GAACTAGAAA GTTTTATACG ATTATCATTT TGAGATGTGT
```

```
9721 TAAAGTAGGT TTTCACTGTA AAATGTATTA GTGTTTCTGC

9761 ATTGCCATAG GGCCTGGTTA AAACTTTCTC TTAGGTTTCA

9801 GGAAGACTGT CACATACAGT AAGCTTTTTT CCTTCTGACT

9841 TATAATAGAA AATGTTTTGA AAGTAAAAAA AAAAAATCTA

9881 ATTTGGAAAT TTGACTTGTT AGTTTCTGTG TTTGAAATCA

9921 TGGTTCTAGA AATGTAGAAA TTGTGTATAT CAGATACTCA

9961 TCTAGGCTGT GTGAACCAGC CCAAGATGAC CAACATCCCC

10001 ACACCTCTAC ATCTCTGTCC CCTGTATCTC TTCCTTTCTA

10041 CCACTAAAGT GTTCCCTGCT ACCATCCTGG CTTGTCCACA

10081 TGGTGCTCTC CATCTTCCTC CACATCATGG ACCACAGGTG

10121 TGCCTGTCTA GGCCTGGCCA CCACTCCCAA CTTGACCTAG

10161 CCACATTCAT CTAGAGATGG TTCCTGATGC TGGGCACAGA

10201 CTGTGCTCAT GGCACCCATT AGAAATGCCT CTAGCATCTT

10241 TGTATGCATC TTGATTTTTA AACCAAGTCA TTGTACAGAG

10281 CATTCAGTTT TGGCTGTGGT ACCAAGAGAA AAACTAATCA

10321 AGAATATAAA CCACATTCCA GGCTGCTGTT TTCTCTCCAT

10361 CTACAGGCCA CACTTTTACT GTATTTCTTC ATACTTGAAA

10401 TTCATTCTGC TATTTTCATA TCAGGGTACA GACTTATAAG

10441 GGTGCATGTT CCTTAAAGGT GCATAATTAT TCTTATTCCG

10481 TTTGCTTATA TTGCTACAGA ATGCTCTGTT TTGGTGCTTT

10521 GAGTTCTGCA GACCCAAGAA GCAGTGTGGA AATTCACTGC

10561 CTGGGACACA GTCTTATAAG AATGTTGGCA GGTGACTTTG

10601 TATCAGATGT TGCTTCTCTT TTCTCTGTAC ACAGATTGAG

10641 AGTTACCACA GTGGCCTGTC GGGTCCACCC TGTGGGTGCA

10681 GCACAGCTCT CTGAAAGCAA GAACCTTCCT ACCTATTCTA

10721 ACGTTTTTGC CCTCTAAGAA AAATGGCCTC AGGTATGGTA

10761 TAGACATAGC AAGAGGGGAA GGGCTGTCTC ACTCTAGCAA

10801 CCATCCCTCC ATTACACACA GAAAGCCCTC TTGAAGCAAA

10841 AGAAGAAGAA AGAAAGAAAG CTTATCTCTA AGGCTACTGT

10881 CTTCAGAATG CTCTGAGCTG AATGCTCTTG CTCCTTTCCC

10921 AAGAGGCAGA TGAAAATATA GCCAGTTTAT CTATACCCTT

10961 CCTATCTGAG GAGGAGAATA GAAAAGTAGG GTAAATATGT

11001 AACGTAAAAT ATGTCATTCA AGGACCACCA AAACTTTAAG

11041 TACCCTATCA TTAAAAATCT GGTTTTAAAA GTAGCTCAAG

11081 TAAGGGATGC TTTGTGACCC AGGGTTTCTG AAGTCAGATA

11121 GCCATTCTTA CCTGCCCCTT ACTCTGACTT ATTGGGAAAG

11161 GGAGAACTGC AGTGGTGTTT CTGTTGCAGT GGCAAAGGTA

11201 ACATGTCAGA AAATTCAGAG GGTTGCATAC CAATAATCCT

11241 TTGGAAACTG GATGTCTTAC TGGGTGCTAG AATGAAAATG

11281 TAGGTATTTA TTGTCAGATG ATGAAGTTCA TTGTTTTTTT

11321 CAAAATTGGT GTTGAAATAT CACTGTCCAA TGTGTTCACT

11361 TATGTGAAAG CTAAATTGAA TGAGGCAAAA AGAGCAAATA

11401 GTTTGTATAT TTGTAATACC TTTTGTATTT CTTACAATAA

11441 AAATATTGGT AGCAAATAAA AATAATAAAA ACAATAACTT

11481 TAAACTGCTT TCTGGAGATG AATTACTCTC CTGGCTATTT

11521 TCTTTTTTAC TTTAATGTAA AATGAGTATA ACTGTAGTGA

11561 GTAAAATTCA TTAAATTCCA AGTTTTAGCA GAAAAAAAAA

11601 AAAAAAAAA A
```

The CDK6 protein encoded by SEQ ID NO:3 has NCBI accession number NP 001250 (gi: 4502741) and is provided below for easy reference (SEQ ID NO:4).

```
  1 MEKDGLCRAD QQYECVAEIG EGAYGKVFKA RDLKNGGRFV

41 ALKRVRVQTG EEGMPLSTIR EVAVLRHLET FEHPNVVRLF

81 DVCTVSRTDR ETKLTLVFEH VDQDLTTYLD KVPEPGVPTE

121 TIKDMMFQLL RGLDFLHSHR VVHRDLKPQN ILVTSSGQIK

161 LADFGLARIY SFQMALTSVV VTLWYRAPEV LLQSSYATPV

201 DLWSVGCIFA EMFRRKPLFR GSSDVDQLGK ILDVIGLPGE

241 EDWPRDVALP RQAFHSKSAQ PIEKFVTDID ELGKDLLLKC

281 LTFNPAKRIS AYSALSHPYF QDLERCKENL DSHLPPSQNT

321 SELNTA
```

An inhibitory nucleic acid is a polymer of ribose nucleotides or deoxyribose nucleotides having more than three nucleotides in length. An inhibitory nucleic acid may include naturally-occurring nucleotides; synthetic, modified, or pseudo-nucleotides such as phosphorothiolates; as well as nucleotides having a detectable label such as $^{32}P$, biotin, fluorescent dye or digoxigenin. An inhibitory nucleic acid that can reduce the expression and/or activity of a CDK4 and/or CDK6 nucleic acid may be completely complementary to the CDK4 and/or CDK6 nucleic acid (e.g., SEQ ID NO:1 or 3). Alternatively, some variability between the sequences may be permitted.

An inhibitory nucleic acid of the invention can hybridize to a CDK4 and/or CDK6 nucleic acid under intracellular conditions or under stringent hybridization conditions. The inhibitory nucleic acids of the invention are sufficiently complementary to endogenous CDK4 and/or CDK6 nucleic acids to inhibit expression of a CDK4 and/or CDK6 nucleic acid under either or both conditions. Intracellular conditions refer to conditions such as temperature, pH and salt concentrations typically found inside a cell, e.g. a mammalian cell. One example of such a mammalian cell is a cancer cell (e.g., a myeloma cell), or any cell where CDK4 and/or CDK6 is or may be expressed.

Generally, stringent hybridization conditions are selected to be about 5° C. lower than the thermal melting point ($T_m$) for the specific sequence at a defined ionic strength and pH. However, stringent conditions encompass temperatures in the range of about 1° C. to about 20° C. lower than the thermal melting point of the selected sequence, depending upon the desired degree of stringency as otherwise qualified herein. Inhibitory nucleic acids that comprise, for example, 2, 3, 4, or 5 or more stretches of contiguous nucleotides that are precisely complementary to a CDK4 and/or CDK6 coding sequence, each separated by a stretch of contiguous nucleotides that are not complementary to adjacent coding sequences, may inhibit the function of a CDK4 and/or CDK6 nucleic acid. In general, each stretch of contiguous nucleotides is at least 4, 5, 6, 7, or 8 or more nucleotides in length. Non-complementary intervening sequences may be 1, 2, 3, or 4 nucleotides in length. One skilled in the art can easily use the calculated melting point of an inhibitory nucleic acid hybridized to a sense nucleic acid to estimate the degree of mismatching that will be tolerated for inhibiting expression of a particular target nucleic acid. Inhibitory nucleic acids of the invention include, for example, a ribozyme or an antisense nucleic acid molecule.

The antisense nucleic acid molecule may be single or double stranded (e.g. a small interfering RNA (siRNA)), and may function in an enzyme-dependent manner or by steric blocking. Antisense molecules that function in an enzyme-dependent manner include forms dependent on RNase H activity to degrade target mRNA. These include single-stranded DNA, RNA and phosphorothioate molecules, as well as the double-stranded RNAi/siRNA system that involves target mRNA recognition through sense-antisense strand pairing followed by degradation of the target mRNA by the RNA-induced silencing complex. Steric blocking antisense, which are RNase-H independent, interferes with gene expression or other mRNA-dependent cellular processes by binding to a target mRNA and getting in the way of other processes. Steric blocking antisense includes 2'-O alkyl (usually in chimeras with RNase-H dependent antisense), peptide nucleic acid (PNA), locked nucleic acid (LNA) and morpholino antisense.

Small interfering RNAs, for example, may be used to specifically reduce CDK4 and/or CDK6 translation such that the level of CDK4 and/or CDK6 polypeptide is reduced. siRNAs mediate post-transcriptional gene silencing in a sequence-specific manner. See, for example, ambion.com/techlib/hot-topics/rnai/rnai_may2002_print.html (last retrieved May 10, 2006). Once incorporated into an RNA-induced silencing complex, siRNA mediate cleavage of the homologous endogenous mRNA transcript by guiding the complex to the homologous mRNA transcript, which is then cleaved by the complex. The siRNA may be homologous to any region of the CDK4 and/or CDK6 mRNA transcript. The region of homology may be 30 nucleotides or less in length, preferable less than 25 nucleotides, and more preferably about 21 to 23 nucleotides in length. SiRNA is typically double stranded and may have two-nucleotide 3' overhangs, for example, 3' overhanging UU dinucleotides. Methods for designing siRNAs are known to those skilled in the art. See, for example, Elbashir et al. *Nature* 411: 494-498 (2001); Harborth et al. *Antisense Nucleic Acid Drug Dev.* 13: 83-106 (2003). Typically, a target site that begin with AA, have 3' UU overhangs for both the sense and antisense siRNA strands, and have an approximate 50% G/C content is selected. siRNAs may be chemically synthesized, created by in vitro transcription, or expressed from an siRNA expression vector or a PCR expression cassette. See, e.g., ambion.com/techlib/tb/tb_506html (last retrieved May 10, 2006).

When an siRNA is expressed from an expression vector or a PCR expression cassette, the insert encoding the siRNA may be expressed as an RNA transcript that folds into an siRNA hairpin. Thus, the RNA transcript may include a sense siRNA sequence that is linked to its reverse complementary antisense siRNA sequence by a spacer sequence that forms the loop of the hairpin as well as a string of U's at the 3' end. The loop of the hairpin may be of any appropriate lengths, for example, 3 to 30 nucleotides in length, preferably, 3 to 23 nucleotides in length, and may be of various nucleotide sequences including, AUG, CCC, UUCG, CCACC, CTC-GAG, AAGCUU, CCACACC and UUCAAGAGA (SEQ ID NO:7). SiRNAs also may be produced in vivo by cleavage of double-stranded RNA introduced directly or via a transgene or virus. Amplification by an RNA-dependent RNA polymerase may occur in some organisms.

An antisense inhibitory nucleic acid may also be used to specifically reduce CDK4 and/or CDK6 expression, for example, by inhibiting transcription and/or translation. An antisense inhibitory nucleic acid is complementary to a sense nucleic acid encoding a CDK4 and/or CDK6. For example, it may be complementary to the coding strand of a double-stranded cDNA molecule or complementary to an mRNA sequence. It may be complementary to an entire coding strand or to only a portion thereof. It may also be complementary to all or part of the noncoding region of a nucleic acid encoding a CDK4 and/or CDK6. The non-coding region includes the 5' and 3' regions that flank the coding region, for example, the 5' and 3' untranslated sequences. An antisense inhibitory nucleic acid is generally at least six nucleotides in length, but may be about 8, 12, 15, 20, 25, 30, 35, 40, 45, or 50 nucleotides long. Longer inhibitory nucleic acids may also be used.

An antisense inhibitory nucleic acid may be prepared using methods known in the art, for example, by expression from an expression vector encoding the antisense inhibitory nucleic acid or from an expression cassette. Alternatively, it may be prepared by chemical synthesis using naturally-occurring nucleotides, modified nucleotides or any combinations thereof. In some embodiments, the inhibitory nucleic acids are made from modified nucleotides or non-phosphodiester bonds, for example, that are designed to increase biological stability of the inhibitory nucleic acid or to increase intracellular stability of the duplex formed between the antisense inhibitory nucleic acid and the sense nucleic acid.

Naturally-occurring nucleotides include the ribose or deoxyribose nucleotides adenosine, guanine, cytosine, thymine and uracil.

Examples of modified nucleotides include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladeninje, uracil-5oxyacetic acid, butoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N-2-carboxypropyl)uracil, (acp3)w, and 2,6-diaminopurine.

Thus, inhibitory nucleic acids of the invention may include modified nucleotides, as well as natural nucleotides such as combinations of ribose and deoxyribose nucleotides, and an antisense inhibitory nucleic acid of the invention may be of any length discussed above and that is complementary SEQ ID NO:1 and/or 3.

An inhibitor of the invention can also be a small hairpin RNA or short hairpin RNA (shRNA) is a sequence of RNA that makes a tight hairpin turn that can be used to silence gene expression via RNA interference. The shRNA hairpin structure is cleaved by the cellular machinery into a siRNA, which is then binds to and cleaves the target mRNA. shRNA can be introduced into cells via a vector encoding the shRNA, where the shRNA coding region is operably linked to a promoter. The selected promoter permits expression of the shRNA. For example, the promoter can be a U6 promoter, which is useful for continuous expression of the shRNA. The vector can, for example, be passed on to daughter cells, allowing the gene silencing to be inherited. See, McIntyre G, Fanning G, *Design and cloning strategies for constructing shRNA expression vectors*, BMC BIOTECHNOL. 6:1 (2006); Paddison et al., *Short hairpin RNAs (shRNAs) induce sequence-specific silencing in mammalian cells*, GENES DEV. 16 (8): 948-58 (2002).

An inhibitor of the invention may also be a ribozyme. A ribozyme is an RNA molecule with catalytic activity and is capable of cleaving a single-stranded nucleic acid such as an mRNA that has a homologous region. See, for example, Cech, Science 236: 1532-1539 (1987); Cech, Ann. Rev. Biochem. 59:543-568 (1990); Cech, Curr. Opin. Struct. Biol. 2: 605-609 (1992); Couture and Stinchcomb, Trends Genet. 12: 510-515 (1996). A ribozyme may be used to catalytically cleave a CDK4 and/or CDK6 mRNA transcript and thereby inhibit translation of the mRNA. See, for example, Haseloff et al., U.S. Pat. No. 5,641,673. A ribozyme having specificity for a CDK4 and/or CDK6 nucleic acid may be designed based on the nucleotide sequence of SEQ ID NO:1 and/or 3.

Methods of designing and constructing a ribozyme that can cleave an RNA molecule in trans in a highly sequence specific manner have been developed and described in the art. See, for example, Haseloff et al., Nature 334:585-591 (1988). A ribozyme may be targeted to a specific RNA by engineering a discrete "hybridization" region into the ribozyme. The hybridization region contains a sequence complementary to the target RNA that enables the ribozyme to specifically hybridize with the target. See, for example, Gerlach et al., EP 321,201. The target sequence may be a segment of about 5, 6, 7, 8, 9, 10, 12, 15, 20, or 50 contiguous nucleotides selected from a nucleotide sequence having SEQ ID NO:1 and/or 3. Longer complementary sequences may be used to increase the affinity of the hybridization sequence for the target.

The hybridizing and cleavage regions of the ribozyme can be integrally related; thus, upon hybridizing to the target RNA through the complementary regions, the catalytic region of the ribozyme can cleave the target. Thus, an existing ribozyme may be modified to target a CDK4 and/or CDK6 nucleic acid of the invention by modifying the hybridization region of the ribozyme to include a sequence that is complementary to the target CDK4 and/or CDK6 nucleic acid. Alternatively, an mRNA encoding a CDK4 and/or CDK6 may be used to select a catalytic RNA having a specific ribonuclease activity from a pool of RNA molecules. See, for example, Bartel & Szostak, Science 261:1411-1418 (1993).

One example of a sequence of an shRNA that can be used to knock down CDK4 is CCGGACAGTTCGTGAGGTG-GCTTTACTCGAGTAAAGCCACCTCACGA ACT-GTTTTTT (SEQ ID NO:5). An example of an shRNA sequence that can be used to knock down CDK6 is CCGG-GACCTGGAAAGGTGCAAAGAACTCGAGTT CTTTG-CACCTTTCCAGGTCTTTTTG (SEQ ID NO:6).

Methods of Use

According to the invention, administration of CDK4 and/or CDK6 inhibitors is useful for treating cancer, particularly when used in conjunction with other chemotherapeutic agents. As described and illustrated herein, CDK4 and/or CDK6 inhibitors are cell cycle inhibitors. Targeting the cell cycle in combination with cytotoxic killing is a promising approach to rational cancer therapy. According to the invention effective control of the cell cycle, by controlling cyclin-dependent kinases CDK4 and CDK6, is a key to effective cancer treatment. By combining CDK4 and CDK6-specific inhibitors with at least one chemotherapeutic agent tumor cell proliferation is not only inhibited but cell cycle-coupled apoptosis is activated in cancer cells, including highly aggressive and intractable cancer cells such as multiple myeloma cells.

Treatment of, or treating, cancer is intended to include the alleviation of or diminishment of at least one symptom typically associated with the disease. The treatment also includes alleviation or diminishment of more than one symptom. The treatment may cure the cancer, e.g., it may substantially kill the cancer cells and/or it may arrest or inhibit the growth of the cancerous tumor. The treatment can also promote apoptosis of cancer cells. Thus, by inhibiting cell cycle progression, CDK4 and/or CDK6 inhibitors can promote a cascade of activities that leads to cellular apoptosis, particularly in cancer cells.

One aspect of the present invention is a method of treating cancer in an animal, for example, for treatment of human and veterinary animals, which includes administering to a subject animal (e.g., a human), a therapeutically effective amount of a CDK4 and/or CDK6 inhibitor, or a combination of CDK4 and/or CDK6 inhibitors. Such CDK4 and/or CDK6 inhibitors include CDK4 small molecule inhibitors, CDK6 small molecule inhibitors, CDK4 inhibitory nucleic acids, and/or CDK6 inhibitory nucleic acids.

Another aspect of the invention is a method of treating cancer in an animal which includes administering to a subject animal (e.g., a human), a therapeutically effective amount of a CDK4 and/or CDK6 inhibitor, or a combination of CDK4 and/or CDK6 inhibitors, prior to administering a chemotherapeutic agent or anti-tumor agent.

The CDK4 and/or CDK6 inhibitors are administered for a time sufficient to induce G1 arrest. Such a time needed to induce G1 arrest can be determined by immunohistochemical assay for phosphorylation of retinoblastoma (Rb) protein by CDK4/6 and Ki67 staining of cycling cells for a selected cancer type or disease. Ki67 is a molecule that can be easily detected in growing cells in order to gain an understanding of the rate at which cancer cells or the cells within a tumor are growing. Ki67 can be detected using commercially available anti-Ki67 antibodies (e.g., from Thermo Fisher Scientific) and standard immunohistochemical procedures. In general, it is believed from preliminary results that administration of CDK4 and/or CDK6 inhibitors for about three days is sufficient to induce G1 arrest for most cancer and/or tumor cell types.

In some embodiments, the CDK4 and/or CDK6 inhibitor, or a combination of CDK4 and/or CDK6 inhibitors, is administered about 9 or 10 days prior to administering a chemotherapeutic agent or anti-tumor agent. In other embodiments, the CDK4 and/or CDK6 inhibitor, or a combination of CDK4 and/or CDK6 inhibitors is administered about 8 days prior to administering a chemotherapeutic agent or anti-tumor agent. In further embodiments, the CDK4 and/or CDK6 inhibitor, or a combination of CDK4 and/or CDK6 inhibitors is administered about 7 days prior to administering a chemotherapeutic agent or anti-tumor agent. In still further embodiments, the CDK4 and/or CDK6 inhibitor, or a combination of CDK4 and/or CDK6 inhibitors is administered about 5 or 6 days prior to administering a chemotherapeutic agent or anti-tumor agent. In other embodiments, the CDK4 and/or CDK6 inhibitor, or a combination of CDK4 and/or CDK6 inhibitors is administered about 3 or 4 days prior to administering a chemotherapeutic agent or anti-tumor agent. In further embodiments, the CDK4 and/or CDK6 inhibitor, or a combination of CDK4 and/or CDK6 inhibitors is administered about 1 or 2 days prior to administering a chemotherapeutic agent or anti-tumor agent. In some embodiments, the inhibitor of CDK4 and/or CDK6 is administered from 2 to 7 days prior to the chemotherapeutic agent, or from 4 to 24 hours prior to administration of the chemotherapeutic agent.

The CDK4 and/or CDK6 inhibitor(s) (compounds and/or nucleic acids) can be administered to an animal in single or multiple doses per day over a period of time sufficient to sensitize the cancer cells to a chemotherapeutic agent. For example, the CDK4 and/or CDK6 inhibitor(s) can be administered to an animal in single or multiple doses per day over a period of from one to 180 days, or one to 150 days, or one to 120 days, or one to ninety days, or one to forty-five days, or one to thirty days, or one to twenty one days, or one to fourteen days, or one to twelve days, or one to seven days, or one to four days, or one to three days, or one to two days.

The administration of the CDK4 and/or CDK6 inhibitor(s) can be followed by administration of an chemotherapeutic agent to the animal. Alternatively, the CDK4 and/or CDK6 inhibitor(s) can be administered at the same time as the chemotherapeutic agent(s). In some embodiments, the CDK4 and/or CDK6 inhibitor(s) are administered before administering one or more chemotherapeutic agents, and then such CDK4/6 inhibitor administration is either terminated or continued during administration of one or more chemotherapeutic agent(s). In further embodiments, the CDK4 and/or CDK6 inhibitor(s) are administered before and during intermittent administration of one or more chemotherapeutic agent(s).

PD 0332991 acts reversibly. When PD 0332991 is no longer administered, cancer cells (e.g., myeloma cells) synchronously enter the S phase of the cell cycle and are sensitized to killing by low doses of chemotherapeutic agents (e.g., bortezomib) during G1/S transition. This has been shown by the inventors in myeloma cell lines in vitro and in the animal models in vivo.

In some embodiments, the CDK4 and/or CDK6 inhibitor(s) (e.g., PD 0332991) are administered on days one (1) to seven (7) days and then administration of these inhibitors is terminated. However, at about day three (3), one or more chemotherapeutic agents (e.g., bortezomib and/or dexamethasone) or radiation is periodically administered. Such administration of chemotherapeutic agents and/or radiation is continued for at least about three to about six weeks. This therapeutic regimen can be repeated. Thus, for example, after about twenty-one (21) to about forty-two (42) days, another cycle begins with administration of the CDK4 and/or CDK6 inhibitor(s) (e.g., PD 0332991) for seven (7) days and with administration of one or more chemotherapeutic agents (e.g., bortezomib and/or dexamethasone), or radiation, periodically for three to six weeks. Therefore, the chemotherapeutic agents are administered both with and without the PD 0332991 so that the chemotherapeutic agents can kill both the sensitized cells exposed to the CDK4 and/or CDK6 inhibitor(s) as well as the synchronized cells that are proceeding through the cell cycle (without CDK4 and/or CDK6 inhibitor(s)).

Treatment of, or treating, cancer is intended to include the alleviation of or diminishment of at least one symptom typically associated with the disease. The treatment also includes alleviation or diminishment of more than one symptom. The treatment may cure the cancer, e.g., it may substantially kill the cancer cells and/or it may arrest or inhibit the growth of the cancerous tumor. The treatment can also promote apoptosis of cancer cells. Thus, inhibitors of CDK4/6 actually inhibit the cascade of activities that leads to progression through the cell cycle, particularly in cancer cells where retinoblastoma (Rb) is involved in the control of the cell cycle.

Anti-cancer activity can be evaluated against varieties of cancers using methods available to one of skill in the art. Anti-cancer activity, for example, is determined by identifying the lethal dose (LD100) or the 50% effective dose (ED50) or the dose that inhibits growth at 50% (GI50) of an agent of the present invention that inhibits the growth of a cancer. In one aspect, anti-cancer activity is the amount of the agents that kills 50% or 100% of the cancer cells, for example, when measured using standard dose response methods.

The present invention also provides a method of monitoring responses to therapy and/or evaluating a therapeutically effective dosage for treating a cancer with an inhibitor of the invention. For example, dosages can be evaluated by determining the LD100 or ED50 of the agent in vitro. Such a method permits calculation of the approximate amount of agent needed per volume to inhibit cancer cell growth or to kill 50% to 100% of the cancer cells. Such amounts can be determined, for example, by standard microdilution methods.

Moreover, according to the invention, several genes are related to the cell cycle arrest and amplified apoptotic pathway related to administration of CDK4 and/or CDK6 inhibitor(s). For example, expression or activity of Noxa, BIM, MCC1, SMAC, Bak, ciap1, and/or ciap2 that can be used to monitor and evaluate responses to the therapy. These can be measured by RT-PCR, gene profiling, SNP analysis or Western blot. Another way to monitor in vivo responses to therapy this is by observing mitochondrial depolarization, using FACS and Mitotracker (a dye taken up by intact mitochondria).

The term "animal," as used herein, refers to an animal, such as a warm-blooded animal, which is susceptible to or has a disease associated with protease expression, for example, cancer. Mammals include cattle, buffalo, sheep, goats, pigs, horses, dogs, cats, rats, rabbits, mice, and humans. Also included are other livestock, domesticated animals and captive animals. The term "farm animals" includes chickens, turkeys, fish, and other farmed animals. Mammals and other animals including birds may be treated by the methods and compositions described and claimed herein. In some embodiments, the animal is a human, for example, a human patient suffering from cancer.

Another aspect of the invention is a method of inhibiting osteoclast differentiation. According to the invention, CDK4 and/or CDK6 inhibitors also inhibit osteoclast differentiation, for example, through inhibition of progenitor cell expansion. Osteoclasts are a type of bone cell that removes bone tissue by removing its mineralized matrix. Osteoclasts are normally involved in bone resorption, however, bone destruction is a key issue in metastasis to the bone in many cancers. Accordingly, by inhibiting osteoclast differentiation, the CDK4 and/or CDK6 inhibitors can inhibit metastasis of cancer cells to bone.

Thus, the invention is also directed to a method of inhibiting osteoclast differentiation in an animal by administering to the animal a therapeutically effective amount of one or more CDK4 and/or CDK6 inhibitors of the invention to thereby inhibit osteoclast differentiation.

The amount of CDK4 and/or CDK6 inhibitor administered can vary with the type of inhibitor. However, in some embodiments, the CDK4 and/or CDK6 inhibitors are used in dosages of about 1 to about 500 mg, or about 2 mg to about 400 mg, or about 5 mg to about 300 mg, or about 10 mg to about 200 mg. For example, in some embodiments, the PD 0332991 inhibitor is used in dosages of about 100 mg.

Chemotherapeutic Agents and/or Radiation

According to the invention, chemotherapeutic agents and/or radiation is administered to an animal or patient who may be suffering from cancer after administration of one or more CDK4 and/or CDK6 inhibitors. Any available chemotherapeutic agent can be used with the CDK4 and/or CDK6 inhibitors of the invention.

In some embodiments, radiation is used with or after administration of one or more CDK4 and/or CDK6 inhibitors. Thus, one aspect of the invention is a method of sensitizing cancer and/or tumor cells in a mammal to a radiation therapy comprising: administering to the mammal an inhibitor of CDK4 and/or CDK6 in an amount sufficient to arrest the cancer and/or tumor cell cycle at G1 to thereby sensitize the cancer and/or tumor cells in the mammal to radiation. After administration of one or more CDK4 and/or CDK6 inhibitors, the method involves treating the mammal with radiation for a time sufficient to inhibit growth of the cancer and/or tumor cells in the mammal.

In general, radiation therapy (or radiotherapy) is the medical use of ionizing radiation as part of cancer treatment to control the growth and spreading of malignant cells. Proton radiotherapy works by sending protons with varying kinetic energy to precisely stop at the tumor. Radiation therapy works by damaging the DNA of cells. The damage is caused by a photon, electron, proton, neutron or ion beam directly or indirectly ionizing the atoms which make up the DNA chain. Indirect ionization happens as a result of the ionization of water, forming free radicals, notably hydroxyl radicals, which then damage the DNA. In the most common forms of radiation therapy, most of the radiation effect is through free radicals. Because cells have mechanisms for repairing DNA damage, breaking the DNA on both strands proves to be the most significant technique in modifying cell characteristics. Because cancer cells generally are undifferentiated and stem cell-like, they reproduce more, and have a diminished ability to repair sub-lethal damage compared to most healthy differentiated cells. Thus, the DNA damage to cancer cells is inherited through cell division, causing them to die or reproduce more slowly.

The total dose radiation is often fractionated (spread out over time) in order to give normal cells time to recover. Fractionation regimes are highly individualized between different radiotherapy centers and even between individual doctors. In the United States, Australia, and much of Europe, the typical fractionation schedule for adults is 1.8 to 2 Gy per day, five days a week. In the northern United Kingdom, fractions are more commonly 2.67 to 2.75 Gy per day. For children, a typical fraction is 1.5 to 1.7 Gy per day, reducing the chance and severity of late-onset side effects. In some cases, two fractions per day are used near the end of a course of treatment. This schedule, known as a concomitant boost regimen or hyperfractionation, is used on tumors that regenerate more quickly when they are smaller, for example, some tumors in the head and neck.

Also, as illustrated herein, administration of chemotherapeutic agents such as proteasome inhibitors and steroids can be used in the methods of the invention. For example, bortezomib is a reversible proteasome inhibitor that is effective in treating some but not all myeloma cases. Use of CDK4 and/or CDK6 inhibitors improves the efficacy of bortezomib. Similar results are observed with the steroid dexamethasone. Bortezomib can be used in dosages of about 1 m g/m² to about 3 mg/m² human skin. The average surface area of a human is about 1 to 2 m². Therefore, in some embodiments, bortezomib is used in dosages of about 0.5 mg to about 3 mg. Dexamethasone can be used in dosages of about 1 to about 100 mg, or about 2 mg to about 50 mg, or about 5 mg to about 40 mg, or about 10 mg to about 30 mg. In some embodiments, dexamethasone is used in dosages of about 20 mg.

In addition to proteasome inhibitors and steroids, other chemotherapeutic agents can be employed with the CDK4 and/or CDK6 inhibitors of the invention. According to the invention, any chemotherapeutic agent useful for modulating, treating, killing or otherwise affecting the physiological state of a cancer or tumor cell can be used in the methods of the invention (e.g., with or after administration of one or more CDK4 and/or CDK6 inhibitors).

Examples of chemotherapeutic agents that can be used with the CDK4 and/or CDK6 inhibitors include proteasome inhibitors, mimetics of second mitochondria-derived activator of caspases (SMAC), steroids, cytotoxic agents, photosensitizing agents, folate antagonists, pyrimidine antimetabolites, purine antimetabolites, 5-aminolevulinic acid, alkylating agents, platinum anti-tumor agents, anthracyclines, DNA intercalators, epipodophyllotoxins, DNA topoisomerases, microtubule-targeting agents, vinca alkaloids, taxanes, epothilones and asparaginases. Further types of chemotherapeutic agents and information on such agent can be found in Bast et al., CANCER MEDICINE, edition 5, which is available free as a digital book. See website at ncbi.nlm.nih.gov/books/bv.fcgi?call=bv View..ShowTOC&rid=cmed.TOC&depth=2.

Proteasomes are enzyme complexes that are present in all cells and that break down intracellular proteins in a regulated manner within both healthy and cancerous cells, Intracellular proteins are involved in pathways by which cancer cells multiply, spread, interact with other cells and avoid programmed cell death. Inhibition of proteasomes by inhibitors such as bortezomib, NPI-0052 (salinosporamide A) CEP 18770 and PR-171 (carfilzomib) prevents the regulated breakdown of these intracellular proteins, thereby interfering with numerous cellular processes. This disruption of essential processes and pathways within cancer cells lead to cell death and inhibit tumor growth.

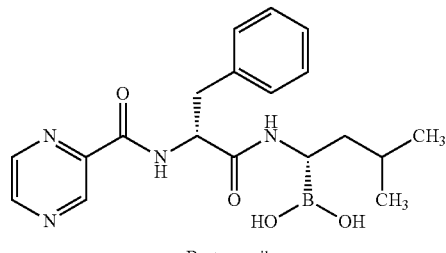

Bortezomib

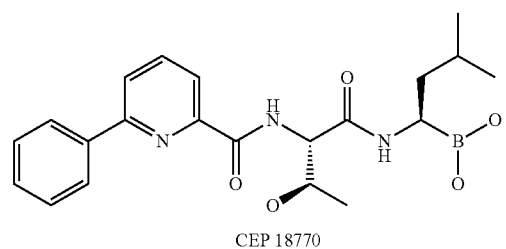

CEP 18770

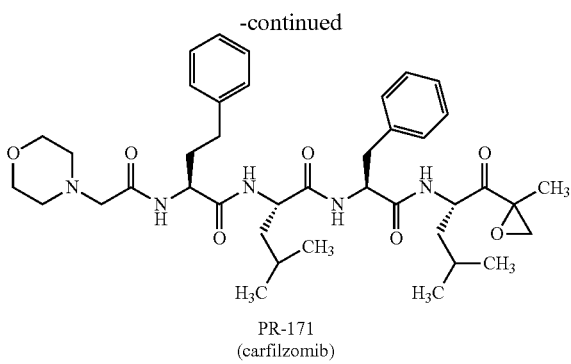

PR-171
(carfilzomib)

Second mitochondria-derived activator of caspases (Smac) promotes apoptosis via activation of caspases. Similarly, Smac mimetics also induce apoptosis in cancer cells (e.g., in multiple myeloma (MM) cells). Even cancer cells resistant to conventional and Bortezomib therapies can become vulnerable to SMAC mimetics. Examples of SMAC mimtics that can be used in the invention include compounds with the following structures.

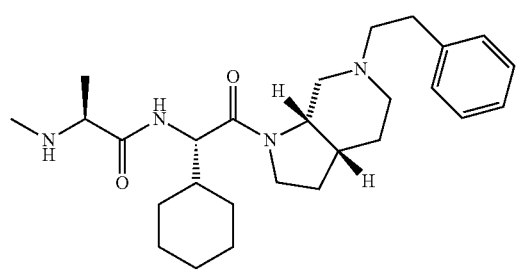

LBW242

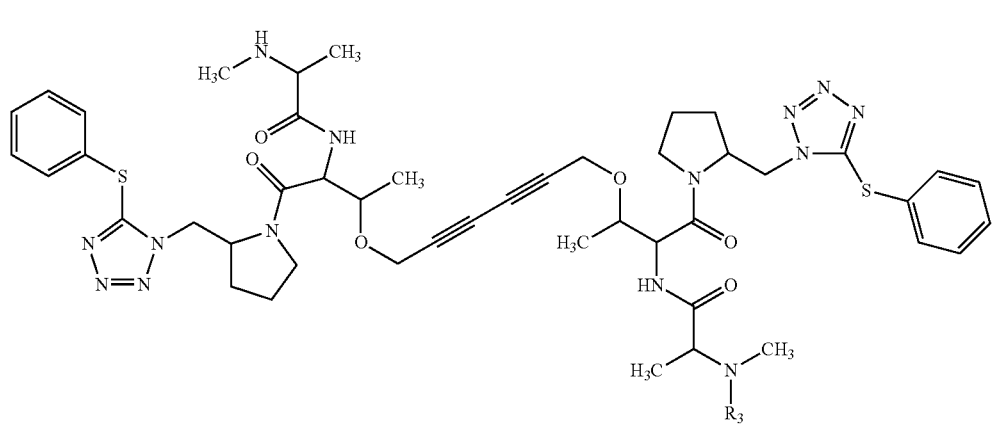

wherein R3 is hydrogen (H) or $CO_2$—$C(CH_3)_3$.

Folic acid antagonists are cytotoxic agents used as antineoplastic, antimicrobial, anti-inflammatory, and immune-suppressive agents. While several folate antagonists have been developed, and several are now in clinical trial, methotrexate (MTX) is the antifolate with the most extensive history and widest spectrum of use. MTX is often a key drug in the chemotherapy regimens used to treat patients with acute lymphoblastic leukemia, lymphoma, osteosarcoma, breast cancer, choriocarcinoma, and head and neck cancer, as well as being an important agent in the therapy of patients with non-malignant diseases, such as rheumatoid arthritis, psoriasis, and graft-versus-host disease.

Pyrimidine antimetabolites include fluorouracil, cytosine arabinoside, 5-azacytidine, and 2',2'-difluoro-2'-deoxycytidine. In some embodiments, the compositions and methods of the invention include use of cytosine arabinoside, whose structure is shown below.

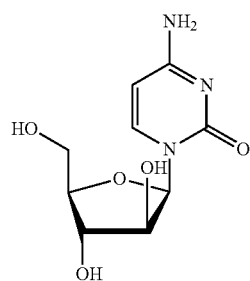

Purine antimetabolites include 6-mercatopurine, thioguanine, allopurinol (4-hydroxypyrazolo-3,4-d-pyrimidine), deoxycoformycin (pentostatin), 2-fluoroadenosine arabinoside (fludarabine; 9-β-d-arabinofuranosyl-2-fluoradenine), and 2-chlorodeoxyadenosine (Cl-dAdo, cladribine). In addition to purine and pyrimidine analogues, other agents have been developed that inhibit biosynthetic reactions leading to the ultimate nucleic acid precursors. These include phosphonacetyl-L-aspartic acid (PALA), brequinar, acivicin, and hydroxyurea.

Alkylating agents and the platinum anti-tumor compounds form strong chemical bonds with electron-rich atoms (nucleophiles), such as sulfur in proteins and nitrogen in DNA. Although these compounds react with many biologic molecules, the primary cytotoxic actions of both classes of agents appear to be the inhibition of DNA replication and cell division produced by their reactions with DNA. However, the chemical differences between these two classes of agents produce significant differences in their anti-tumor and toxic effects. The most frequently used alkylating agents are the nitrogen mustards. Although thousands of nitrogen mustards have been synthesized and tested, only five are commonly used in cancer therapy today. These are mechlorethamine (the original "nitrogen mustard"), cyclophosphamide, ifosfamide, melphalan, and chlorambucil. Closely related to the nitrogen mustards are the aziridines, which are represented in current therapy by thiotepa, mitomycin C, and diaziquone (AZQ). Thiotepa (triethylene thiophosphoramide) has been used in the treatment of carcinomas of the ovary and breast and for the intrathecal therapy of meningeal carcinomatosis. The alkyl alkane sulfonate, busulfan, was one of the earliest alkylating agents. This compound is one of the few currently used agents that clearly alkylate through an SN2 reaction. Hepsulfam, an alkyl sulfamate analogue of busulfan with a wider range of anti-tumor activity in preclinical studies, has been evaluated in clinical trials but thus far has demonstrated no superiority to busulfan. Busulfan has a most interesting, but poorly understood, selective toxicity for early myeloid precursors. This selective effect is probably responsible for its activity against chronic myelocytic leukemia (CML).

Photosensitizing agents induce cytotoxic effects on cells and tissues. Upon exposure to light the photosensitizing compound may become toxic or may release toxic substances such as singlet oxygen or other oxidizing radicals that are damaging to cellular material or biomolecules, including the membranes of cells and cell structures, and such cellular or membrane damage can eventually kill the cells. A range of photosensitizing agents can be used, including psoralens, porphyrins, chlorines, aluminum phthalocyanine with 2 to 4 sulfonate groups on phenyl rings (e.g., $AlPcS_{2a}$ or $AlPcS_4$) and phthalocyanins. Such chemotherapeutic agents become toxic when exposed to light. In one embodiment, the photosensitizing agent is an amino acid called 5-aminolevulinic acid, which is converted to protoporphyrin IX, a fluorescent photosensitizer. The structure of 5-aminolevulinic acid is shown below.

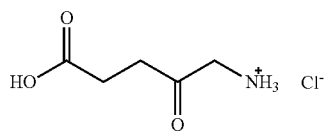

5-Aminolevulinic acid has been approved for treating skin and esophagus cancers and is in clinical trial for brain tumor detection and therapy. After administration, 5-aminolevulinic acid is generally metabolically converted to protoporphyrin IX. Light therapy is used to activate this photosensitizing agent. For example, laser treatment can be used. Alternatively, light rods can be inserted into the flesh.

Topoisomerase poisons are believed to bind to DNA, the topoisomerase, or either molecule at or near the region of the enzyme involved in the formation of the DNA protein covalent linkage. Many topoisomerase poisons, such as the anthracyclines and actinomycin D, are relatively planar hydrophobic compounds that bind to DNA with high affinity by intercalation, which involves stacking of the compound between adjacent base pairs. Anthracyclines intercalate into double-stranded DNA and produce structural changes that interfere with DNA and RNA syntheses. Two of the clinically relevant anthracyclines are shown below.

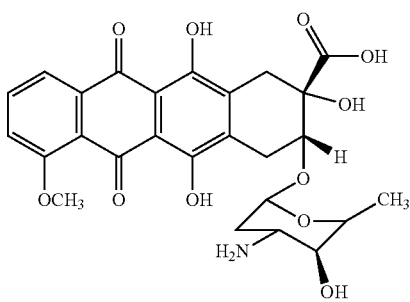

Doxorubicin

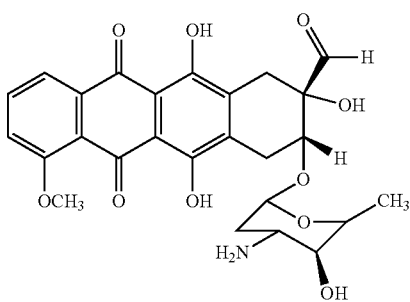

Daunorubicin

Non-intercalating topoisomerase-targeting drugs include epipodophyllotoxins such as etoposide and teniposide. Etoposide is approved in the United States for the treatment of testicular and small cell lung carcinomas. Etoposide phosphate is more water soluble than etoposide and is rapidly converted to etoposide in vivo. Other non-intercalating topoisomerase-targeting drugs include topotecan and irinotecan.

Unique classes of natural chemotherapeutic agents have been derived from plants. As distinct from those agents derived from bacterial and fungal sources, the plant products, represented by the Vinca and Colchicum alkaloids, as well as other plant-derived products such as paclitaxel (Taxol) and podophyllotoxin, do not target DNA. Rather, they either interact with intact microtubules, integral components of the cytoskeleton of the cell, or with their subunit molecules, the tubulins. Clinically useful plant products that target microtubules include the Vinca alkaloids, primarily vinblastine (VLB), vincristine (VCR), vinorelbine (Navelbine, VRLB), and a newer Vinca alkaloid, vinflunine (VFL; 20',20'-difluoro-3',4'-dihydrovinorelbine), as well as the two taxanes, paclitaxel and docetaxel (Taxotere). The structure of paclitaxel is provided below.

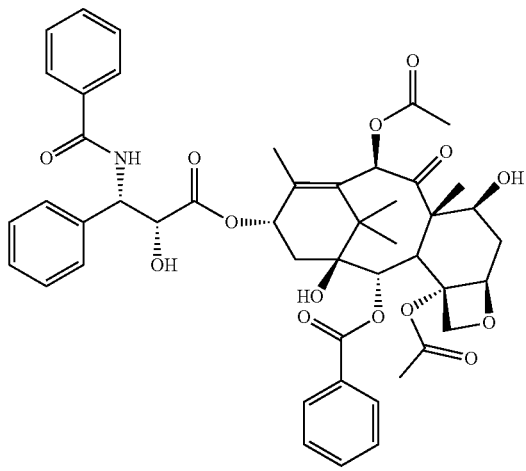 [SMILES: CC(=O)O[C@H]1C(=O)[C@@]2(C)C([C@H](OC(=O)c3ccccc3)[C@]3(O)C[C@H](OC(=O)[C@H](O)[C@@H](NC(=O)c4ccccc4)c4ccccc4)C(C)=C1C3(C)C)[C@]1(OC(C)=O)CO[C@@H]1C[C@@H]2O]

Hence, examples of chemotherapeutic agents that can be used include, but are not limited to, aldesleukin, 5-aminolevulinic acid, asparaginase, bleomycin sulfate, camptothecin, carboplatin, carmustine, cisplatin, cladribine, cyclophosphamide (lyophilized), cyclophosphamide (non-lyophilized), cytarabine (lyophilized powder), dacarbazine, dactinomycin, daunorubicin, diethylstilbestrol, doxorubicin (doxorubicin, 4'-epidoxorubicin, 4- or 4'-deoxydoxorubicin), epoetin alfa, esperamycin, etidronate, etoposide, N,N-bis(2-chloroethyl)-hydroxyaniline, 4-hydroxycyclophosphamide, fenoterol, filgrastim, floxuridine, fludarabine phosphate, fluorocytidine, fluorouracil, fluorouridine, goserelin, granisetron hydrochloride, idarubicin, ifosfamide, interferon alpha-2a, interferon alpha-2b, leucovorin calcium, leuprolide, levamisole, mechlorethamine, medroxyprogesterone, melphalan, methotrexate, mitomycin, mitoxantrone, muscarine, octreotide, ondansetron hydrochloride, oxyphenbutazone, paclitaxel, pamidronate, pegaspargase, plicamycin, salicylic acid, salbutamol, sargramostim, streptozocin, taxol, terbutaline, terfenadine, thiotepa, teniposide, vinblastine, vindesine and vincristine. Other chemotherapeutic agents and toxic effector molecules for use in the present invention are disclosed, for example, in WO 98/13059; Payne, 2003; US 2002/0147138 and other references available to one of skill in the art.

Cancers

According to the invention, the CDK4/6 inhibitors described herein are useful for treating cancer. As used herein, the term "cancer" includes solid mammalian tumors as well as hematological malignancies. The terms "tumor cell(s)" and "cancer cells(s)" are used interchangeably herein.

"Solid mammalian tumors" include cancers of the head and neck, lung, mesothelioma, mediastinum, esophagus, stomach, pancreas, hepatobiliary system, small intestine, colon, colorectal, rectum, anus, kidney, urethra, bladder, prostate, urethra, penis, testis, gynecological organs, ovaries, breast, endocrine system, skin central nervous system; sarcomas of the soft tissue and bone; and melanoma of cutaneous and intraocular origin.

The term "hematological malignancies" includes childhood leukemia and lymphomas, Hodgkin's disease, lymphomas of lymphocytic and cutaneous origin, acute and chronic leukemia, plasma cell neoplasms and cancers associated with AIDS.

In some embodiments, the cancer is associated with inactivation of the retinoblastoma gene or protein. The retinoblastoma protein (abbreviated Rb) is a tumor suppressor protein that is dysfunctional in many if not all types of cancer. Exemplary Rb protein-expressing cancers include, without limitation, all acute myelogenous leukemias (AML); acute promyelocytic leukemia (APL); all myeloproliferative disorders (MPD), including chronic myelogenous leukemia (CML), polycythemia vera, essential thrombocythemia, and idiopathic myelofibrosis; all myelodysplastic syndromes (MDS) and myelodysplastic/myeloproliferative diseases; all acute lymphoblastic leukemias (ALL), including precursor B-lymphoblastic leukemia/lymphoma and precursor T lymphoblastic leukemia/lymphoma; chronic lymphocytic leukemia (CCL); multiple myeloma (MM); monoclonal gammopathy of undetermined significance (MGUS); amyloidosis; Hodgkin lymphoma (HL), including all classical Hodgkin lymphoma cell types (e.g., Reed Sternberg cell; including nodular sclerosis, mixed cellularity and lymphocyte depleted types); all non-Hodgkin's lymphomas (NHL) including all B cell, all T cell and all NK cell types; histiocytic disorders and mastocytosis.

In addition, a cancer at any stage of progression can be treated, such as primary, metastatic, and recurrent cancers. The invention can also be used to treat autoimmune deficiency syndrome-associated Kaposi's sarcoma, cancer of the adrenal cortex, cancer of the cervix, cancer of the endometrium, cancer of the esophagus, cancer of the head and neck, cancer of the liver, cancer of the pancreas, cancer of the prostate, cancer of the thymus, carcinoid tumors, chronic lymphocytic leukemia, Ewing's sarcoma, gestational trophoblastic tumors, hepatoblastoma, multiple myeloma, non-small cell lung cancer, retinoblastoma, or tumors in the ovaries. A cancer at any stage of progression can be treated or detected, such as primary, metastatic, and recurrent cancers. Information regarding numerous types of cancer can be found, e.g., from the American Cancer Society (cancer.org), or from, e.g., Wilson et al. (1991) Harrison's Principles of Internal Medicine, 12th Edition, McGraw-Hill, Inc. Both human and veterinary uses are contemplated.

As used herein the terms "normal mammalian cell" and "normal animal cell" are defined as a cell that is growing under normal growth control mechanisms (e.g., genetic control) and that displays normal cellular differentiation and normal migration patterns. Cancer cells differ from normal cells in their growth patterns, migration and in the nature of their cell surfaces. For example cancer cells tend to grow continuously and chaotically, without regard for their neighbors, and can sometimes migrate to distal sites to generate tumors in other areas of the body.

Cell Culture Systems

The invention also provides cell culture systems and methods for assessing the resistance or sensitivity of tumor and/or cancer cells in a mammal to various chemotherapeutic agents and dosing regimens. In particular, the invention provides an ex vivo cell culture system that recapitulates a patient's tumor cell drug sensitivity and/or tumor cell drug resistance. This cell culture system includes (a) primary cancer or tumor cells isolated from the patient; (b) HS-5 or HS-27A human stromal cells; and (c) an amount of human interleukin-6 (IL-6) and human insulin-like growth factor-1 (IGF-1) effective for maintaining proliferation of the cancer or tumor cells.

This cell culture system can be used in a method for evaluating the resistance or sensitivity of tumor and/or cancer cells to chemotherapeutic agents and dosing regimens by: (a) isolating primary cancer or tumor cells from a mammal; (b) co-culturing the primary cancer or tumor cells with HS-5 or HS-27A human stromal cells to form a mixed cell culture; (c) incubating the mixed cell culture with an inhibitor of CDK4 and/or CDK6, wherein the inhibitor is present in an amount sufficient to arrest the primary cancer or tumor cells at cell cycle phase G1, to thereby form an arrested cell culture; (d) adding a test chemotherapeutic agent to the arrested cell culture to form a test culture; and (e) observing whether the cancer or tumor cells in the test culture undergo apoptosis, to thereby identify a chemotherapeutic agent effective for treatment of a cancer or tumor in a mammal.

Apoptosis can be detected using any available procedure. For example, any of the following apoptotic parameters can be detected or monitored to assess apoptosis: (i) fragmentation of DNA in populations of cells or in individual cells, in which apoptotic DNA breaks into different length pieces; (ii) alterations in membrane asymmetry; (iii) activation of apoptotic caspases; and (iv) release of cytochrome C and AIF into cytoplasm by mitochondria. Membrane asymmetry can be monitored by observing whether phosphatidylserine translocates from the cytoplasmic to the extracellular side of the cell membrane. Caspases are a family of proteases that set off a cascade of events resulting in loss of a multitude of cell functions.

In some embodiments, apoptosis can be detected using a TUNEL method according to the manufacturer's instructions (Roche, Indianapolis, Ind.).

Compositions and Formulations

In one embodiment, the invention provides a pharmaceutical composition comprising an inhibitor of CDK4 and/or CDK6. The inhibitor can be any available CDK4 and/or CDK6 inhibitor, including the small molecule inhibitors and inhibitory nucleic acids described herein. Compositions of the invention can include more than one inhibitor. Combinations of inhibitors may be used, for example, a combination of small molecule inhibitors and/or a combination of inhibitory nucleic acids. In some embodiments, both small molecule inhibitors and inhibitory nucleic acids are used in the same composition.

The inhibitors are present in the compositions in therapeutically effective amounts where the precise amount to be administered to an animal or patient will be the responsibility of the veterinarian or attendant physician. However, to achieve the desired effect(s), an inhibitor of the invention, or a combination thereof, may be administered as single or divided dosages, for example, of at least about 0.01 mg/kg to about 750 mg/kg, of at least about 0.1 mg/kg to about 500 mg/kg, at least about 1 mg/kg to about 300 mg/kg, or at least about 10 mg/kg to about 250 mg/kg of body weight, although other dosages may provide beneficial results. In some embodiments, the dosage is about 25 mg/kg to about 200 mg/kg. In other embodiments, the inhibitor of CDK4 and/or CDK6 is administered at a dosage of about 0.1 mg/Kg to about 150 mg/Kg per day, or at a dosage of about 125 mg per day.

Daily doses of the inhibitors of the invention can vary as well. Such daily doses can range, for example, from about 0.001 g/day to about 5 g/day, from about 0.005 g/day to about 2.5 g/day, from about 0.01 g/day to about 2 g/day, from about 0.025 g/day to about 8 g/day, from about 0.04 g/day to about 4 g/day, and from about 0.05 g/day to about 2 g/day. In some embodiments, the inhibitor of CDK4 and/or CDK6 is administered at a dosage of about 125 mg per day.

The absolute weight of a given inhibitor included in a unit dose can vary widely. For example, about 0.001 to about 2 g, or about 0.01 to about 1 g, of at least one inhibitor of the invention, or a plurality of inhibitors can be administered. Alternatively, the unit dosage can vary from about 0.001 g to about 2 g, from about 0.01 g to about 1 g, from about 0.1 g to about 0.5 g, from about 0.05 g to about 0.4 g, from about 0.5 g to about 0.2 g, or about 125 mg.

To prepare such a pharmaceutical composition, an inhibitor of the invention is synthesized or otherwise obtained, purified as necessary or desired, and optionally lyophilized and/or stabilized. The composition is then prepared by mixing the inhibitor with a carrier (e.g., a pharmaceutically acceptable carrier), adjusting it to the appropriate concentration and then optionally combining this composition with one or more other agents or excipients.

By "pharmaceutically acceptable" it is meant a carrier, diluent, excipient, and/or salt that is compatible with the other ingredients of the formulation, and not deleterious to the recipient thereof.

Pharmaceutical formulations containing a therapeutic inhibitor of the invention can be prepared by procedures known in the art using well-known and readily available ingredients. For example, the inhibitor can be formulated with common excipients, diluents, or carriers, and formed into tablets, capsules, solutions, suspensions, powders, aerosols and the like. Examples of excipients, diluents, and carriers that are suitable for such formulations include buffers, as well as fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatin, and polyvinyl-pyrrolidone.

Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface active agents such as cetyl alcohol and glycerol monostearate can be included. Adsorptive carriers such as kaolin and bentonite can be added. Lubricants such as talc, calcium and magnesium stearate, and solid polyethyl glycols can also be included. Preservatives may also be added. The compositions of the invention can also contain thickening agents such as cellulose and/or cellulose derivatives. They may also contain gums such as xanthan, guar or carbo gum or gum arabic, or alternatively polyethylene glycols, bentones and montmorillonites, and the like.

For oral administration, an inhibitor (e.g., a small molecule inhibitor) may be present as a powder, a granular formulation, a solution, a suspension, an emulsion or in a natural or synthetic polymer or resin for ingestion of the active ingredients from a chewing gum. The inhibitor may also be presented as a bolus, electuary or paste. The formulations may, where appropriate, be conveniently presented in discrete unit dosage forms and may be prepared by any of the methods well known to the pharmaceutical arts including the step of mixing the therapeutic agent with liquid carriers, solid matrices, semi-solid carriers, finely divided solid carriers or combinations thereof, and then, if necessary, introducing or shaping the product into the desired delivery system. The total active ingredients in such formulations comprise from 0.1 to 99.9% by weight of the formulation.

In some embodiments, the inhibitors of the invention are administered as tablets and/or capsules. For example, small molecule inhibitors are often administered as tablets or capsules. Tablets or caplets containing the inhibitors of the invention can include buffering agents such as calcium carbonate, magnesium oxide and magnesium carbonate. Caplets and tablets can also include inactive ingredients such as cellulose, pre-gelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and the like. Hard or soft gelatin capsules containing at least one inhibitor of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric-coated caplets or tablets containing one or more inhibitors of the invention are designed to resist disintegration in the stomach and dissolve in the more neutral to alkaline environment of the duodenum.

Orally administered inhibitors of the invention can also be formulated for sustained release. In this case, an inhibitor of the invention can be coated, micro-encapsulated (see WO 94/07529, and U.S. Pat. No. 4,962,091), or otherwise placed within a sustained delivery device. A sustained-release formulation can be designed to release the inhibitor, for example, in a particular part of the intestinal or respiratory tract, possibly over a period of time. Coatings, envelopes, and protective matrices may be made, for example, from polymeric substances, such as polylactide-glycolates, liposomes, microemulsions, microparticles, nanoparticles, or waxes. These coatings, envelopes, and protective matrices are useful to coat indwelling devices, e.g., stents, catheters, peritoneal dialysis tubing, draining devices and the like.

An inhibitor of the invention can also be formulated as elixirs or solutions for convenient oral administration or as solutions appropriate for parenteral administration, for instance by intramuscular, subcutaneous, intraperitoneal or intravenous routes. A pharmaceutical formulation of an inhibitor of the invention can also take the form of an aqueous or anhydrous solution or dispersion, or alternatively the form of an emulsion or suspension or salve. In some embodiments, the inhibitory nucleic acids are administered parenterally, for example, at the site of a tumor or systemically to inhibit metastasis of cancerous cells.

Thus, an inhibitor may be formulated for parenteral administration (e.g., by injection, for example, bolus injection or continuous infusion) and may be presented in unit dose form in ampoules, pre-filled syringes, small volumes infusion containers or in multi-dose containers. As noted above, preservatives can be added to help maintain the shelve life of the dosage form. The inhibitors and other ingredients may form suspensions, solutions, or emulsions in oily or aqueous vehicles, and may contain formulatory agents such as suspending, stabilizing and/or dispersing agents. Alternatively, the inhibitors and other ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable carriers, vehicles and adjuvants that are well known in the art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol," polyglycols and polyethylene glycols, $C_1$-$C_4$ alkyl esters of short-chain acids, ethyl or isopropyl lactate, fatty acid triglycerides such as the products marketed under the name "Miglyol," isopropyl myristate, animal, mineral and vegetable oils and polysiloxanes.

Other ingredients can be included such as antioxidants, surfactants, preservatives, film-forming, keratolytic or comedolytic agents, perfumes, flavorings and colorings. Antioxidants such as t-butylhydroquinone, butylated hydroxyanisole, butylated hydroxytoluene and α-tocopherol and its derivatives can also be added.

For topical administration, the inhibitors may be formulated as is known in the art for direct application to a target area. Forms chiefly conditioned for topical application take the form, for example, of creams, milks, gels, dispersion or microemulsions, lotions thickened to a greater or lesser extent, impregnated pads, ointments or sticks, aerosol formulations (e.g., sprays or foams), soaps, detergents, lotions or cakes of soap. Thus, in one embodiment, an inhibitor of the invention can be formulated as a cream to be applied topically. Other conventional forms for this purpose include wound dressings, coated bandages or other polymer coverings, ointments, creams, lotions, pastes, jellies, sprays, and aerosols. Thus, the inhibitors of the invention can be delivered via patches or bandages for dermal administration. Alternatively, the inhibitor can be formulated to be part of an adhesive polymer, such as polyacrylate or acrylate/vinyl acetate copolymer. For long-term applications it might be desirable to use microporous and/or breathable backing laminates, so hydration or maceration of the skin can be minimized. The backing layer can be any appropriate thickness that will provide the desired protective and support functions. A suitable thickness will generally be from about 10 to about 200 microns.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The inhibitors can also be delivered via iontophoresis, e.g., as disclosed in U.S. Pat. No. 4,140,122; 4,383,529; or 4,051,842. The percent by weight of a therapeutic agent of the invention present in a topical formulation will depend on various factors, but generally will be from 0.01% to 95% of the total weight of the formulation, and typically 0.1-85% by weight.

Drops, such as eye drops or nose drops, may be formulated with one or more of the inhibitors in an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The inhibitors may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; and mouthwashes comprising the composition of the present invention in a suitable liquid carrier.

The pharmaceutical formulations of the present invention may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the carriers and/or diluents that are useful in the pharmaceutical formulations of the present invention include water and physiologically acceptable buffered saline solutions such as phosphate buffered saline solutions pH 7.0-8.0.

The inhibitors of the invention can also be administered to the respiratory tract. Thus, the present invention also provides aerosol pharmaceutical formulations and dosage forms for use in the methods of the invention. In general, such dosage forms comprise an amount of at least one of the agents of the invention effective to treat or prevent the clinical symptoms of disease (e.g., cancer). Any statistically significant attenuation of one or more symptoms of the disease (e.g., cancer) treated pursuant to the methods of the present invention is considered to be a treatment of such disease within the scope of the invention.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g., gelatin or blister packs from which the powder may be administered orally or with the aid of an inhalator, insufflator, or a metered-dose inhaler (see, for example, the pressurized metered dose inhaler (MDI) and the dry powder inhaler disclosed in Newman, S. P. in *Aerosols and the Lung*, Clarke, S. W. and Davia, D. eds., pp. 197-224, Butterworths, London, England, 1984).

Inhibitors of the present invention can also be administered in an aqueous solution when administered in an oral, aerosol or inhaled form. Thus, other aerosol pharmaceutical formulations may comprise, for example, a physiologically acceptable buffered saline solution containing between about 0.1 mg/mL and about 100 mg/mL of one or more of the inhibitors of the present invention specific for the indication or disease (e.g., cancer) to be treated. Dry aerosol in the form of finely divided solid inhibitor or nucleic acid particles that are not dissolved or suspended in a liquid are also useful in the practice of the present invention. Inhibitors of the present invention may be formulated as dusting powders and comprise finely divided particles having an average particle size of between about 1 and 5 µm, alternatively between 2 and 3 µm. Finely divided particles may be prepared by pulverization and screen filtration using techniques well known in the art. The particles may be administered by inhaling a predetermined quantity of the finely divided material, which can be in the form of a powder. It will be appreciated that the unit content of active ingredient or ingredients contained in an individual aerosol dose of each dosage form need not in itself constitute an effective amount for treating the particular infection, indication or disease since the necessary effective amount can be reached by administration of a plurality of dosage units. Moreover, the effective amount may be achieved using less than the dose in the dosage form, either individually, or in a series of administrations.

For administration to the upper (nasal) or lower respiratory tract by inhalation, the inhibitors of the invention are conveniently delivered from a nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Nebulizers include, but are not limited to, those described in U.S. Pat. Nos. 4,624,251; 3,703,173; 3,561,444; and 4,635,627. Aerosol delivery systems of the type disclosed herein are available from numerous commercial sources including Fisons Corporation (Bedford, Mass.), Schering Corp. (Kenilworth, N.J.) and American Pharmoseal Co., (Valencia, Calif.). For intra-nasal administration, the therapeutic inhibitory agent may also be administered via nose drops, a liquid spray, such as via a plastic bottle atomizer or metered-dose inhaler. Typical of atomizers are the Mistometer (Wintrop) and the Medihaler (Riker).

An inhibitor of the invention may also be used in combination with one or more known therapeutic agents, for example, a pain reliever; a vitamin; an antioxidant; an antibacterial agent; an anti-cancer agent; an anti-inflammatory agent; an antihistamine; a bronchodilator and appropriate combinations thereof, whether for the conditions described herein or some other condition.

Kits and Articles of Manufacture

In one embodiment, the invention provides an article of manufacture that includes a pharmaceutical composition containing an inhibitor of the invention for any of the uses and methods of the invention. Such articles may be a useful device such as a sustained release device, bandage, transdermal patch or a similar device. The device holds a therapeutically effective amount of a pharmaceutical composition. The device may be packaged in a kit along with instructions for using the pharmaceutical composition for any of the uses or methods described herein. The pharmaceutical composition includes at least one inhibitor of the present invention, in a therapeutically effective amount such that the use or method is accomplished.

Another aspect of the invention is a kit that includes a composition containing an inhibitor of the invention packaged in a kit along with an anti-cancer agent and instructions for using the pharmaceutical composition and the chemotherapeutic agent for any of the uses or methods described herein.

Unique Features of the Invention

One aspect of the invention is a combination therapy that inhibits (i.e., substantially prevents) tumor cell replication and induces synergistic killing of tumor cells. This combination therapy is accomplished by prolonged inhibition of CDK4 and CDK6 to induce G1 cell cycle arrest, followed by treatment with a chemotherapeutic agent/cytotoxic agent or radiation in the presence of the CDK4 and CDK6 inhibitor. By prolonging the inhibition of CDK4/6 and G1 arrest before addition of a chemotherapeutic or cytotoxic drug, a combination therapy has been invented that sensitizes cancer cells (e.g., primary myeloma cells and clonal human myeloma cell lines (HMCLs)) to killing by the chemotherapeutic or cytotoxic agent. Such methods are effective even when the cancer cells (e.g. myeloma cells) are resistant to cytotoxic and/or chemotherapeutic agents (for example, bortezomib or dexamethasone).

The invention identifies the optimal order and timing of addition of the CDK inhibitor and the chemotherapeutic agent or radiation that maximize the killing of multiple myeloma cells. Thus, inhibitors of CDK4 and/or CDK6 are employed prior to administration or addition of the chemotherapeutic or cytotoxic agent.

Another aspect of the invention involves induction of synchronous S phase entry by cancer and/or tumor cells. This method comprises inhibition of CDK4 and CDK6 with induction of G1 arrest followed by release of CDK4 and CDK6 inhibition, which lead to synchronous S phase entry. Cancer and tumor cells become particularly vulnerable to chemotherapeutic and cytotoxic agents upon entry into S phase. Work by the inventors indicates that this method leads to synchronous S phase entry by about 70% of human myeloma cell lines and greater than 82% of human mantle cell lymphoma cell lines. This is the first demonstration that selective inhibition of CDK4 and CDK6 can lead to effectively synchronous S phase entry. According to the invention, this is the most effective method for induction of synchronous S phase entry.

This combination therapy induces synergistic killing of tumor cells by inducing synchronous S phase entry following the release of G1 arrest induced by inhibition of CDK4 and CDK6, and preferential killing of tumor cells that are in the S phase of the cell cycle. By induction of synergistic killing, this combination therapies sensitize drug-resistant primary myeloma cells to killing by the same drug, to which they were previously insensitive. This is accomplished by pretreatment with one or more inhibitors of CDK4 and CDK6. The combination therapies can also sensitize drug resistant myeloma cells to killing by an alternative cytotoxic agent, for example killing primary myeloma cells resistant to the combination of PD 0332991/bortezomib by PD 0332991/NPI-0052, PD 0332991/PR-171 or by PD 0332991/dexamethasone.

Moreover, the combination therapies kill myeloma cells at doses of cytotoxic agent that are substantially lower than those used when the cytotoxic agent is used as a single agent. Even though two potentially cytotoxic agents (or a cytotoxic agent and radiation) are used, the combination therapy still reduces cytotoxic side effects.

The combination therapies also preferentially target cycling tumor cells and induces synergistic tumor suppression in human myeloma NOD/SCID mouse xenograft models without significant side effects in the host mice.

The combination therapies induce synergistic killing of human myeloma cells by induction of preferential release of the second mitochondria activator of caspase (SMAC), mitochondria depolarization and caspase activation.

Another aspect of the invention is a combination therapy which combines the inhibition of CDK4 and CDK6 (e.g., using PD 0332991) with small molecule inhibitors that selectively target the apoptotic pathway identified in this invention, such as XIAP and the release of cytochrome C.

Examples of cancers/tumors that can be effectively treated by inducing synchronous S phase entry following the release of G1 arrest (induced by the inhibition of CDK4 and CDK6) include a variety of Rb-expressing and primary hematological cancers. For example, tumors and cancers that can be treated by this method include but not limited to multiple myeloma, Walderstrom's macroglobulinemia, lymphoma (mantle cell lymphoma, Burkett's lymphoma, diffused large B cell lymphoma) and leukemia.

In some embodiments, the methods of the invention also involve determining cell cycle gene signatures as biomarkers for blood cancers by induction of synchronous S phase entry and analysis of the types of genes expressed and time course of their gene expression profile. Such analysis of gene expression can be evaluated, for example, by microarray gene expression analysis and real time RT-PCR.

According to the invention, methods involving such combination therapy can be used to control relapse of solid tumors and to suppress the progression of all cancers that have metastasized or can metastasize to the bone.

While not wishing to be limited to one mechanism of action, it is believed that the combination therapies of the invention effectively kill primary myeloma cells by overriding the protection from bone stromal cells.

Another aspect of the invention is to use this combination therapy to inhibit cell cycle reentry and expansion of cancer stem cells.

Another aspect of the invention is a method for assessing cancer/tumor cell drug sensitivity or drug resistance. This method involves first co-culturing a patient's primary cancer cells from the bone marrow with a HS-5 human stromal cell line in the presence of cytokines (human IL-6) and growth factor (human IGF-1). For plasma cell neoplasms, such as multiple myeloma, these cells would be CD138 positive cells, for other hematological malignacies, the bone marrow cells to co-culture with the HS-5 cell line would carry, and be selectable by cell surface markers (e.g., as shown in the Examples). Then this culture is incubated with a CDK4/CDK6 inhibitor to keep these cells in G1. Next, a test chemotherapeutic agent or a test dosage of a chemotherapeutic agent is added to the culture, and the amount of cell death or cell survival of the cells carrying the hematological cell marker of the cancer being studied in the culture is determined. Different types and combinations of chemotherapeutic agents can be tested as well as different amounts of chemotherapeutic agents. Use of this culture system and these methods permits one of skill in the art to determine optimal therapeutic regimens for treatment of cancer. Thus, the inventors have invented the first ex vivo cell culture system that recapitulates tumor cell drug sensitivity and resistance in the patient. CD138 is a cell surface marker of plasma cells and malignant myeloma cells. Human interleukin 6 (IL-6) and human insulin-like growth factor-1 (IGF-1) are available from R&D systems (catalog nos. 206-IL and 291-G1-050, respectively; Minneapolis, Minn.).

Uses of the Invention

The invention can be used to treat multiple myeloma patients for example, during aggressive tumor growth or relapse by targeting cell division and induction of synergistic tumor killing using the combination therapy, for example, using a combination of PD 0332991 with bortezomib, or PD 0332991 with dexamethasone.

The invention can be used to predict in advance which myeloma patient will respond to a specific combination therapy and which specific combination will benefit a specific patient by testing the tumor cells isolated from patients in the co-culture system ex vivo for only 3-7 days.

The invention can be used to select in advance the optimal cytotoxic agent for controlling myeloma progression for each myeloma patient using this combination therapy and the co-culture system.

The invention involves application of a combination therapy as an intervention for a variety of Rb-expressing and hematopoietic/blood cancers characterized by uncontrolled cell division. Typically, such uncontrolled cell division occurs during drug resistance and aggressive tumor growth. The cancers include, but are not limited to, mantle cell lymphoma, diffused large B cell lymphoma, acute myeloid leukemia, chronic lymphatic leukemia, chronic myelocytic leukemia, polycythemia vera, malignant lymphoma, multiple myeloma, Hodgkin's lymphoma, non-Hodgkin's lymphoma or combinations thereof.

The invention is also useful for inhibiting, controlling and treating the relapse of solid tumors and to suppress the progression of all cancers that may metastasize to the bone.

The invention can be used to develop combination therapy in which inhibition of CDK4/6 with PD 0332991 is combined with drugs that selectively target the apoptotic pathway identified in this invention, such as SMAC.

The invention is further illustrated by the following non-limiting Examples.

Example 1

Experimental Procedures

This Example describes some of the materials and methods used in developing the invention.

Isolation of Primary Bone Marrow Myeloma Cells and Cell Culture

Bone marrow specimens were obtained from multiple myeloma patients at the New York-Presbyterian Hospital under informed consent as part of an Institutional Review Board approved study. Primary CD138+ human BM myeloma (BMM) cells were isolated as previously described (Baughn et al., 2006) from the patients described in Table 1.

TABLE 1

Clinical information of myeloma cases in this study.

| MM # | Age | Dx | Stage | Ig Isotype | Prior Tx |
|------|-----|------|-------|------------|----------|
| 1  | 59 | MM   | III | Gκ | Y   |
| 2  | 43 | MM   | II  | 'κ | Y** |
| 3  | 46 | MGUS | 0   | Gκ | N   |
| 4  | 36 | MM   | III | Gκ | Y*  |
| 5  | 57 | MM   | III | 'κ | Y*  |
| 6  | 44 | MM   | III | Gκ | Y   |
| 7  | 55 | MM   | III | Gκ | N   |
| 8  | 63 | MM   | III | 'κ | Y   |
| 9  | 60 | MM   | III | Gκ | Y*  |
| 10 | 55 | MM   | III | Gκ | Y   |
| 13 | 72 | MM   | III | Aκ | Y   |
| 14 | 82 | MM   | III | Gλ | N   |
| 15 | 44 | MM   | II  | 'λ | N   |
| 16 | 68 | MM   | II  | Gλ | Y   |

BMM cells were co-cultured, at a 2:1 ratio with mitomycin C-arrested HS-5 stromal cells (ATCC, Manassas, Va.). For analysis, BMM cells were removed from stromal cells by gentle pipetting. The purity of the BMM cells was determined to be >96% by staining with a PE-conjugated anti-human CD138 mouse mAb (Invitrogen, Carlsbad, Calif.).

MM1.S and MM1.R human myeloma cell lines (HMCLs) are described in Greenstein et al. (Exper. Hematol. 31: 271-282 (2003)). Cells were treated with PD 0332991 (2 µM for BMM cells and 0.25 µM for HMCLs, unless stated otherwise) (Pfizer, San Diego, Calif.), bortezomib (Millennium Pharmaceuticals, Inc. Cambridge, Mass.), or dexamethasone (Sigma, St. Louis, Mo.) at concentrations and for times indicated. To induce phosphorylation of Stat3, cells were cultured in the presence of 5 ng/ml recombinant human IL-6 (PeproTech, Rocky Hill, N.J.). Cell viability was determined by trypan blue exclusion and presented as percentage of the starting number of cells (% input). The surface expression of IL-6Ra and gp130 was detected with PE-conjugated anti-human CD126 (Immunotech, Marseille, France) and gp130 (R&D, Minneapolis, Minn.) mouse mAbs. Activated caspase-8 was stained by using a CaspGLOW™ red active caspase-8 staining kit (MBL, Woburn, Mass.) and analyzed using a FACS-Calibur and Cell Quest (BD Biosciences, San Jose, Calif.) and the FloJo software (TreeStar, San Carlos, Calif.).

Analysis of BrdU-Uptake and DNA Content

Cells were incubated with 5-bromo-2-deoxyuridine (BrdU, 5 µg/ml; Sigma) at 37° C. for 30 min (HMCLs) or 16 h (BMM cells). Cells were fixed with 70% ethanol overnight at 4° C., incubated with 0.4 mg/ml pepsin for 20 min at room temperature and 2N HCl for 10 min at 37° C. Samples were washed with 50 mM sodium borate (pH 8.5) and then 0.1% BSA/PBS. To detect BrdU, cells were incubated with a FITC-conjugated anti-BrdU mouse mAb (Roche Diagnostics, Pleasanton, Calif.) for 30 min at room temperature. For DNA content analysis, cells were incubated further with 50 µg/ml propidium iodide and 100 U/ml ribonuclease A (Sigma) for 30 min at 37° C. Samples were analyzed by flow cytometry.

Detection of Mitochondrial Membrane Depolarization

To detect mitochondrial membrane depolarization (MMD), cells were incubated with 66 nM MitoProbe™ JC-1 or 33 nM MitoTracker Red CMXRos (Invitrogen) for 30 min at 37° C. and re-suspended in PBS for FACS analysis. To detect cell death 2 nM To-Pro-3 (Invitrogen) was added just before acquisition.

RNA Interference

To knock down Bim expression, MM1.S cells were transfected with 100 nM Bim siRNA using a SIGNALSILANCE® Bim siRNA Kit (Cell Signaling Technology, Danvers, Mass.) following the manufacturer's instructions. To knock down CDK4 and CDK6 or gp130, MM1.S cells were transduced simultaneously with CDK4 TRCN0000000520 and CDK6 TRCN0000039744, or with gp130 TRCN0000058283 (283), 284, 286 MISSION® shRNA lentiviral transduction particles (Sigma), following the manufacturer's instructions. The MISSION® non-target shRNA lentiviral transduction particles were used as a control. Knockdown of Bim, CDK4 and CDK6 was validated by immunoblotting and expression of surface gp130 was determined by FACS analysis, at 72 h post-transfection.

The sequence of shRNA that was used to knock down CDK4 is CCGGACAGTTCGTGAGGTGGCTTTA CTCGAGTAAAGCCACCTCACGAACTG TTTTTT (SEQ ID NO:5), and the sequence of shRNA that was used to knock down CDK6 is CCGGGACCTGGAAAGGTGCAAAGAA CTCGAGTTCTTTGC ACCTTTCCAGGTCTTTTG (SEQ ID NO:6).

Quantitative RT-PCR

Total RNA was isolated using the TRIzol reagent (Invitrogen). The first strand cDNA was synthesized using SuperScript 111 (Invitrogen) and subjected to real-time RT-PCR using the Assays-on-Demand gene expression mixes specific for human Noxa, Bim, Mcl-1, Bcl2, TRAIL, Rb or β-actin, and the TaqMan Universal PCR Master Mix (Applied Biosystems, Foster City, Calif.). Reactions were carried out in triplicate in the ABI PRISM 7900 HT Sequence Detection System. The relative amount of products was determined by the comparative Ct method according to the manufacturer's instructions.

Immunoblotting and Immunoprecipitation

Viable cells were obtained by Ficoll density centrifugation (GE Healthcare, Piscataway, N.J.). Cytosolic and mitochondrial fractions were isolated as described (Yang et al., 1997). Whole cells or purified mitochondria were lysed in a buffer containing 10 mM Tris-HCl, pH 7.5, 150 mM NaCl, 5 mM EDTA, 1% Triton X-100, and protease inhibitors. For detection of phosphorylated Stat3, cells were lysed in a buffer containing 20 mM Tris, pH 7.5, 150 mM NaCl, 1 mM EDTA, 1 mM EGTA, 1% Triton X-100, 2.5 mM sodium pyrophosphate, 1 mM β-glycerophosphate, 1 mM $Na_3VO_4$, and protease inhibitors. Immunoblotting was performed as described in Huang et al. (2004). The primary antibodies used are summarized in Table 2. Signals were developed with the SuperSignal West Femto Maximum Sensitivity Substrate (Pierce Biotechnology, Rockford, Ill.).

TABLE 2

Antibodies used in immunoblotting and immunoprecipitations.

| Antibody | Source | Species | Clone; Cat.# | Isotype |
|----------|--------|---------|--------------|---------|
| Cyclin D2 (M20) | Santa Cruz | Rabbit | sc-593 | IgG |
| p27 (C-19) | Santa Cruz | Rabbit | sc-528 | IgG |
| Phospho-Stat3 | Cell Signaling | Mouse | #9138 | IgG1 |
| Stat3 | Upstate | Rabbit | #06-596 | |
| Noxa | Alexis Biochemicals | Mouse | 114C307.1; #ALX804408 | IgG1 |
| Bim | Alexis Biochemicals | Rat | 3C5; #ALX804527 | IgG2aκ |
| Bim | Cell Signaling | Rabbit | #4582 | |
| Bid | Cell Signaling | Rabbit | #2002 | |
| Puma | Cell Signaling | Rabbit | #4976 | |

TABLE 2-continued

Antibodies used in immunoblotting and immunoprecipitations.

| Antibody | Source | Species | Clone; Cat.# | Isotype |
|---|---|---|---|---|
| Bak | Sigma | Rabbit | #B5897 | IgG |
| Bak (TC-100) | Calbiochem | Mouse | #AM03T | IgG2a |
| Bax | Cell Signaling | Rabbit | #2772 | |
| Bcl-2 | DakoCytomation | Mouse | 124; M0887 | IgG1 |
| Bcl-2 | Cell Signaling | Rabbit | #2876 | |
| Bcl-XL | Cell Signaling | Rabbit | #2762 | |
| Bcl-XL | SouthernBiotech | mouse | 7B2.5; #10030-01 | IgG3 |
| Mcl-1 | Santa Cruz | Rabbit | sc-819 | IgG |
| Smac | Cell Signaling | Mouse | #2954 | IgG1 |
| Cytochrome c | Cell Signaling | Rabbit | #4272 | IgG |
| XIAP | Cell Signaling | Rabbit | #2045 | IgG |
| c-IAP1 | Cell Signaling | Rabbit | #4952 | |
| c-IAP2 | Cell Signaling | Rabbit | #3130 | |
| Caspase-9 | Cell Signaling | Rabbit | #9502 | |
| Caspase-8 | Cell Signaling | Mouse | #9746 | IgG1 |
| PARP | BD Pharmingen | Mouse | #65196E | Ascite |
| Hsp60 | BD Biosciences | Mouse | #611562 | IgG1 |
| Tubulin | Cell Signaling | Rabbit | #2144 | |
| Actin | Santa Cruz | Rabbit | sc-1615-R | IgG |
| p44/p42 | Cell Signaling | Rabbit | #9102 | |
| Phospho-p44/42 | Cell Signaling | Mouse | #9106 | |
| JNK1/2 | Cell Signaling | Rabbit | #9258 | |
| Phospho-JNK1/2 | Cell Signaling | Mouse | #9255 | IgG1 |
| IκB-α | Santa Cruz | Rabbit | sc-371 | |
| Phospho-IκBα | Cell Signaling | Mouse | #9246 | |

For immunoprecipitation, lysate (50 µg of protein) was precleared with 20 µl of Protein G PLUS-agarose beads (Santa Cruz Biotechnology, Santa Cruz, Calif.) and incubated with rabbit anti-Bim, anti Bcl-XL (Cell signaling Technology), anti-Mcl1 (Santa Cruz), anti-Bak (Sigma) or mouse anti-Bcl-2 (DakoCytomation, Carpinteria, Calif.) overnight at 4° C. The immunocomplexes were collected by incubation with Protein G PLUS-agarose beads (Santa Cruz) and centrifugation. These immunocomplex samples were then analyzed by immunoblotting. The primary antibodies used in immunoblotting are as summarized in Table 2.

Signals were developed with the SuperSignal West Femto Maximum Sensitivity Substrate (Pierce Biotechnology, Rockford, Ill.). Samples were then washed in lysis buffer and immunoblotted with specific antibody against Bim, Mcl-1, Bcl-2, Bcl-XL or Bak.

Myeloma Xenograft Model and Therapy

MM1.S cells ($1 \times 10^7$) stably expressing the HSV-TK-eGFP-luciferase fusion protein were injected intravenously to NOD/SCID (NOD/LTSZPrko/J) mice (Jackson Laboratories, Bar Harbor, Me.) at 8-9 weeks of age as described (Wu et al., 2005). The tumor distribution was followed by serial whole-body noninvasive imaging of visible light emitted by luciferase-expressing myeloma cells upon injection of mice with luciferin. Mice with established disseminated MM were divided into 4 cohorts, with statistically equivalent tumor burden evaluated by bioluminescence imaging between cohorts. PD 0332991 was dissolved in vehicle (50 mM sodium lactate, pH 4.0) and administered daily at 80 mg/kg or 150 mg/kg by gavage for time indicated. Bortezomib (0.25 mg/kg) was administered intravenously. The control mice received the vehicle through the same route.

Statistical Analysis

All statistical analyses were performed by using the Student's t-test, and significance was set at $p < 0.05$.

Example 2

Cell Cycle Inhibition Facilitates Cancer Cell Death

This Example illustrates two novel strategies to arrest the cell cycle and prime myeloma cells for cytotoxic killing.

Inhibition of CDK4 and CDK6 Primes Myeloma Cells for Cytotoxic Killing by Inducing G1 Arrest or Synchronous S Phase Entry Inhibition of CDK4 and CDK6 by PD 0332991 leads to exclusive G1 arrest unaccompanied by apoptosis in primary CD138+ human BM myeloma (BMM) cells and human myeloma cell lines (HMCLs) (Baughn et al., 2006). However, the inventors hypothesized that sustained G1 arrest may perturb cell cycle-coupled cellular function, thereby sensitizing cycling myeloma cells to cytotoxic killing. PD 0332991 acts reversibly. Therefore, the inventors further hypothesized that release of the G1 block may lead to a synchronous G1-S transition and also heighten the sensitivity to cytotoxic agents.

Figure 1B:
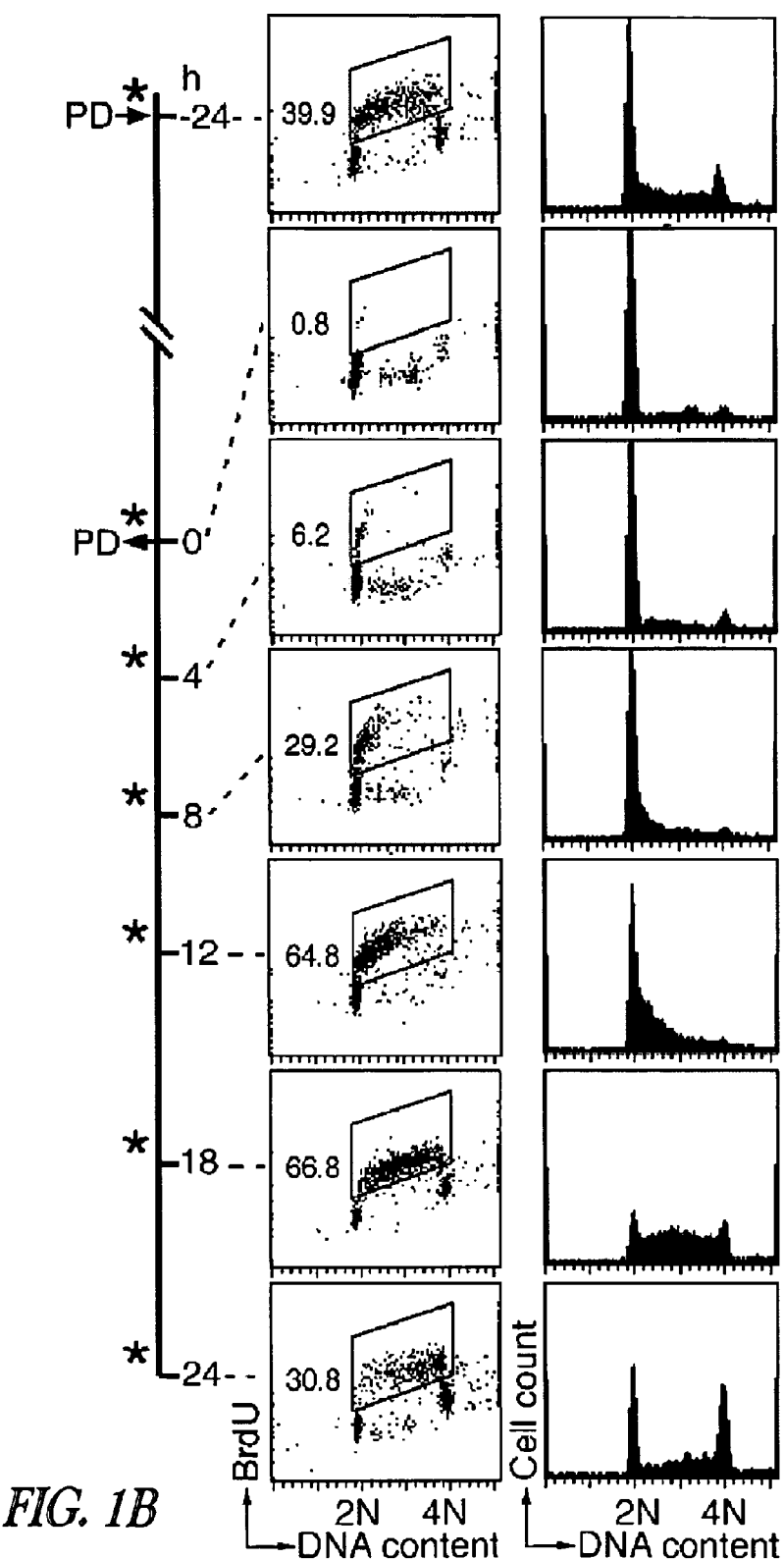
Figure 1C:
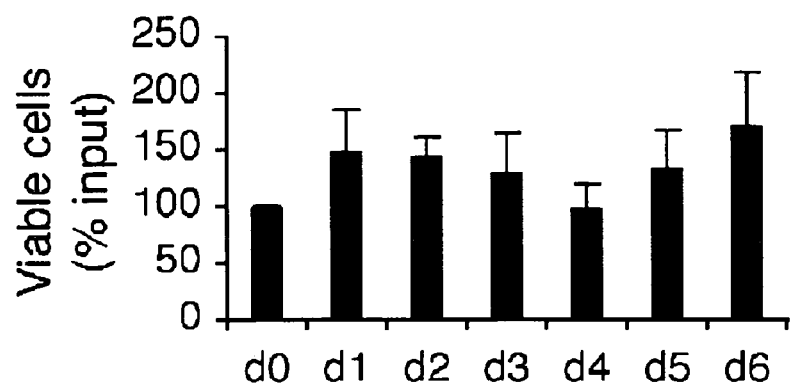
Figure 1D:
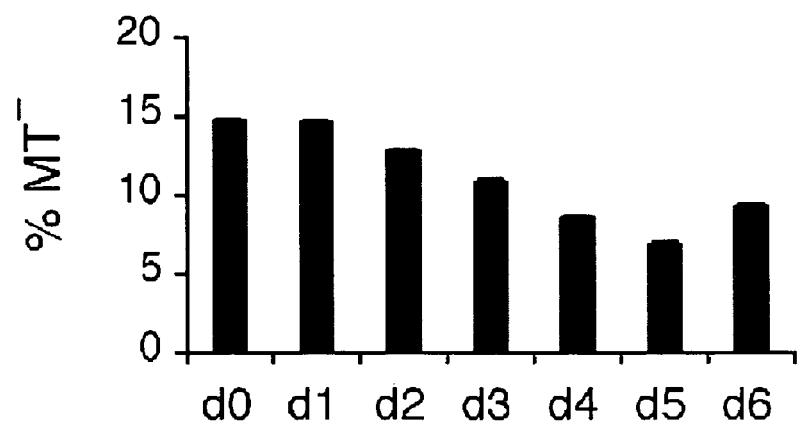
Figure 1E:
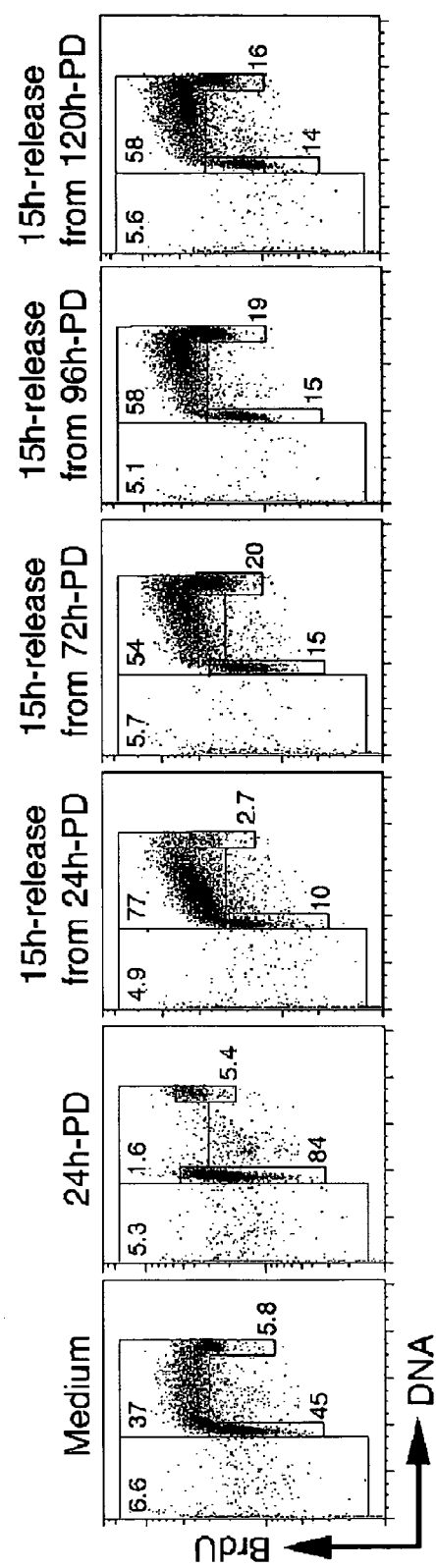

To address these possibilities, a complete G1 arrest was induced with PD 0332991 (0.25 µM) in HMCLs, including MM1.S, as depicted in FIG. 1A. Four hours after PD 0332991 removal (wash-out), the cells began to enter S phase as determined by simultaneous analyses of BrdU-uptake (30 minutes) and DNA content per cell. The cells progressed synchronously through the cell cycle, leading to a sharp increase in the proportion of cells in S phase, to 65% by 12 hours and 67% by 18 hours with some progressing to G2 (FIG. 1B). Induction of G1 arrest and synchronous S phase entry by PD 0332991 was maintained in the absence of apoptosis for at least 6 days, reinforcing the exceptional selectivity and reversibility with which PD 0332991 inhibits CDK4/6 and cell cycle progression through G1 (FIG. 1C-E).

To determine whether cytotoxic killing is coupled to the cell cycle, myeloma cells were treated with bortezomib at high dose at various times after PD 0332991 removal.

To determine whether cytotoxic killing is coupled to the cell cycle, myeloma cells were treated with bortezomib at high doses for one hour at various times after PD 0332991 removal. Note that bortezomib is also called Velcade and is available from Millennium Pharmaceuticals. The structure of Bortezomib is shown below.

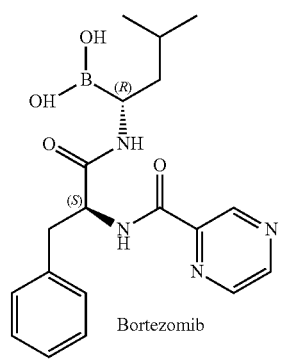

Bortezomib

Bortezomib is a general proteasome inhibitor that has anti-cancer activity in diverse cancers and has previously been used at dosages associated with toxicity. Its exact molecular mechanism of action was previously not known, due to the pleiotrophic effects of a generalized inhibition of proteasome function.

Figure 1F:
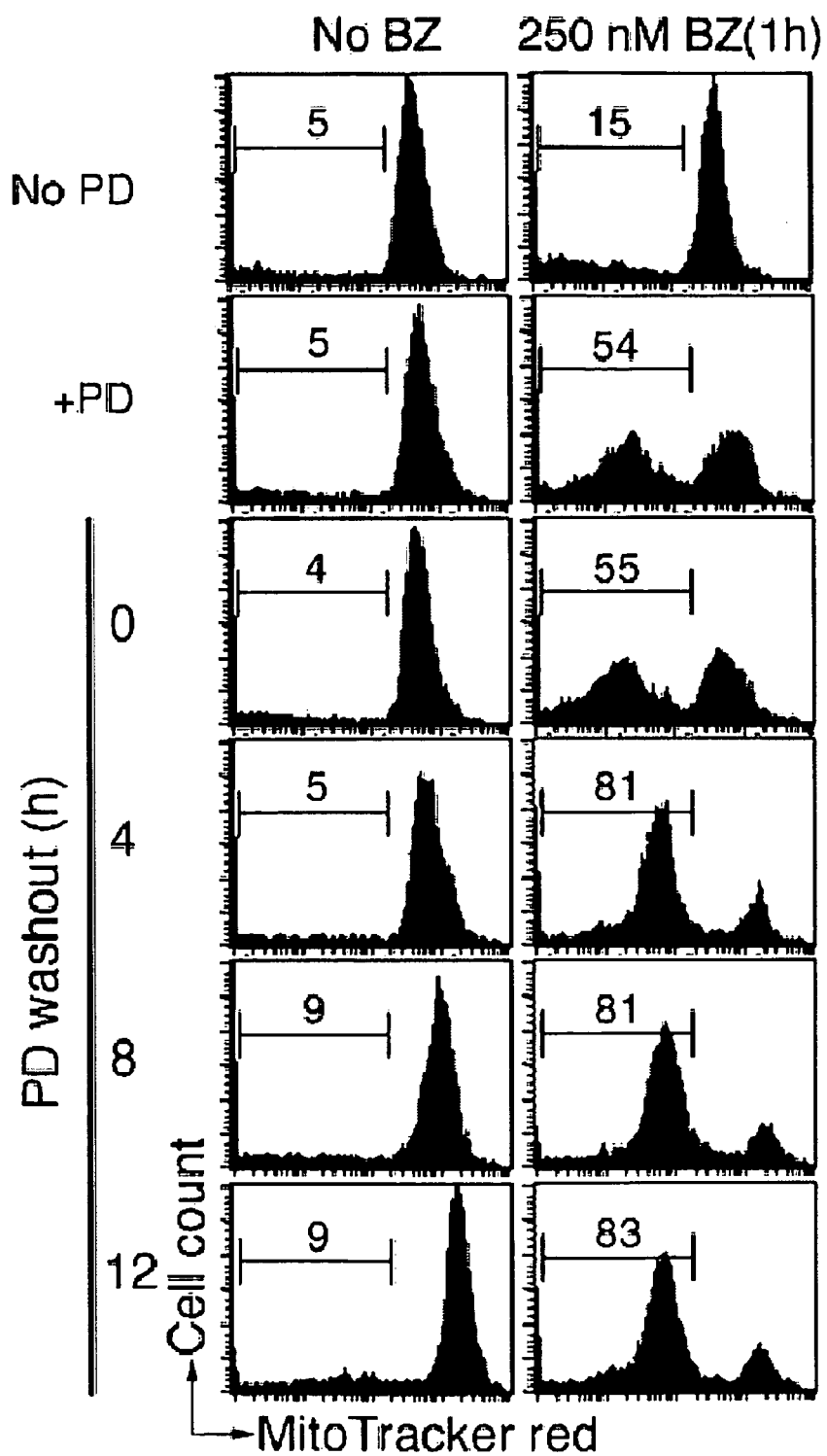
Figure 1G:
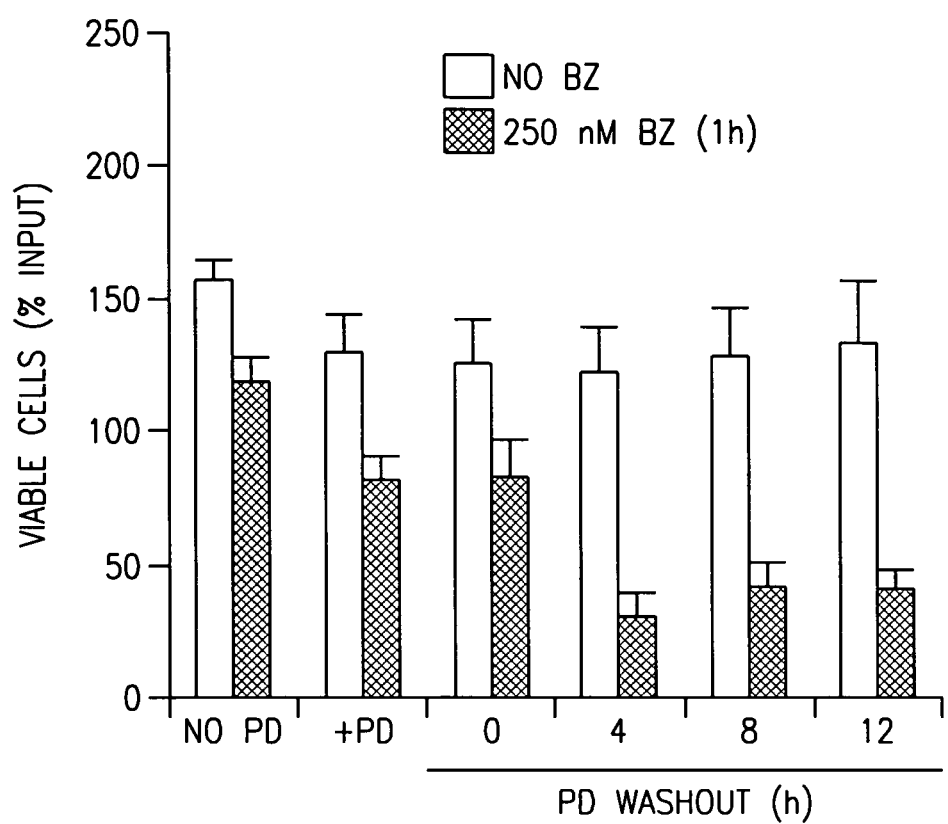
Figure 1H:
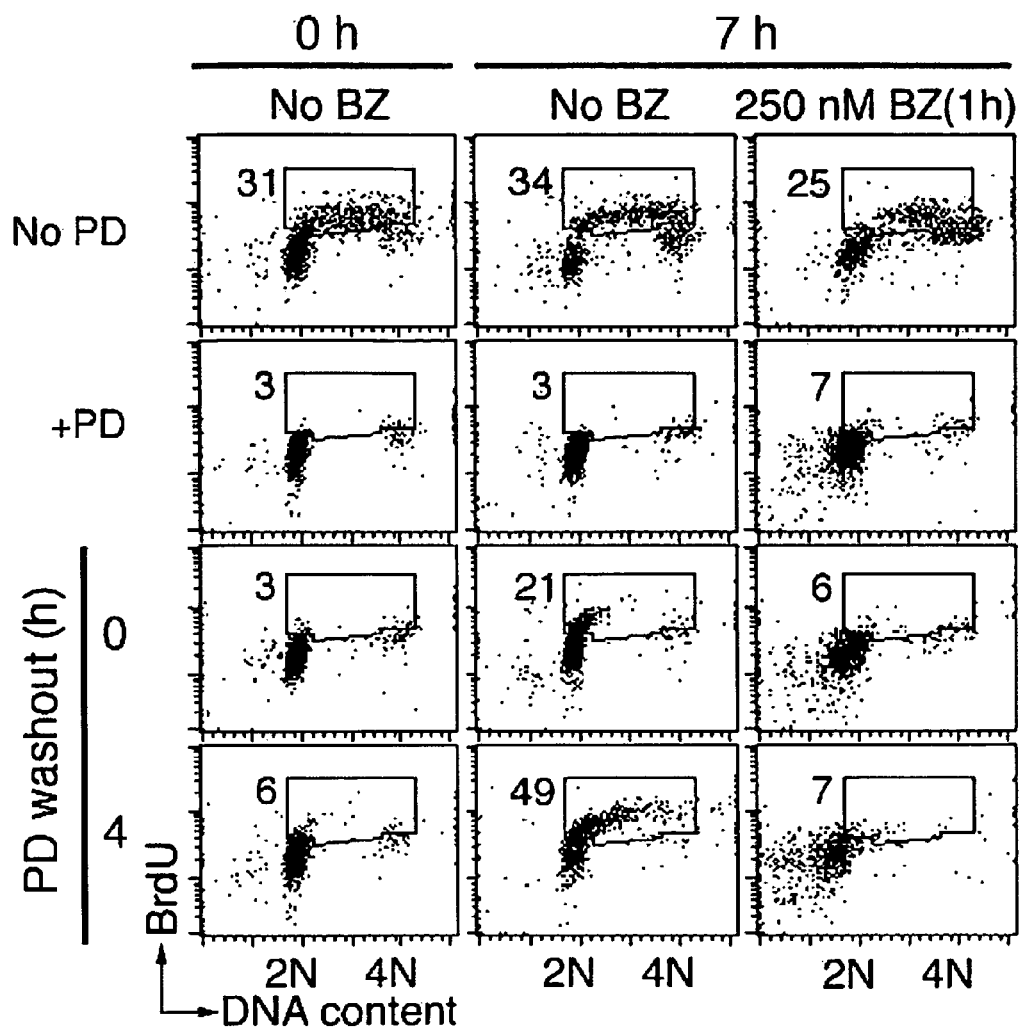
Figure 1I:
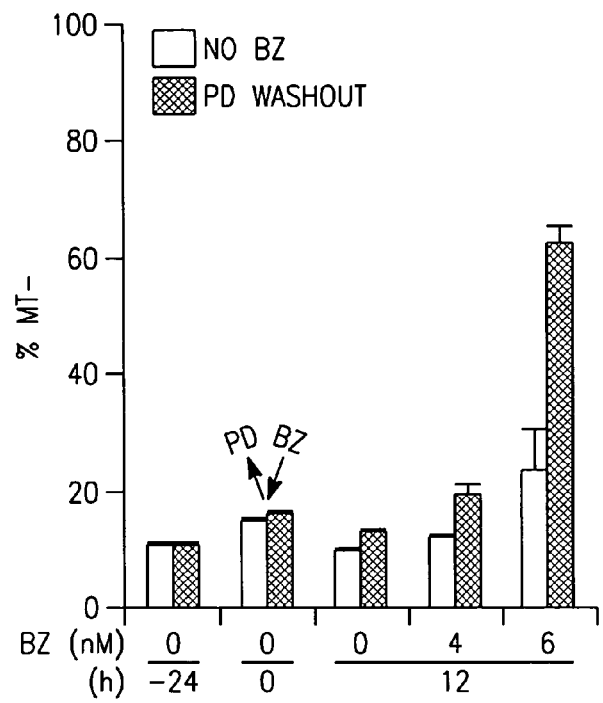
Figure 1J:
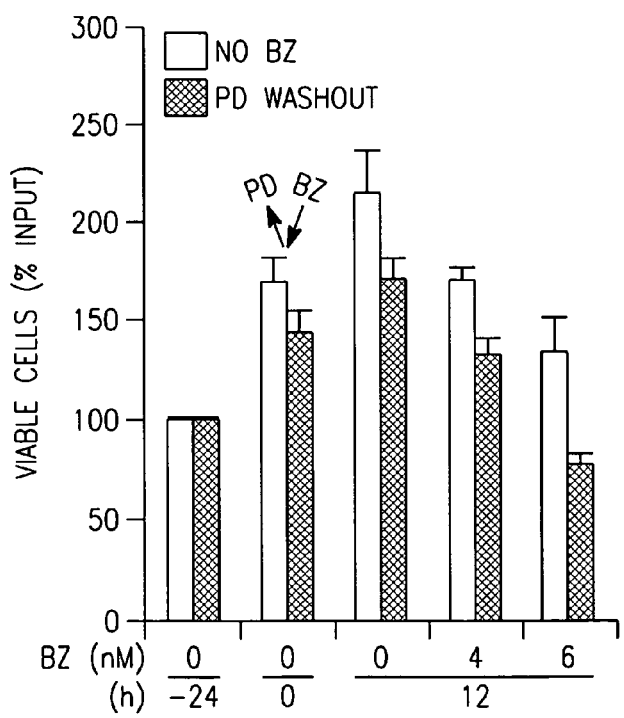

Cytotoxic killing was determined 6 hours later in the absence of bortezomib, by assessing cell viability and mitochondrial membrane depolarization (MMD) (loss of mitochondrial membrane potential) indicative of apoptosis (FIG. 1F). Bortezomib killing was profoundly enhanced by prior G1 arrest regardless of the continuous presence or absence of PD 0332991, and augmented further in cells pulsed with bortezomib during synchronous G1-S transition at 4 hours post PD 0332991 removal (FIG. 1G). The simultaneous loss of BrdU-uptake and G2/M cells along with increased DNA fragmentation confirmed that bortezomib killing was enhanced before or during S phase entry (FIG. 1H). As a corollary, adding bortezomib at sub-optimal concentrations (4 or 6 nM) upon removal of PD 0332991 also led to greater MMD and loss of viability in the continuous presence of bortezomib when compared with unsynchronized cells (FIG. 1I-J). Thus, by inducing exclusive and reversible G1 arrest in the absence of apoptosis, selective inhibition of CDK4 and CDK6 by PD 0332991 sensitizes cycling myeloma cells to bortezomib killing, and this is markedly augmented during synchronous G1-S transition following the removal of the G1 block.

Figure 2A:
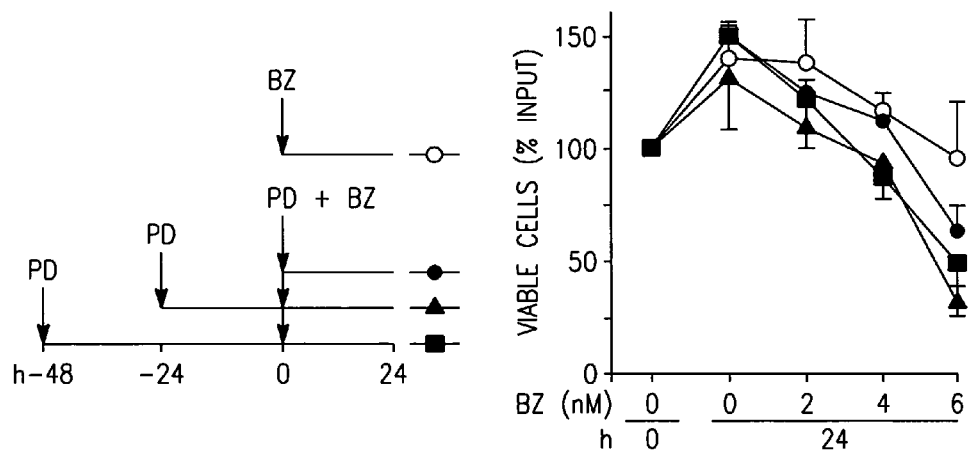
FIG. 2A-N illustrate that induction of sustained G1 arrest enhances cytotoxic killing of myeloma cells.
Figure 2B:
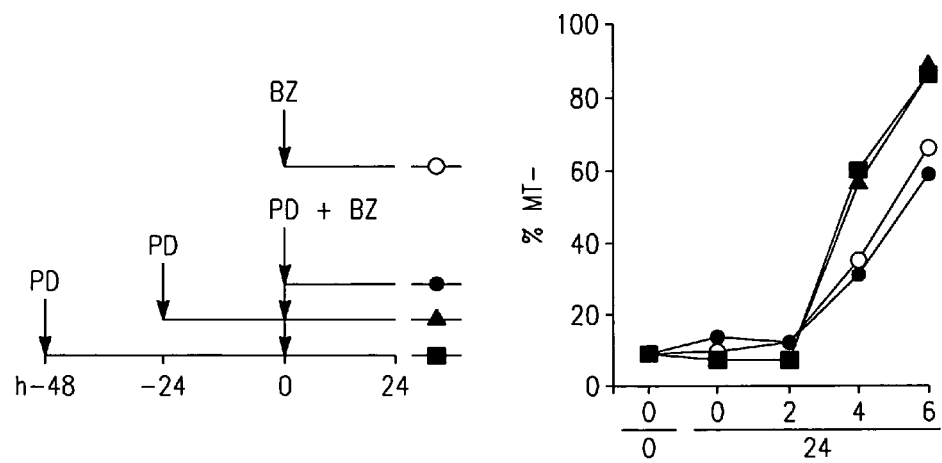
FIG. 2B shows the mitochondrial membrane potential (MT$^-$) of MM1.S. after culturing as diagrammed.
Figure 2C:
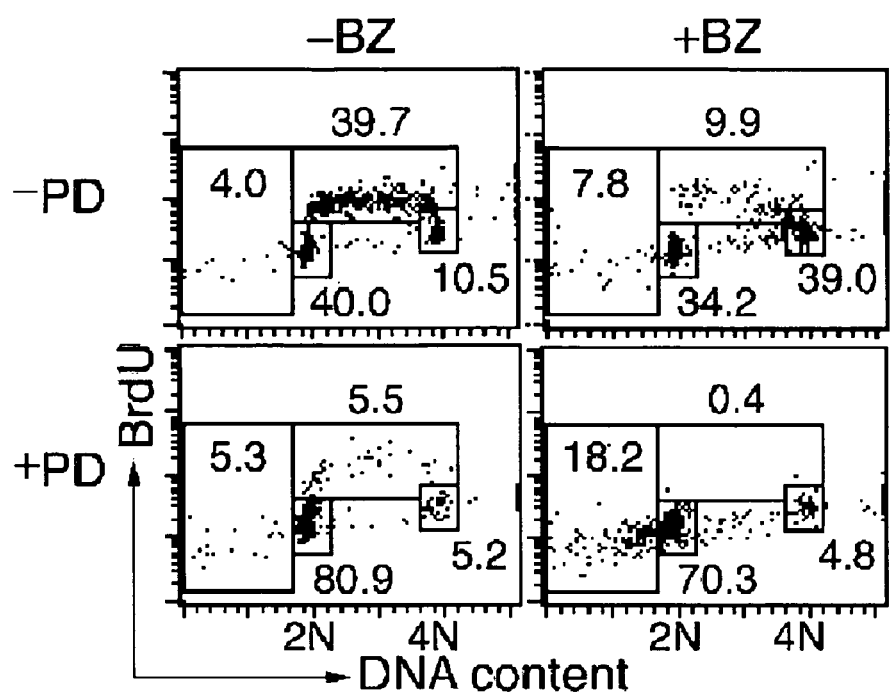
FIG. 2C shows simultaneous analysis of BrdU uptake and DNA content after 24 hr of PD 0332991 pretreatment followed by incubation with bortezomib (4 nM) for 24 hr.
Figure 2D:
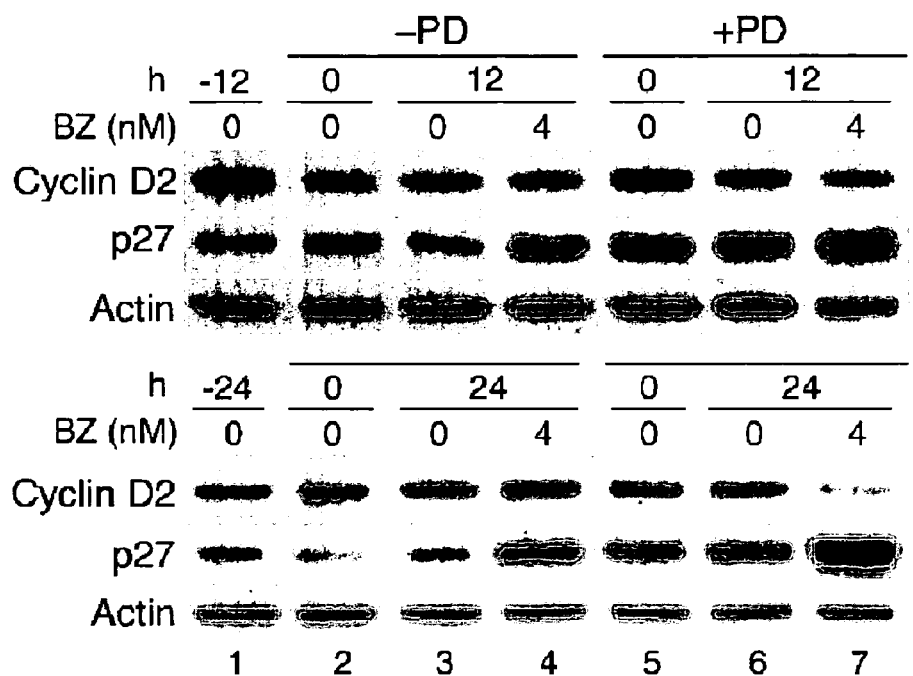
FIG. 2D shows an immunoblot of cell proteins probed with antibodies directed against the proteins listed to the left of the blot. Cells were incubated for 12 h or 24 h with bortezomib after 24 hr of PD 0332991 pretreatment.
Figure 2E:
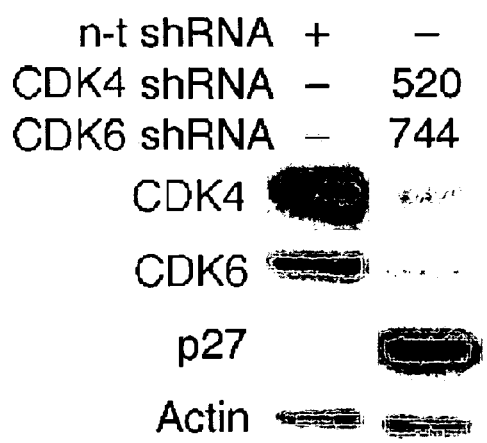
FIG. 2E is an immunoblots showing that CDK4 and CDK6 expression is dramatically reduced by shRNA interference but that such knockdown of CDK4 and CDK6 expression also dramatically increases p27 expression. MM1.S cells were transduced with CDK4 (clone 520) and CDK6 (clone 744), or with the non-targeting (n-t) shRNA lentiviral particles. At 66 h post transduction, the expression of CDK4, CDK6 and p27 were determined by immunoblotting.
Figure 2F:
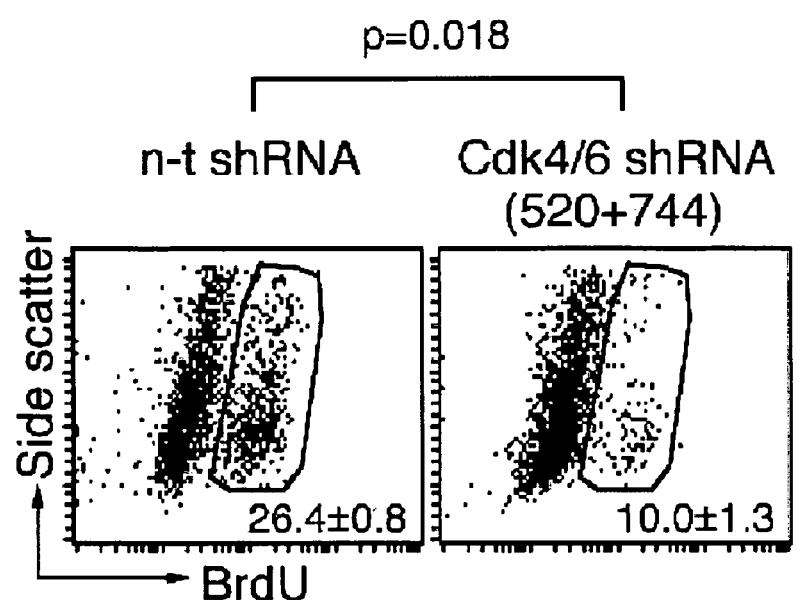
FIG. 2F shows the percentage of BrdU-positive cells at 72 hr post-transduction as determined by FACS.
Figure 2G:
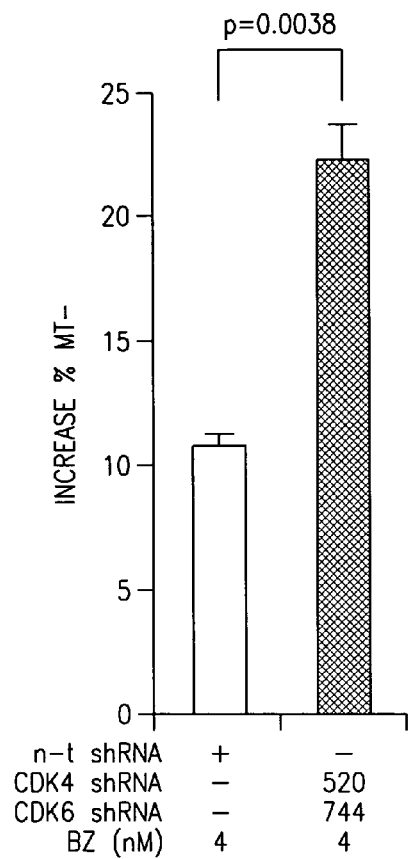
FIG. 2G shows the percentage of increase in MT$^-$ in cells transduced with CDK4 (clone 520) and CDK6 (clone 744) shRNA and subsequently treated with bortezomib (6 nM) for 17 h.
Figure 2H:
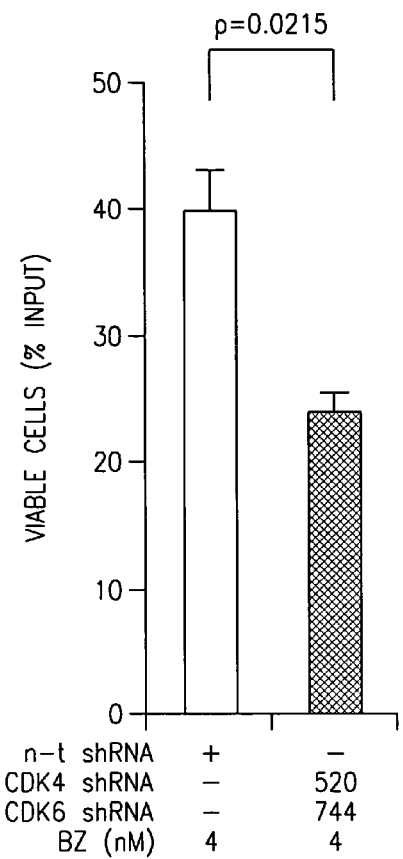
FIG. 2H shows the viability of cells transduced with CDK4 (clone 520) and CDK6 (clone 744) shRNA and subsequently treated with bortezmib (6 nM) for 17 h.
Figure 2I:
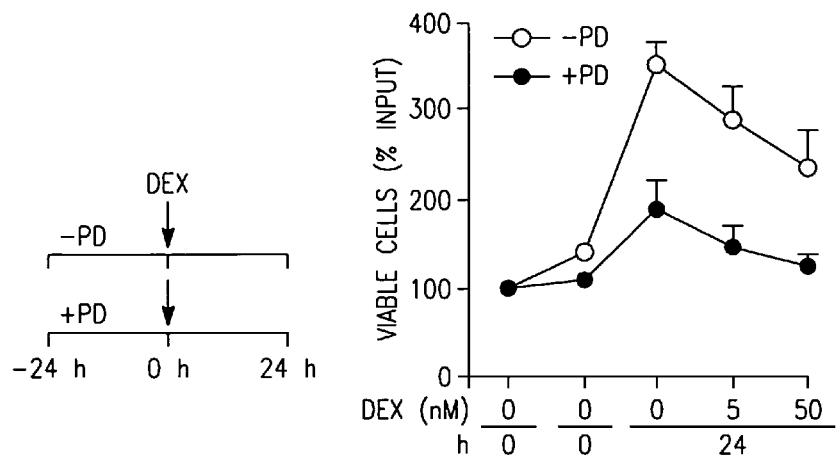
FIGS. 2I and 2J show the viability of dexamethasone-sensitive MM1.S cells and dexamethasone-resistant MM1.R cells respectively after treatment with dexamethasone (dex) using the protocol depicted in the schematic diagrams to the left of the graphs.
Figure 2J:
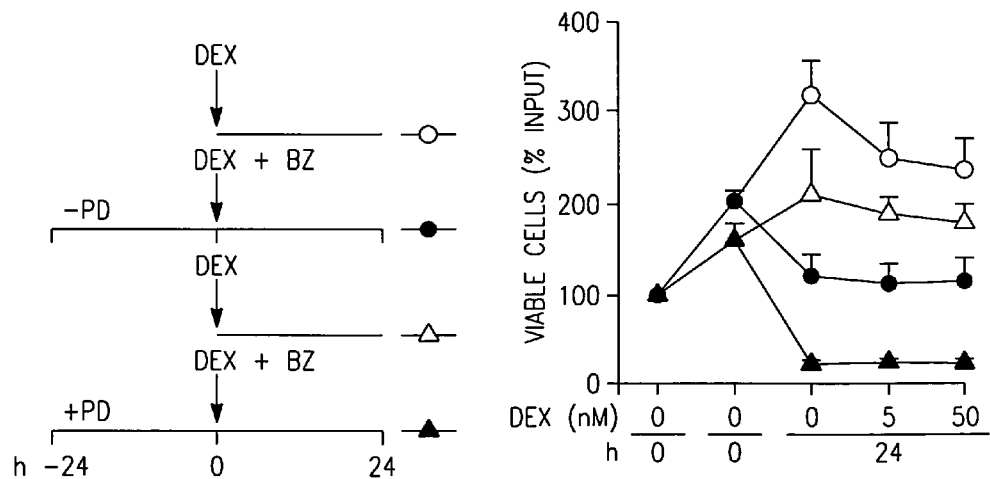
Figure 2K:
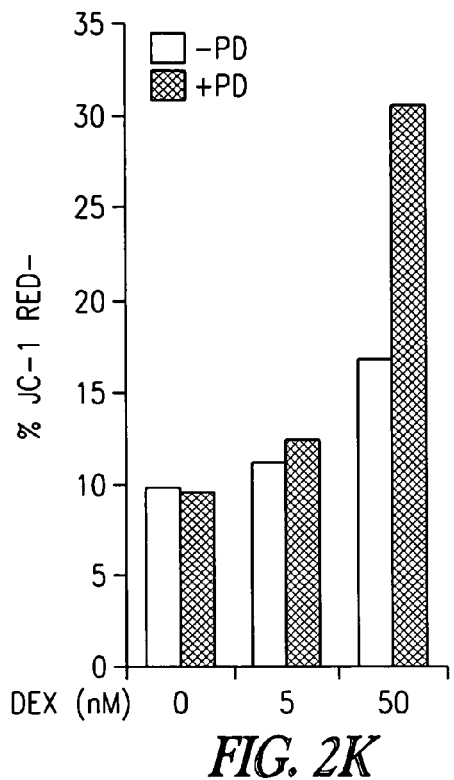
FIGS. 2K and 2L show the mitochondrial membrane potential (MT$^-$) of dexamethasone-sensitive MM1.S cells (FIG. 2K) and dexamethasone-resistant MM1.R cells (FIG. 2L) after treatment with PD and dexamethasone (dex) at the indicated concentrations as detected by JC-1 red$^-$. p-value was determined by two-tailed t-test.
Figure 2L:
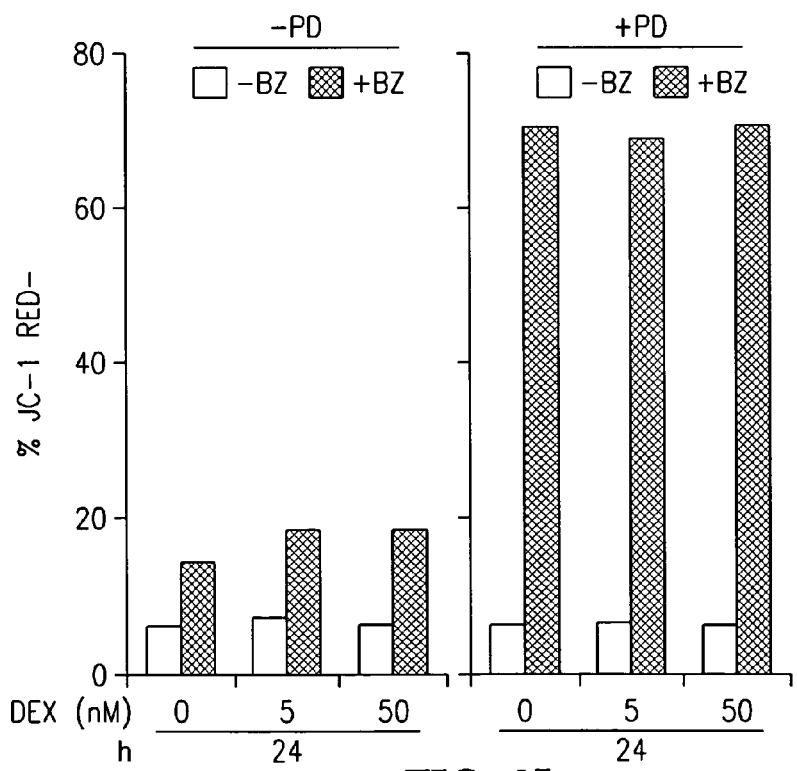
Figure 2M:
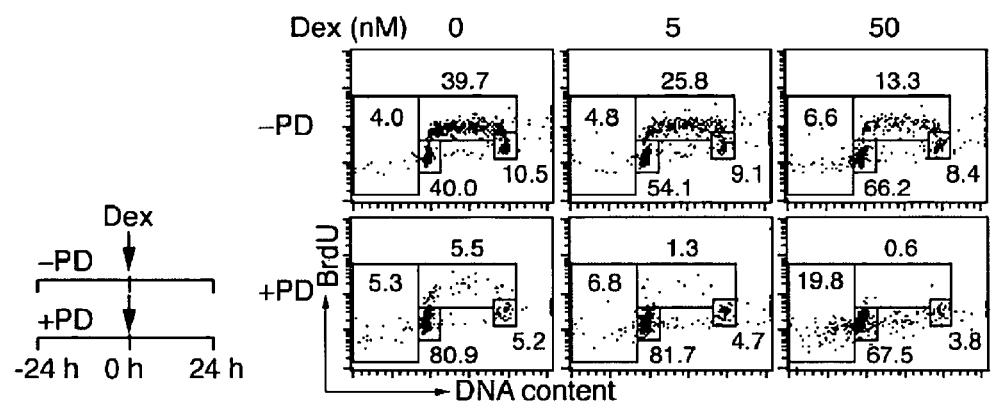
FIG. 2M shows the BrdU incorporation and DNA content of dexamethasone-sensitive MM1.S cells treated as shown in the schematic diagram to the left.
Figure 2N:
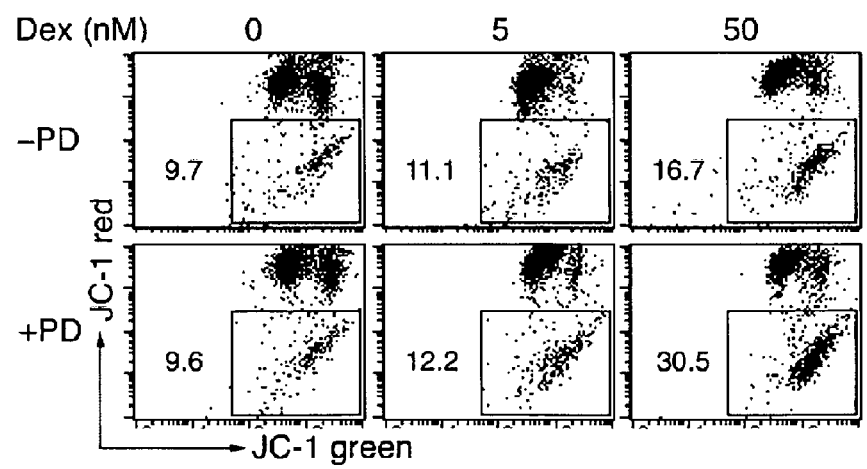

Sustained Inhibition of CDK4/6 Primes Chemoresistant Myeloma Cells to Cytotoxic Killing Through Induction of Mitochondrial Membrane Depolarization Killing by low dose bortezomib (2-6 nM) was greater when it was added to HMCLs at 24 or 48 hours after PD 0332991 treatment than when bortezomib was present concurrently with PD 0332991 (FIG. 2A-B; some data not shown). These results further verify that sustained G1 arrest enhances cytotoxic killing of myeloma. As expected, the absence of BrdU-uptake in PD 0332991-treated cells was accompanied by a marked accumulation of G1 cells, but not dead cells (FIG. 2C). Bortezomib (6 nM) alone induced a striking loss of cells in the S phase and prominent increase in the proportion of G2/M cells and dead cells, consistent with preferential killing of cells entering the S phase. However, bortezomib killed myeloma cells in G1 in synergy with prior PD 0332991 treatment, as observed with high doses of bortezomib (FIGS. 2C and 1F-H). This correlated with synergistic elevation of $p27^{Kip1}$ protein and reduction of cyclin D2, corroborating that the cells were arrested in 01 (FIG. 2D). Furthermore, induction of G1 arrest by knocking down both CDK4 and CDK6 with shRNA interference, shown by the dramatic increase in p27 protein and reduction in BrdU-uptake, markedly augmented bortezomib killing by increasing MMD (FIG. 2E-H). Sustained inhibition of CDK4/6 by PD 0332991, therefore, primes cycling myeloma cells to cytotoxic killing in early G1.

Similarly, induction of G1 arrest by PD 0332991 augmented MMD and cytotoxic killing by low dose dexamethasone (Dex) (5-50 nM), at a level comparable to simultaneous treatment with substantially higher concentrations of PD 0332991 (2 mM) and Dex (0.1-1.0 mM) (Baughn et al., 2006) (Baughn et al., 2006)(FIG. 2I-L). Of particular interest, PD 0332991 sensitized Dex-resistant MM1.R cells (a clonal derivative of MM1.S cells) to killing by low dose bortezomib, leading to virtual eradication of cells in 24 hours through dramatic acceleration of MMD independent of Dex (FIG. 2I-L). Induction of sustained G1 arrest by PD 0332991 inhibition of CDK4/6, therefore, primes HMCLs, including chemoresistant myeloma cells, for killing by more than one cytotoxic agent through synergistic induction of MMD.

Sustained G1 Arrest Primes Chemoresistant Primary Myeloma Cells for Cytotoxic Killing Despite Stromal Protection The possibility that induction of sustained G1 arrest with PD 0332991 followed by low doses of bortezomib killing (referred to as PD-B) may overcome chemoresistance was addressed in freshly isolated CD138+ BMM cells obtained from the patients described in Table 1. Freshly isolated CD138+ BMM cells were co-cultured with mitomycin-treated human HS-5 BM stromal cells (BMSC)s in the presence of IL-6 and IGF-1. Under these conditions, proliferation of BMM cells is extended transiently, while BMSC are insensitive to PD-B killing due to G2/M arrest.

Figure 3A:
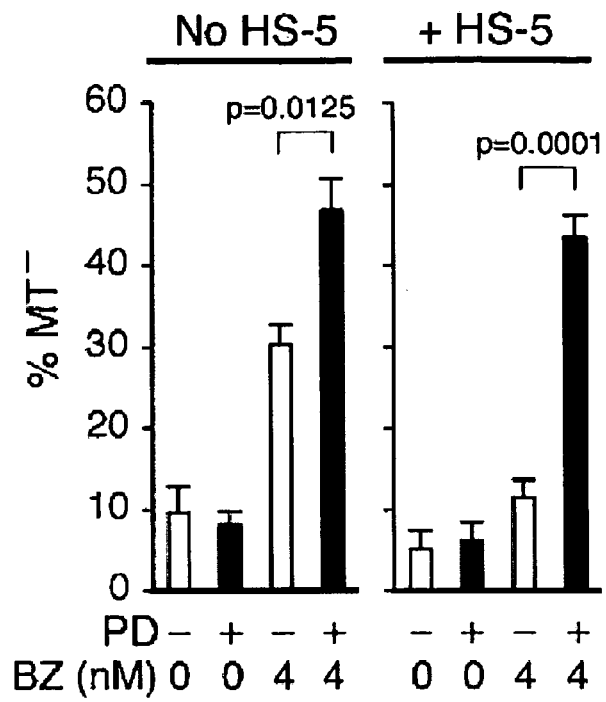
FIG. 3A-J show that induction of G1 arrest primes primary myeloma cells for killing by bortezomib.
Figure 3B:
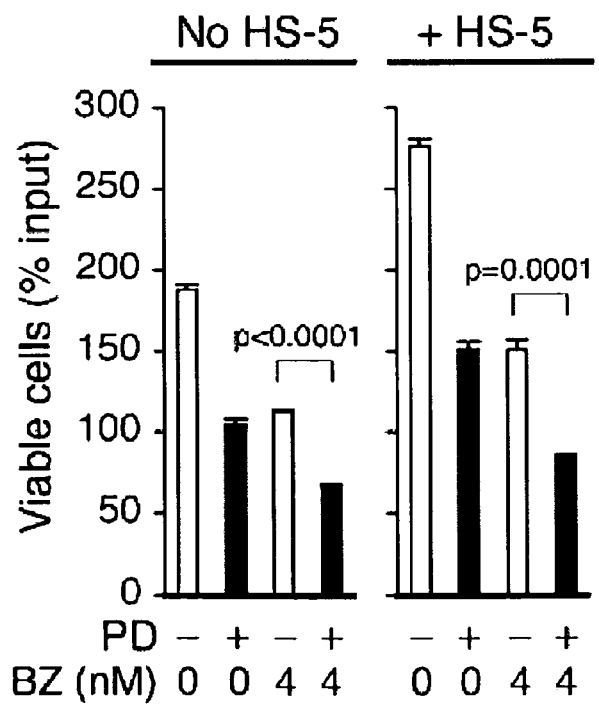
Figure 3C:
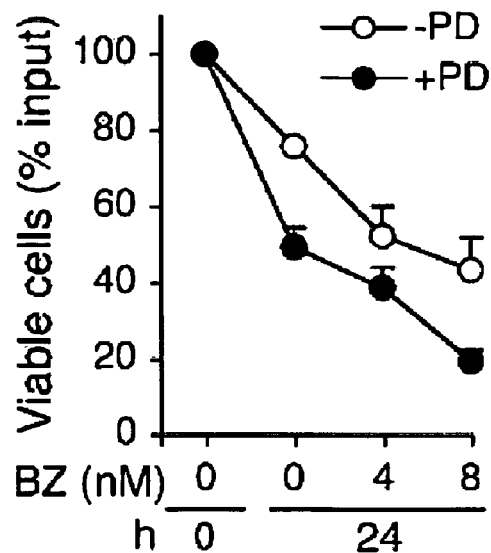
Figure 3D:
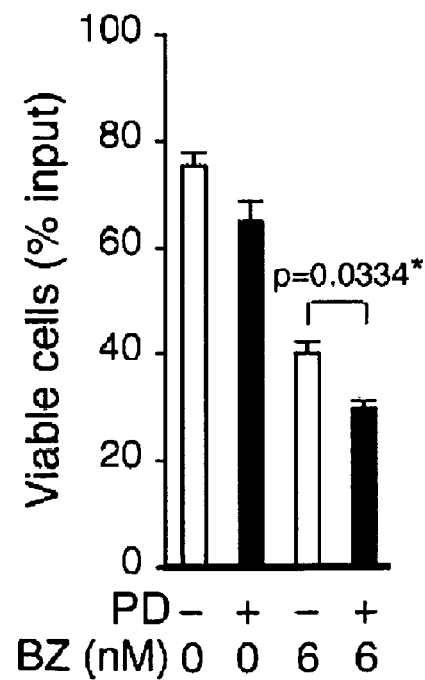
Figure 3E:
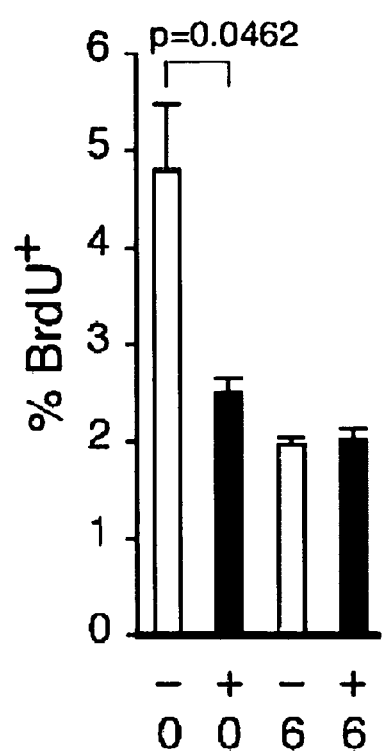
Figure 3F:
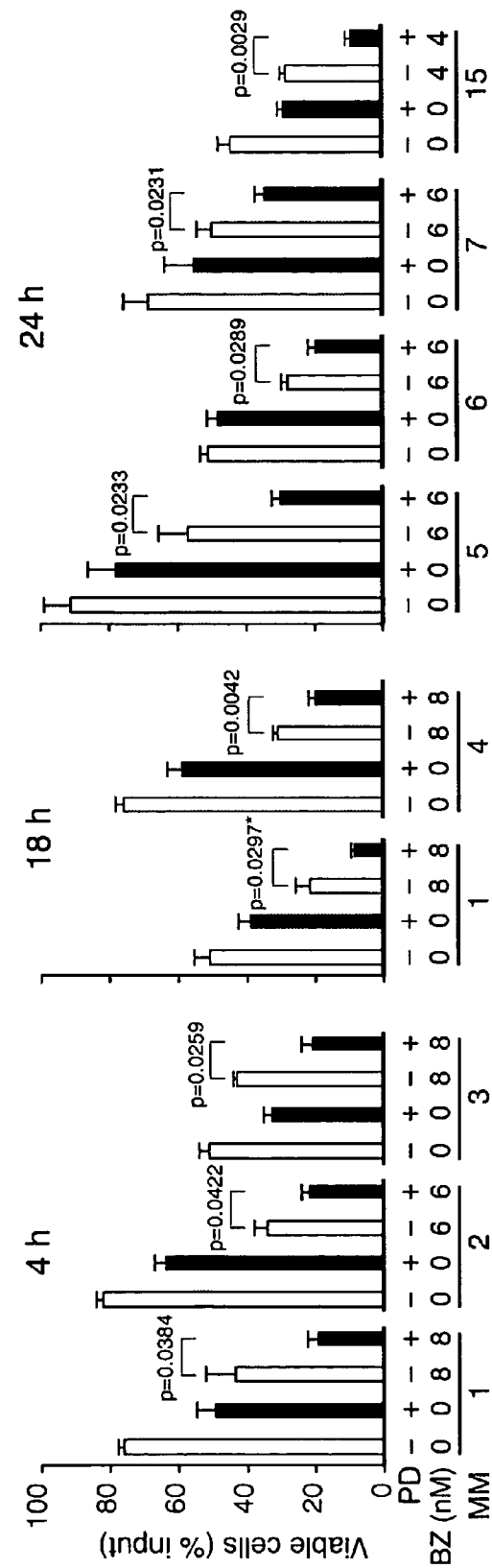
Figure 3G:
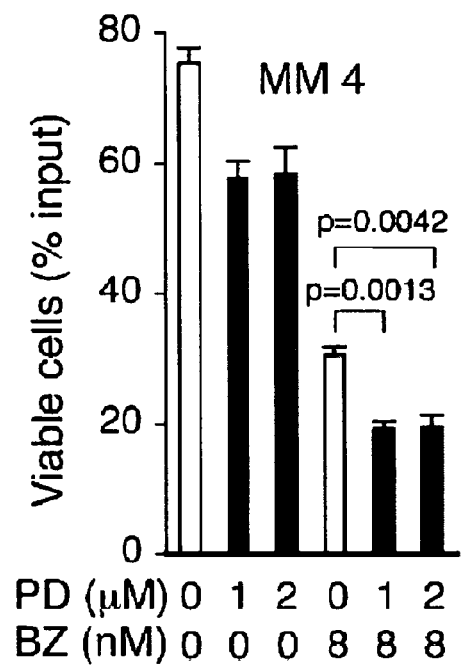
Figure 3H:
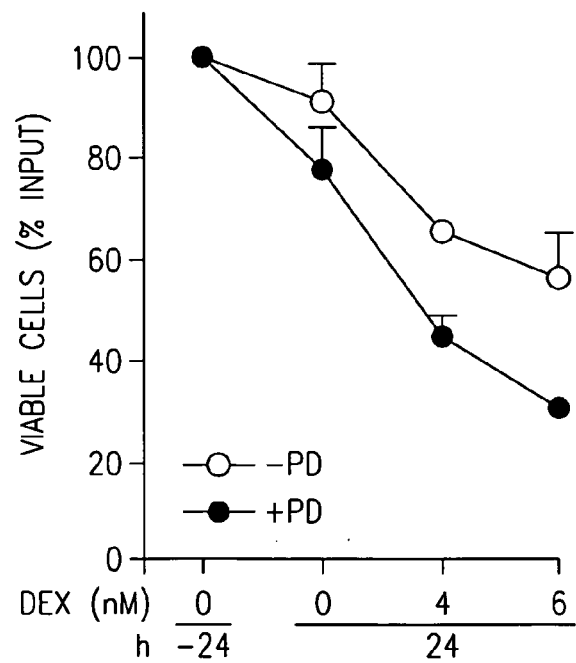
Figure 3I:
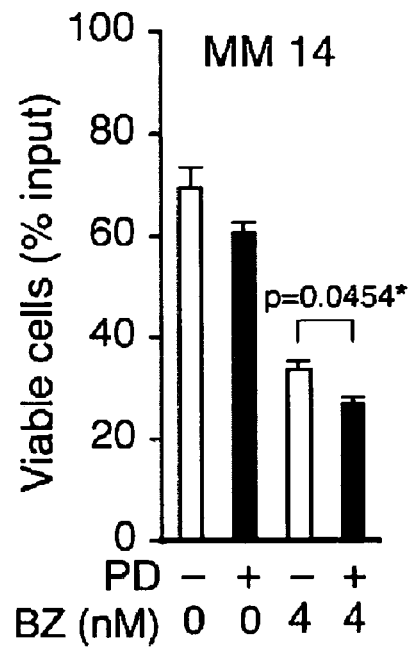
Figure 3J:
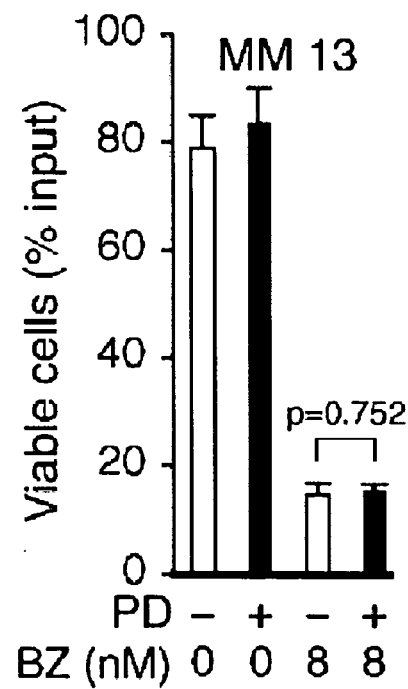

FIG. 3A-B demonstrate that synergistic killing of HMCLs by PD-B was maintained in the presence of BMSC, despite protection from bortezomib killing. The reduction of live BMM cells in 24 hours ex vivo was greater in the presence of PD 0332991 (1-2 μM), presumably due to acceleration of G1 arrest, or bortezomib because it induces apoptosis (FIG. 3C-E). Pretreatment with PD 0332991 for 4-24 hours markedly augmented bortezomib killing, except for those BMM cells that were exceptionally sensitive to bortezomib (e.g., MM 13) (FIG. 3E-I).

Figure 4A:
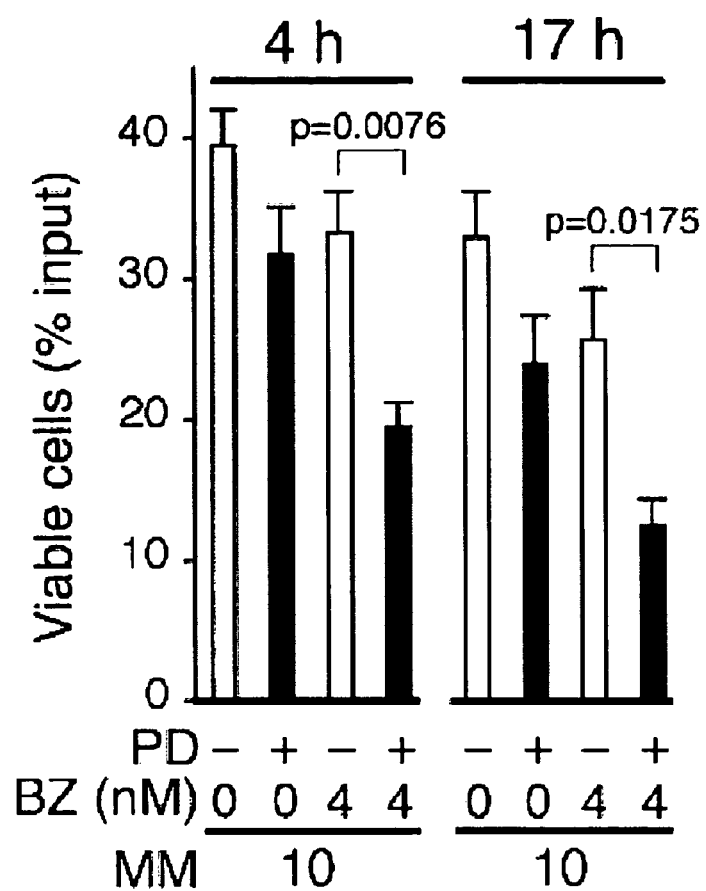
FIG. 4A-E show that sustained G1 arrest overcomes chemoresistance in primary myeloma cells. FIG. A-D illustrate the viability of primary BMM cells co-cultured with HS-5 cells in the presence of bortezomib (4 nM) for 24 h after pretreatment with PD 0332991 (2 μM) for 4 or 17 h (FIG. 4A), or for 4 or 24 h (FIG. 4B). The amount of bortezomib (BZ; 4 nM or 6 nM) is shown below the bar graph, opposite "BZ.
Figure 4B:
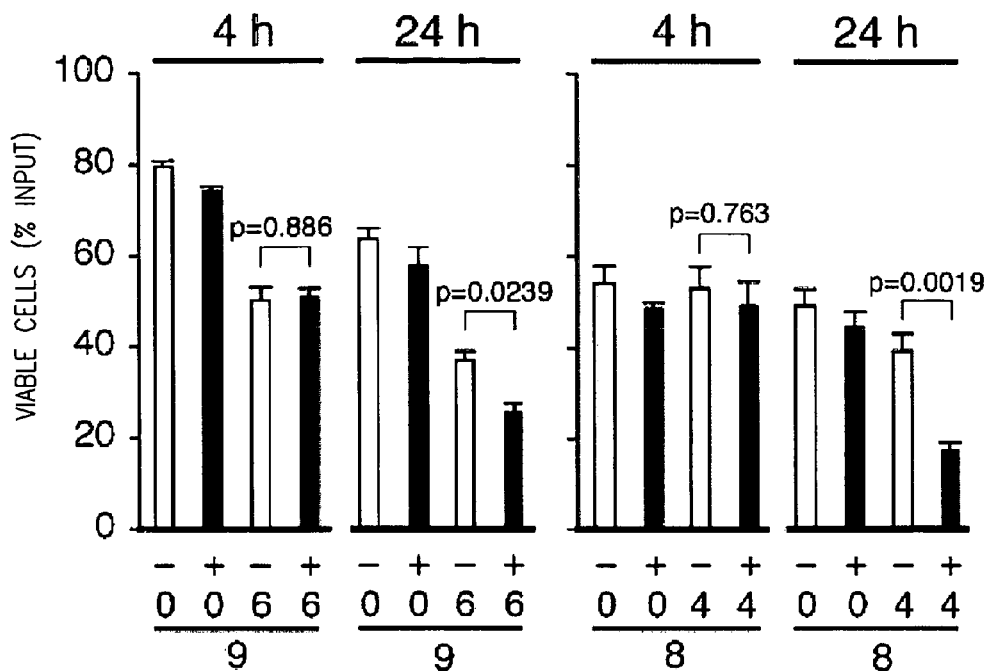
Figure 4C:
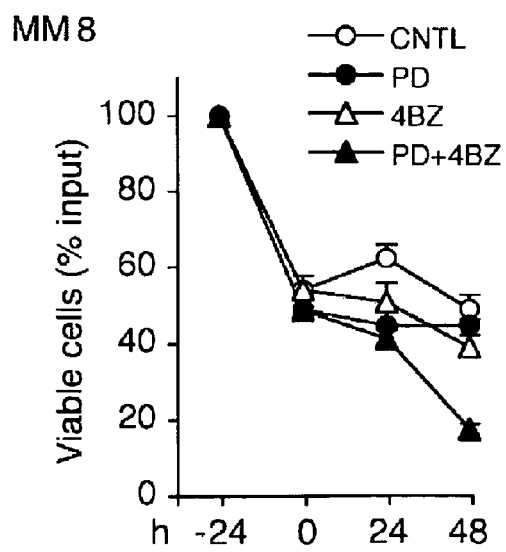
Figure 4D:
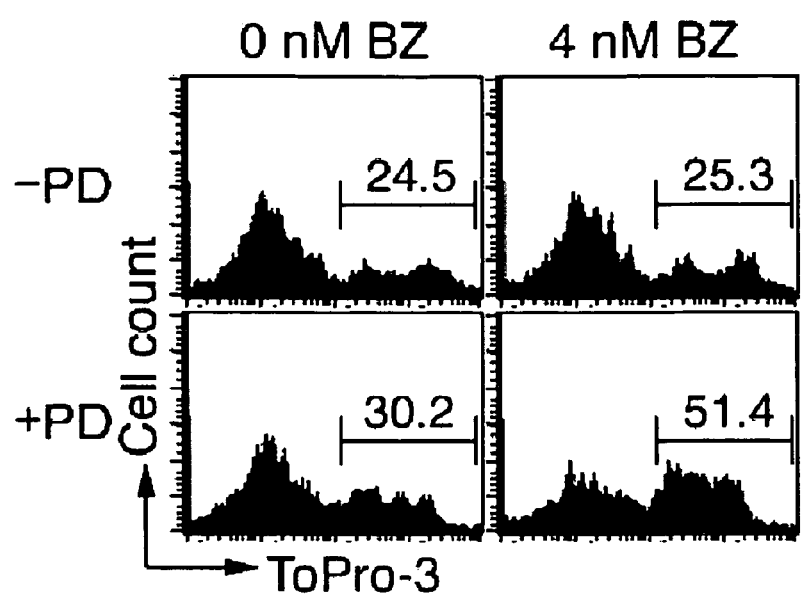

Importantly, pretreatment with PD 0332991 for 4 hours was sufficient to sensitize BMM cells isolated from some bortezomib-refractory patients (MM10) to killing by bortezomib (FIG. 4A). Extending PD 0332991 pretreatment to 24 hours rendered other bortezomib-refractory BMM cells susceptible to bortezomib killing, whether they remained resistant (MM 8) or became sensitive to bortezomib with time of culturing (MM 9) (FIG. 4B). Synergistic killing was amplified by 48 hours of bortezomib treatment (MM 8) as evidenced by the To-Pro3 assay (FIG. 4C). Induction of G1 arrest by PD 0332991 therefore primes primary BM myeloma cells to cytotoxic killing and overcomes chemoresistance despite protection by BMSCs.

Synergistic Tumor Suppression by Inhibiting CDK4/6 in Combination with Cytotoxic Killing The anti-tumor activity of inhibiting CDK4/6 in combination therapy was then evaluated in a NOD/SCID xenograft human myeloma model by serial noninvasive bioluminescence imaging (BLI). In this model, disseminated tumors develop following injection of Luc+GFP+MM1.S cells that stably express the HSV-TK-eGFP-luciferase fusion protein (Wu et al., 2005).

Figure 4E:
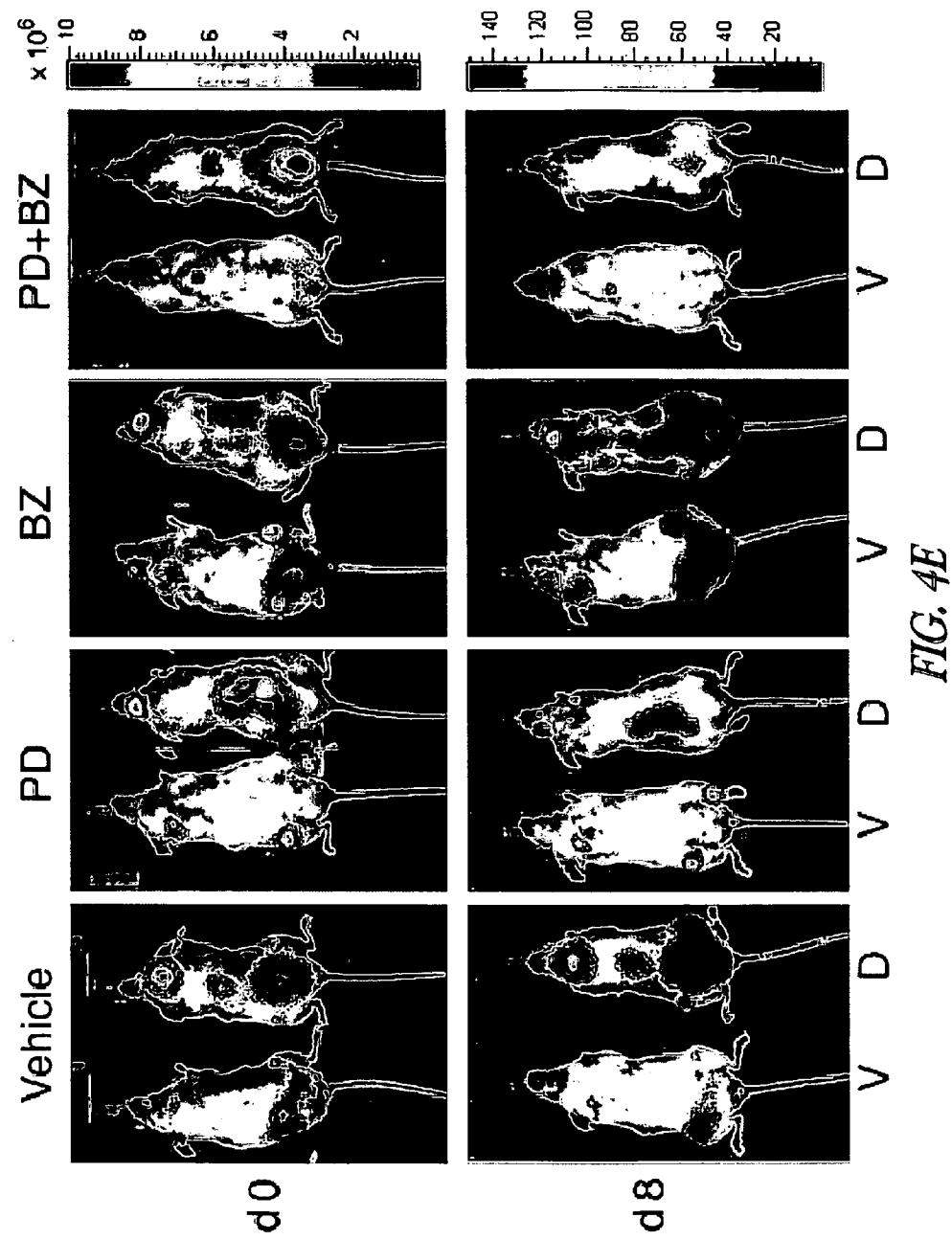
Figure 5A:
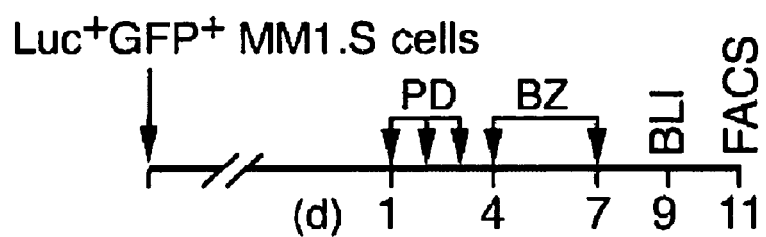
FIG. 5A-H illustrate synergistic tumor suppression by PD 0332991 in combination with bortezomib.
Figure 5B:
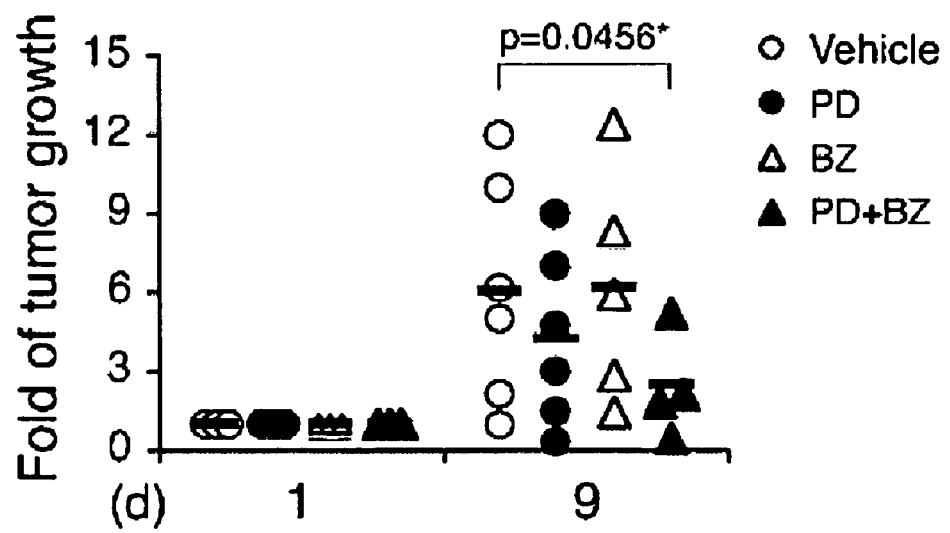
Figure 5C:
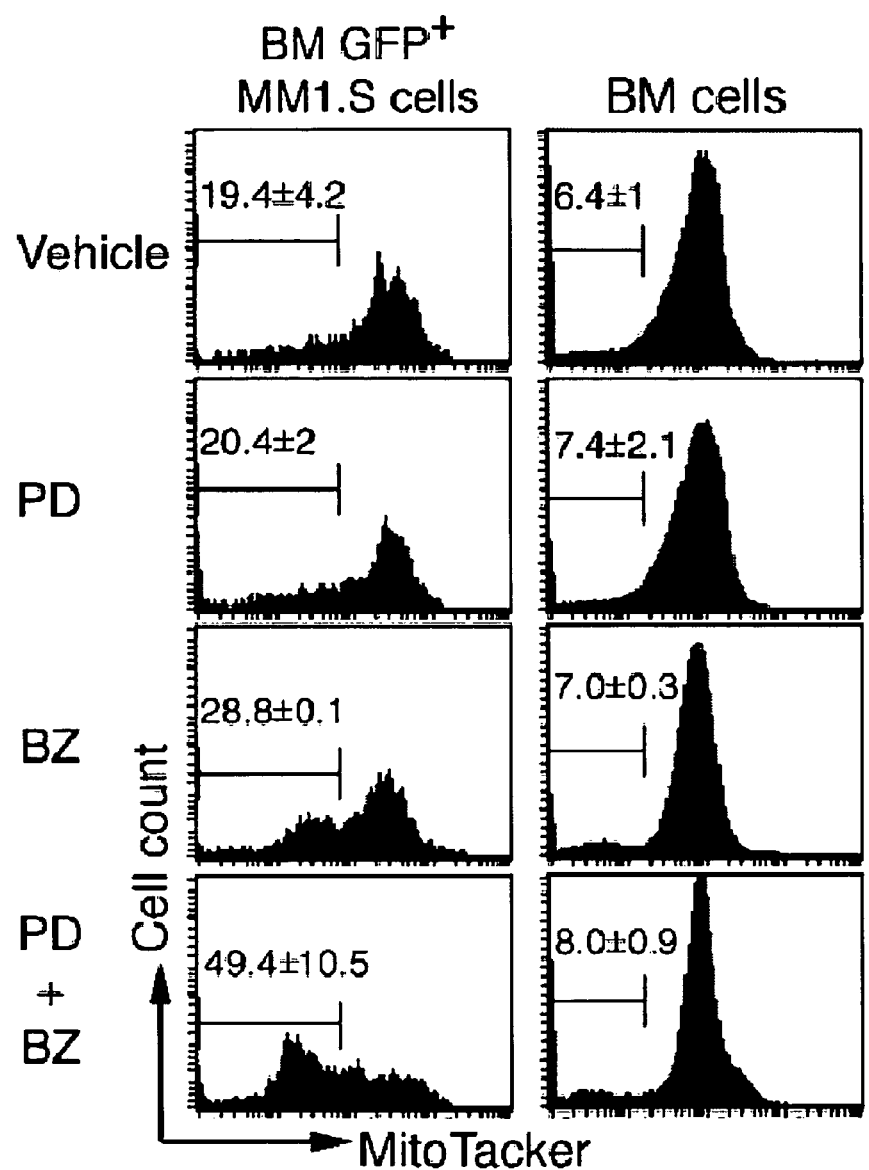

To augment cytotoxic killing by sustained G1 arrest as well as synchronous G1-S transition, mice developing aggressive tumors were treated with a sub-optimal dose of bortezomib (0.25 mg/kg) on day 4, after being given PD 0332991 (150 mg/kg) daily for 3 days, and on day 7 when cell cycle resumed following the decline of serum PD 0332991 (FIG. 5A and data not shown). At this concentration, PD 0332991 inhibits CDK4/6 in tumor cells overnight and reduced tumor burden profoundly by day 9 in a related CAG NOD/SCID myeloma model (Baughn et al., 2006). BLI analysis on day 8 demonstrated that tumor development was synergistically suppressed by the combination therapy, while only modestly reduced by PD 0332991 or bortezomib treatment alone (FIG. 5B and FIG. 4E). Moreover, MMD was differentially induced by bortezomib in human myeloma cells but not in the mouse BM cells, and was augmented by PD 0332991 pretreatment (FIG. 5C). These observation indicate that induction of G1 arrest and synchronous cell cycle progression by PD 0332991 leads to synergistic tumor suppression by amplifying differential killing of myeloma cells by bortezomib in vivo.

Figure 5D:
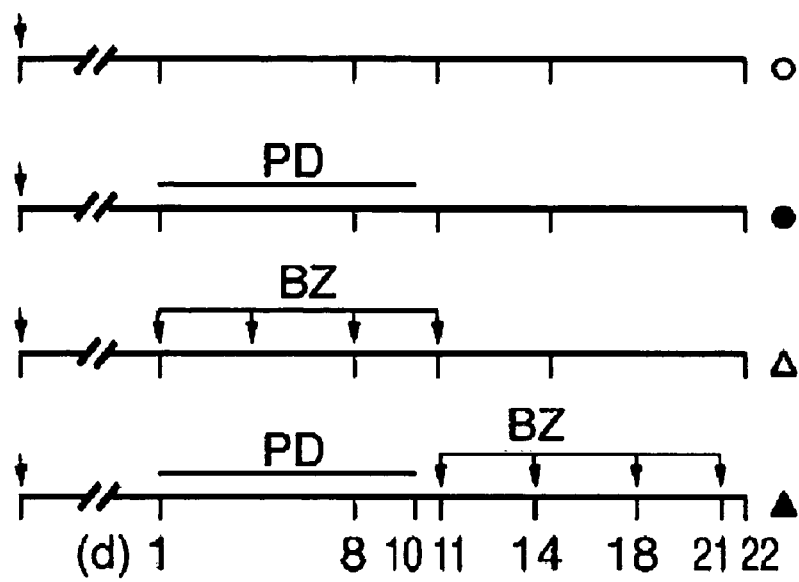
Figure 5E:
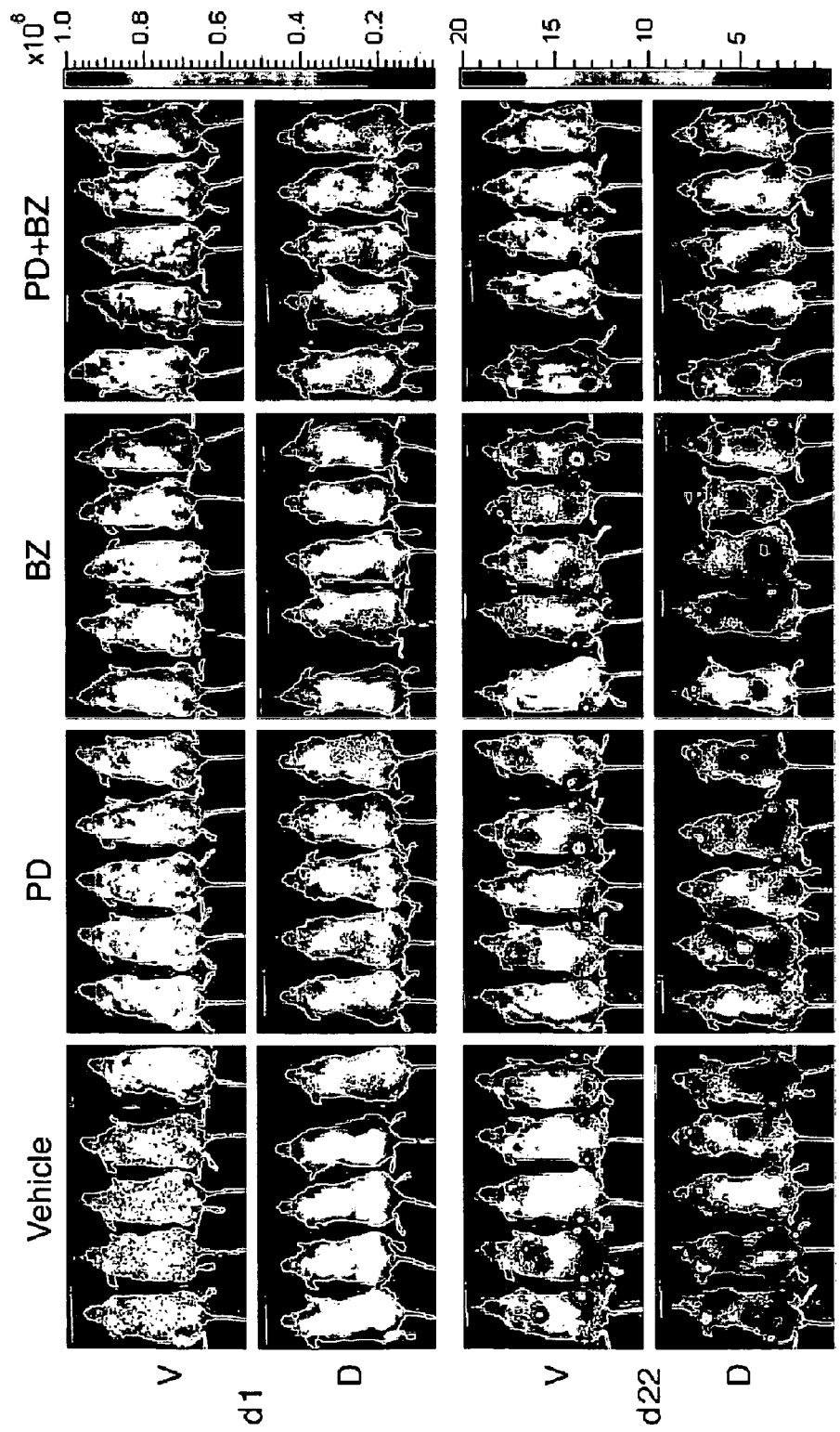
Figure 5F:
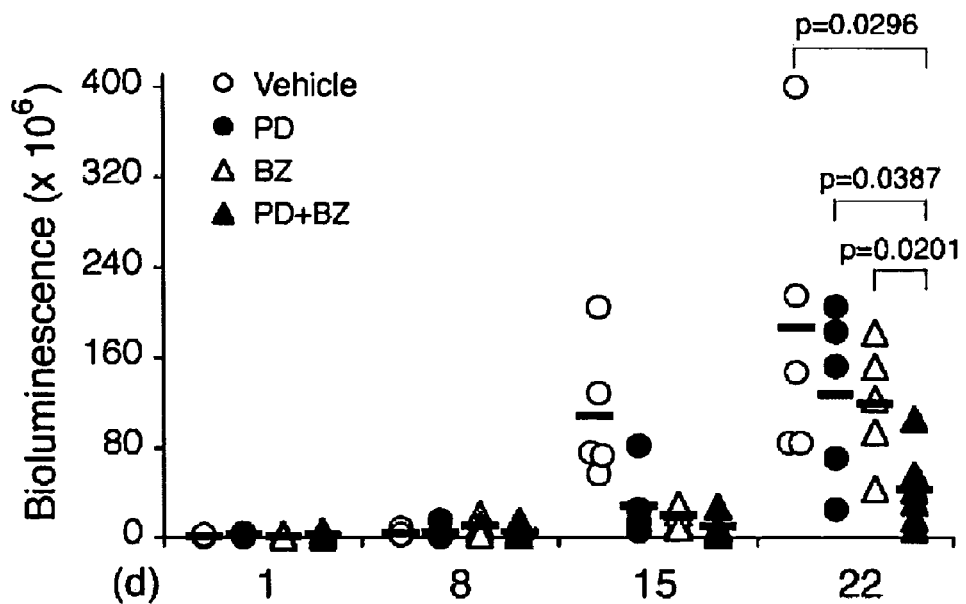

Prolonging treatments with low concentrations of PD 0332991 (80 mg/kg, 10 days) and bortezomib (0.25 mg/kg, days 10, 13, 17, and 20) early in tumor development reduced tumor growth to 20% of the vehicle treated mice by day 21, as opposed to less than 50% by PD 0332991 or bortezomib alone (FIG. 5D-F). Therefore, sequential treatment with sub-optimal concentration of PD 0332991 and bortezomib early in disease development also leads to synergistic tumor suppression.

Suppression of IL-6 Signaling Augments Bortezomib Activation of Bim, Noxa and Caspase-9

Figure 5G:
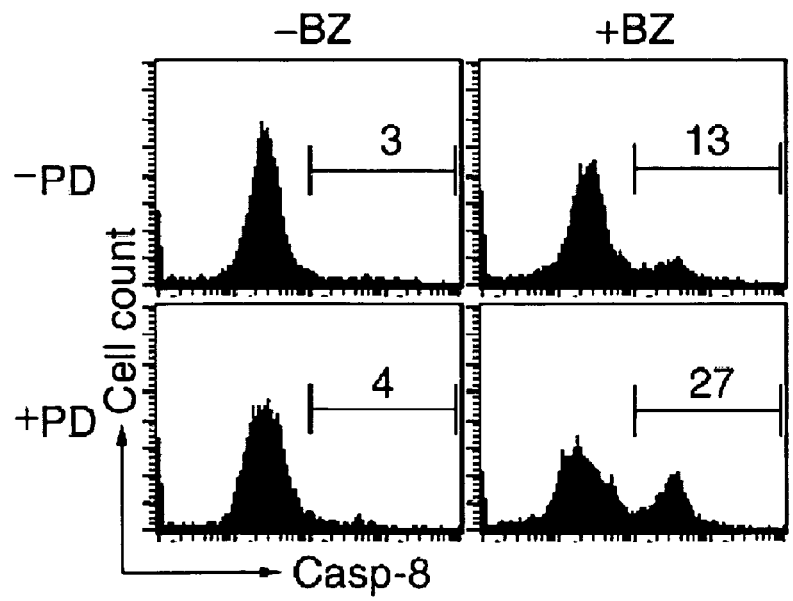
Figure 5H:
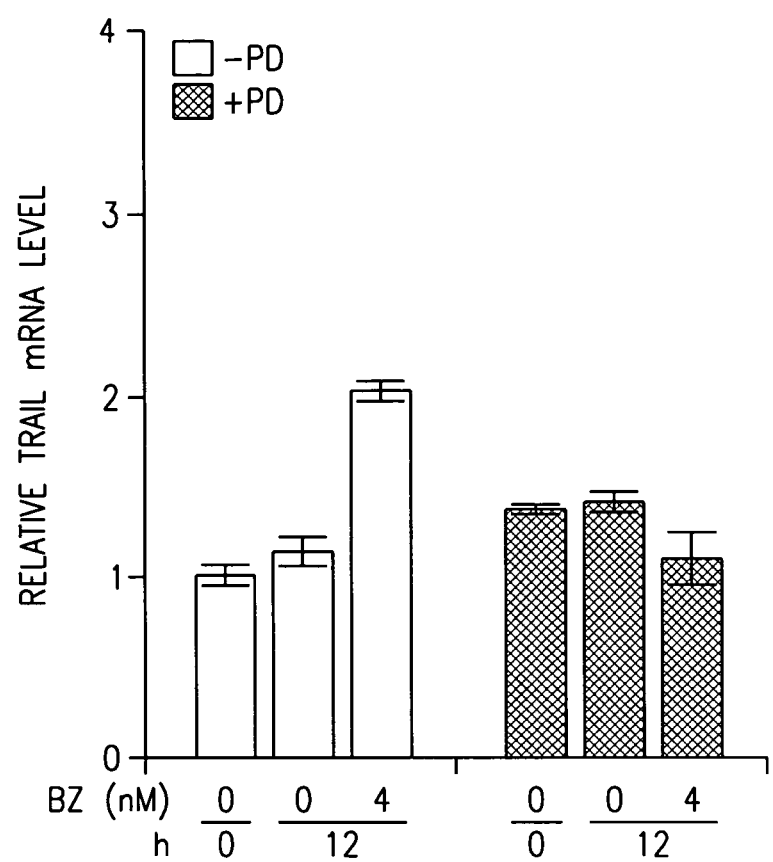
Figure 6A:
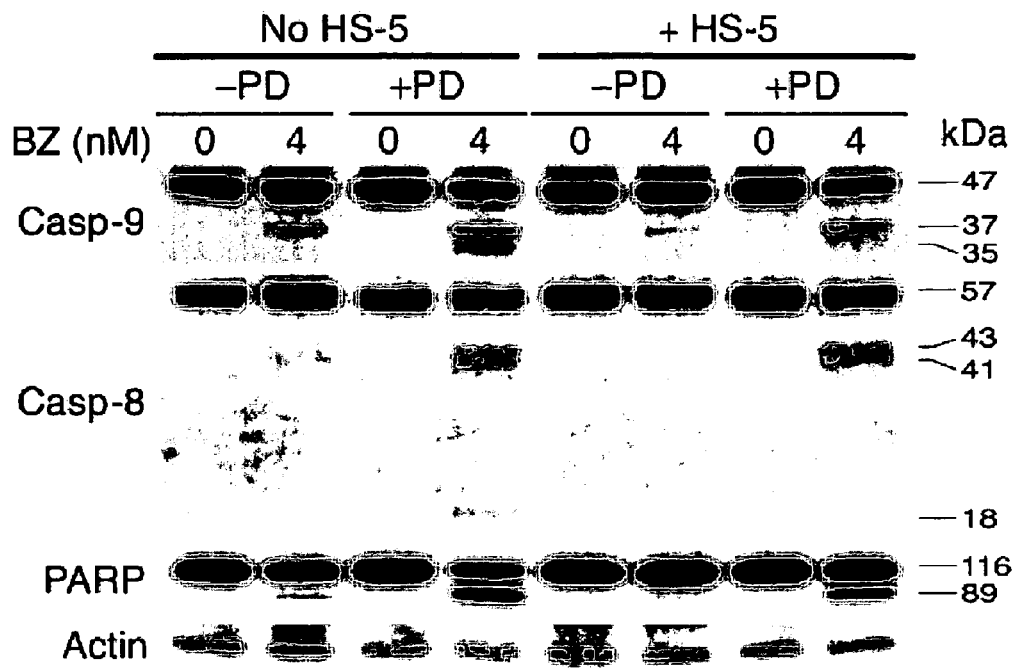
FIG. 6A-H illustrate that suppression of gp130 signaling augments activation of Bim, Noxa and caspase by bortezomib.
Figure 6B:
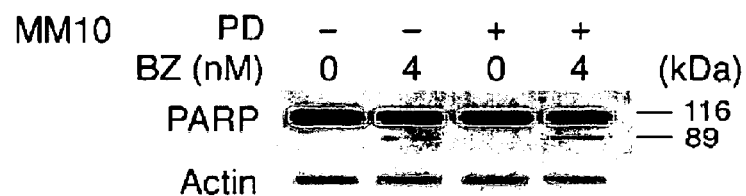

To address the mechanism that underlies synergistic killing in early G1 by PD-B, the inventors focused on signaling upstream and downstream of MMD, a signature for priming of myeloma cells by PD 0332991 to cytotoxic killing. Killing by PD-B is caspase-dependent as it is completely inhibited by the pan-caspase inhibitor ZVAD-FMK (data not shown). The cleavage of caspase-9 as well as poly ADP-ribose polymerase (PARP) was synergistically induced by PD-B in HMCLs and BMMs regardless of the presence of BMSCs, demonstrating that the downstream intrinsic apoptosis pathway was activated (FIGS. 6A-B). Activation of capase-8 by bortezomib was similarly augmented by prior PD 0332991 treatment (FIG. 6A and FIG. 5G-H), suggesting that death ligands such as TNF-α, FasL and TRAIL might have been induced to trigger the extrinsic apoptotic pathway (Petersen et al., 2007; Varfolomeev et al., 2007; Vince et al., 2007). However, no TNF-α or FasL mRNA was detected in myeloma cells under any condition, and TRAIL mRNA remained unchanged by PD-B despite a marginal increase by bortezomib (FIG. 5H and data not shown). Activation of caspase-8, therefore, is likely secondary to activation of the intrinsic apoptosis pathway (Slee et al., 1999), as a means to amplify apoptosis in PD-B.

Figure 6C:
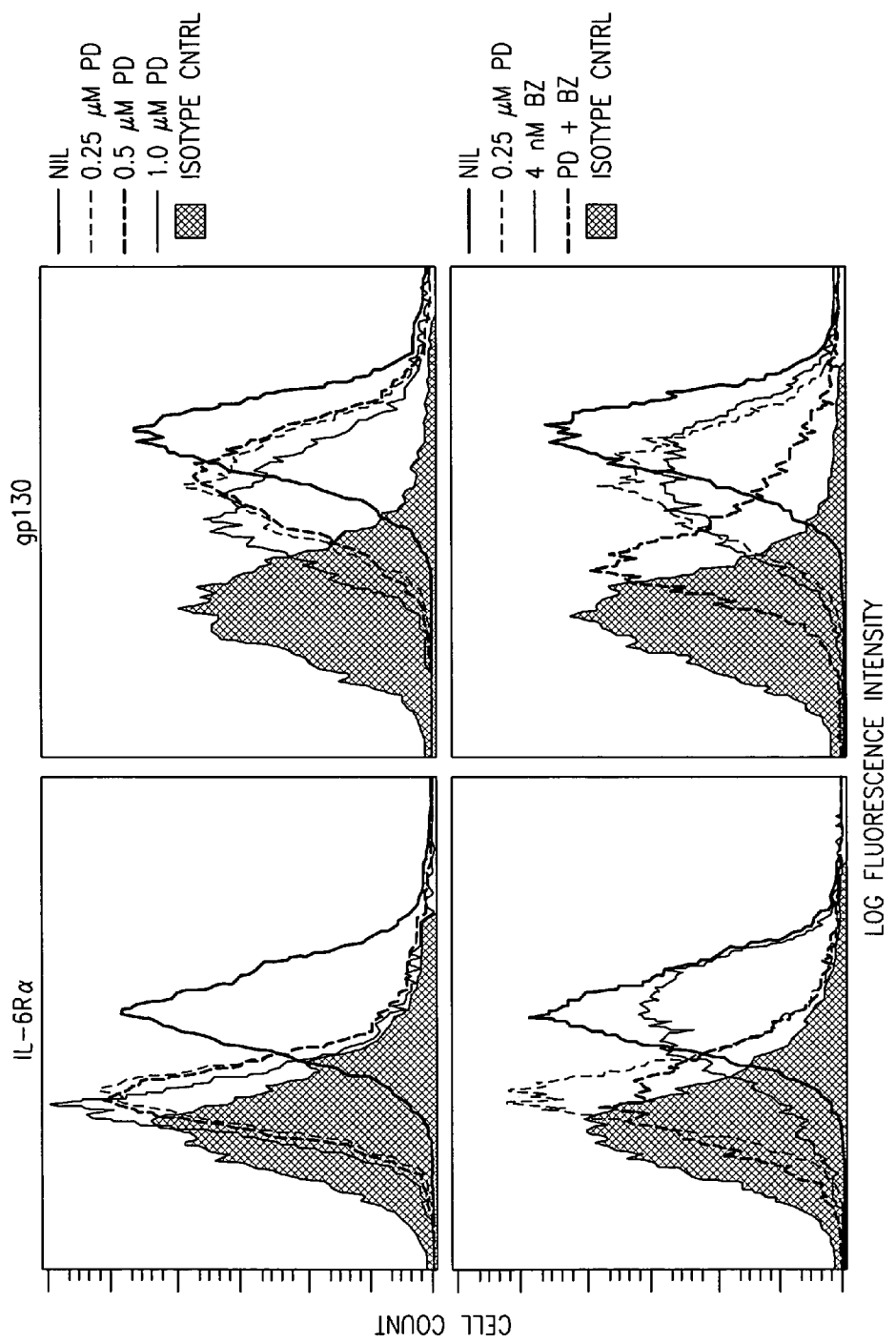
Figure 6D:
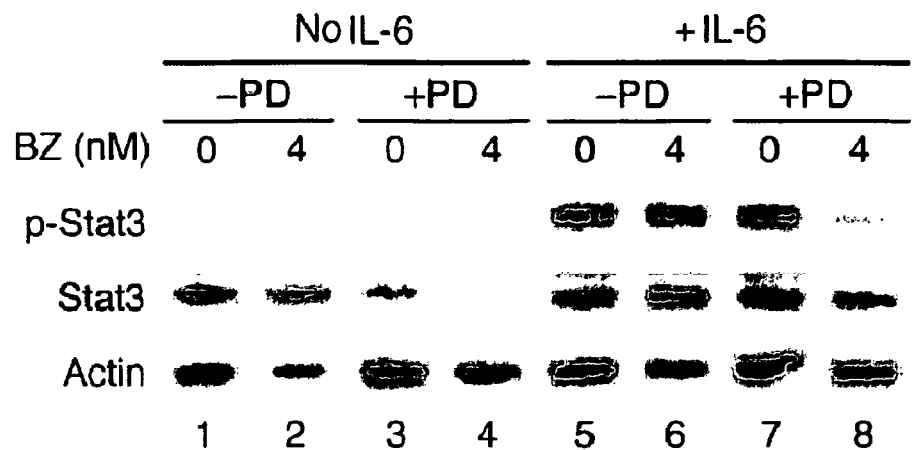
Figure 6E:
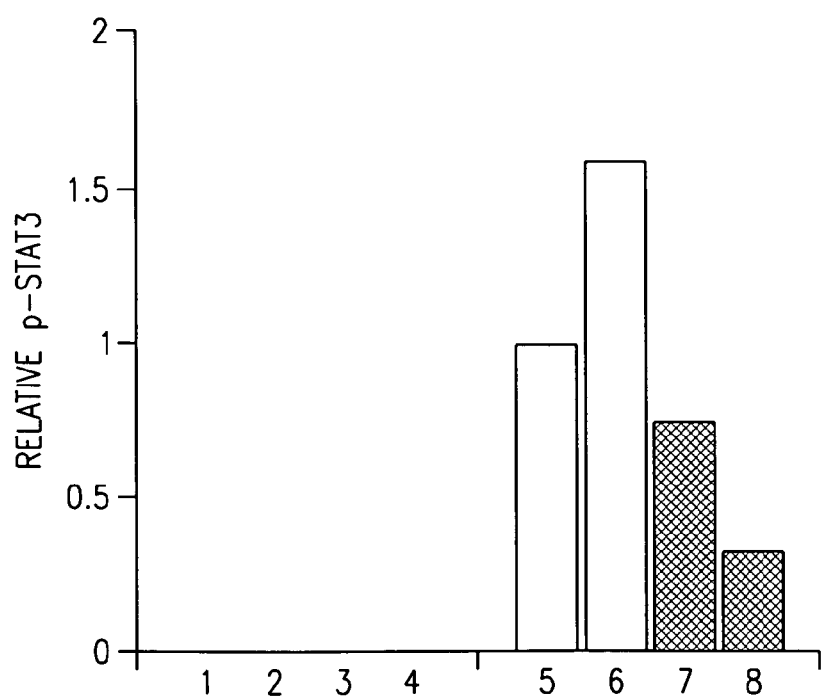

The absence of death ligands during synergistic activation of MMD and caspase-8 by PD-B despite protection by BMSCs (FIGS. 3-4, and 6A) suggests that critical BMSC-derived survival signals must have been disrupted. The inventors hypothesized that a likely survival signal candidate might be IL-6, which is essential for BMM survival, produced at high levels by BMSCs such as HS-5 cells (Roecklein and Torok-Storb, 1995) and can antagonize bortezomib killing of myeloma cells through IL-6 signaling (Chauhan et al., 1996). Testing indicated that the expression of surface IL-6a (gp80) on myeloma cells was virtually eliminated by PD 0332991 (0.25 mM), but did not vary in response to low dose bortezomib (4 nM). gp130, the signaling receptor subunit, was reduced synergistically by PD-B, but only modestly by PD 0332991 or bortezomib alone (FIG. 6C). Correspondingly, tyrosine phosphorylation of Stat3 (p-Stat3) upon IL-6 stimulation was impaired by treatment of cells with PD 0332991 and bortezomib, in part due to reduction of Stat3 protein in response to PD 0332991 (FIG. 6D-E). These data demonstrate that IL-6 signaling is impaired in cells treated with PD 0332991 and bortezomib due to differential reduction of IL-6Rα and Stat3 in G1-arrest and synergistic suppression of surface gp130 expression.

Figure 6F:
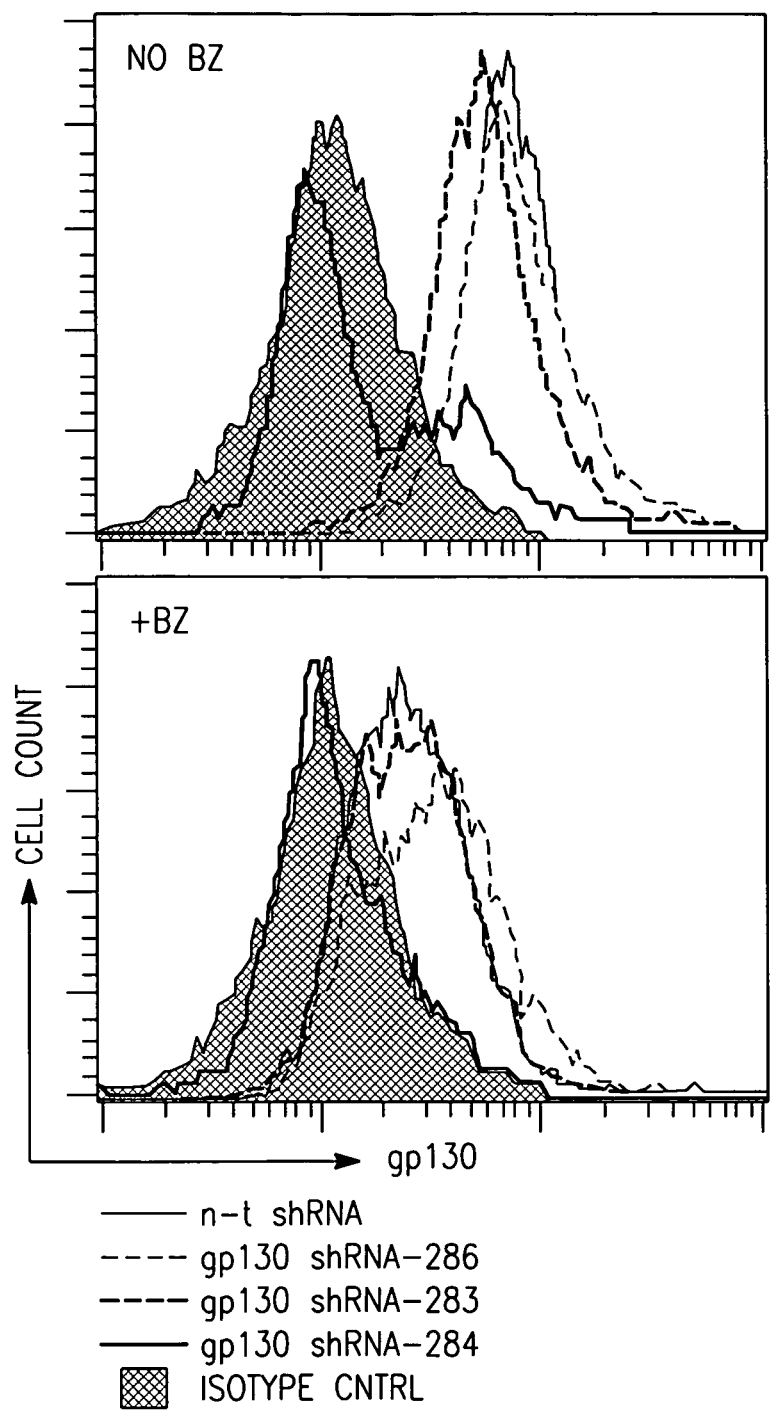
Figure 6G:
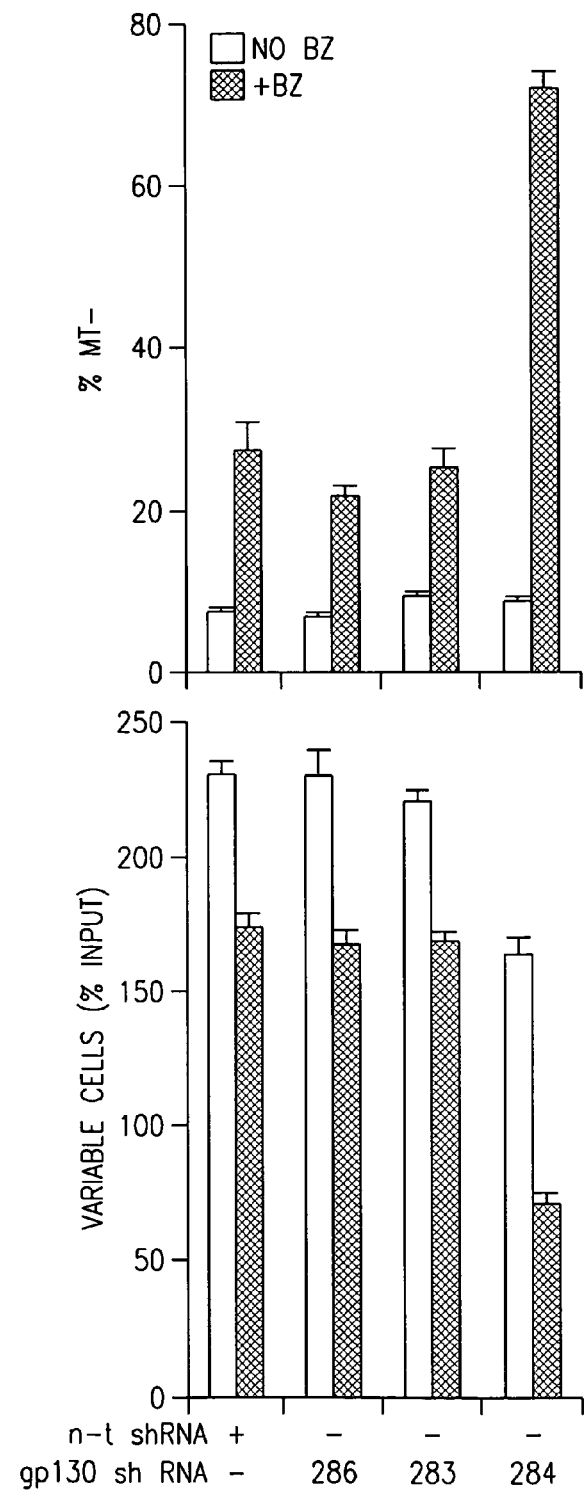
Figure 6H:
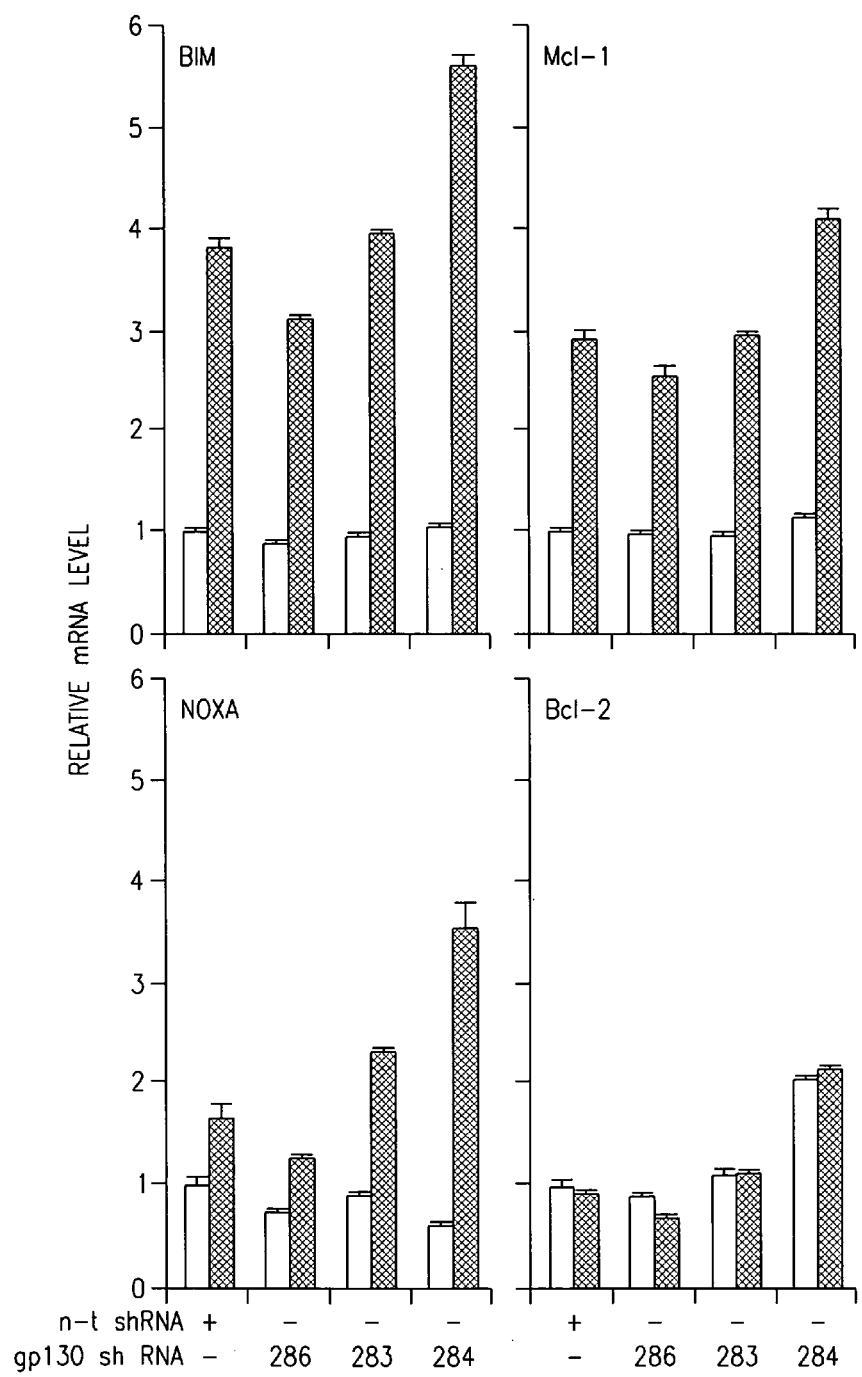

Survival of myeloma and normal plasma cells is tightly modulated by the interplay between anti-apoptotic and pro-apoptotic BH3-domain only proteins of the Bcl-2 family (Altmeyer et al., 1997; Gomez-Bougie et al., 2004), as is MMD (Adams and Cory, 2007). Bim and Noxa, two BH3-only proteins, are upregulated by bortezomib to induce apoptosis of myeloma cells (Gomez-Bougie et al., 2007; Qin et al., 2005). They are also exquisitely activated by cytokine withdrawal and endoplasmic reticulum stress (Dijkers et al., 2000; Puthalakath et al., 2007), suggesting that they may be up-regulated by impaired IL-6 signaling to enhance bortezomib killing. Knocking down gp130 expression by shRNA interference profoundly augmented MMD and loss of viability, as well as induction of Bim, Noxa and Mcl-1, but not Bcl-2, mRNAs, in response to bortezomib (FIGS. 6F-H) Collectively, these data indicate that in concert with loss of IL-6Rα and Stat3 expression, suppression of gp130 signaling impairs IL-6 signaling and augments bortezomib killing through differential activation of Bim, Noxa and Mcl-1 synthesis in cells treated with PD 0332991 and bortezomib.

Figure 7A:
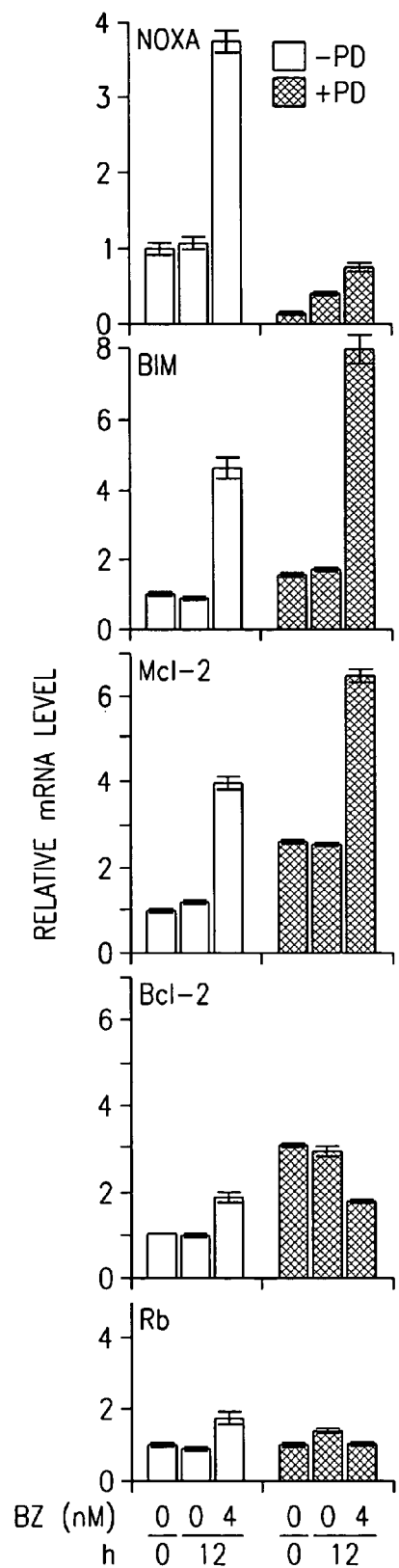
FIG. 7A-G illustrate that Bim mediates PD-B induced apoptosis via enhanced neutralization of Mcl-1 and Bcl-2.
Figure 7B:
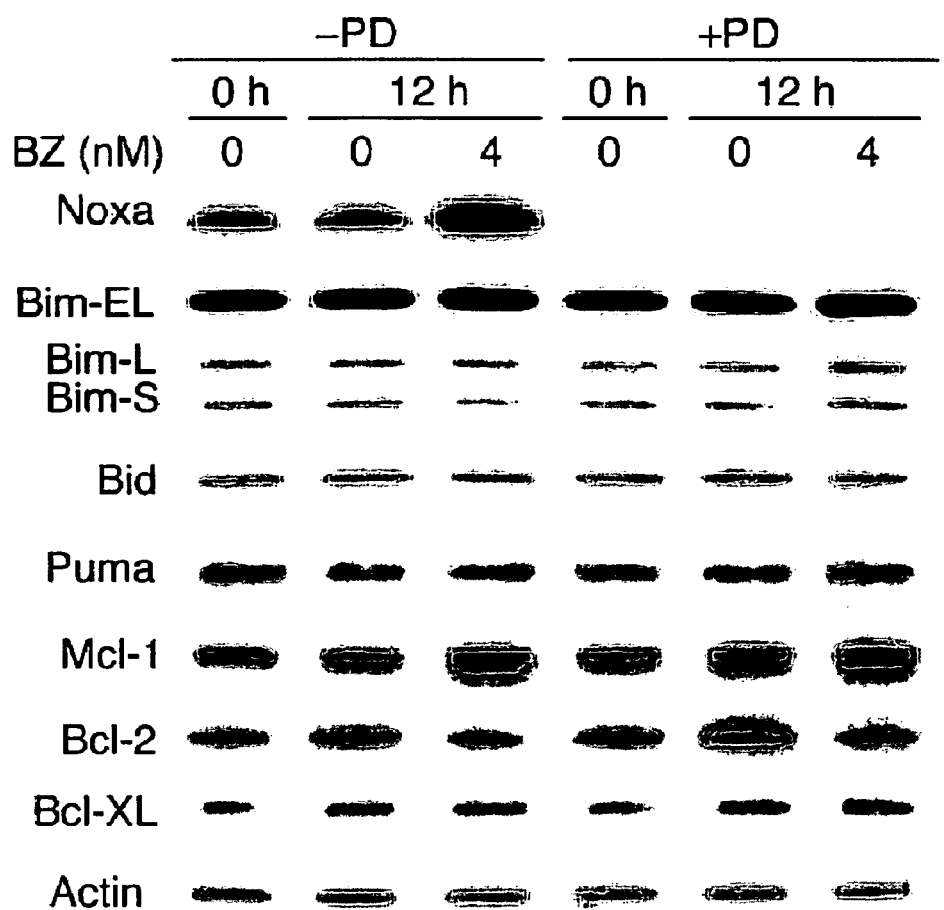

Bim Mediates Synergistic Killing by Neutralizing Mcl-1 and Bcl-2 in the Absence of Noxa Noxa, however, does not contribute to the induction of apoptosis by PD 0332991+bortezomib treatment (PD-B) because Noxa mRNA and protein were no longer detectable following PD 0332991-induced G1 arrest (FIGS. 7A-B). By contrast, Bim and MCL-1, but not Bcl-2, mRNAs were coordinately elevated by bortezomib and further by PD-B, whereas the control Rb mRNA remained unchanged (FIG. 7A). The prominent increases in Bim and Mcl-1 mRNAs were not mirrored by the modest increases in Bim isoforms by PD-B or in Mcl-1 protein by bortezomib (FIG. 7B), suggesting these proteins were kept in check with PD-B by rapid turnover. Consistent with this possibility, activation of ERK, which is known to promote Bim degradation (Ley et al., 2003) but not JNK, was modestly increased in PD-B, as was inhibition of NF-κB (data not shown). Nonetheless, the increases in Bim and Mcl-1 proteins were specific because other BH3-only (Puma and Bid) and anti-apoptotic (Bcl-2 and Bcl-xL) proteins did not vary appreciably (FIG. 7B).

Figure 7C:
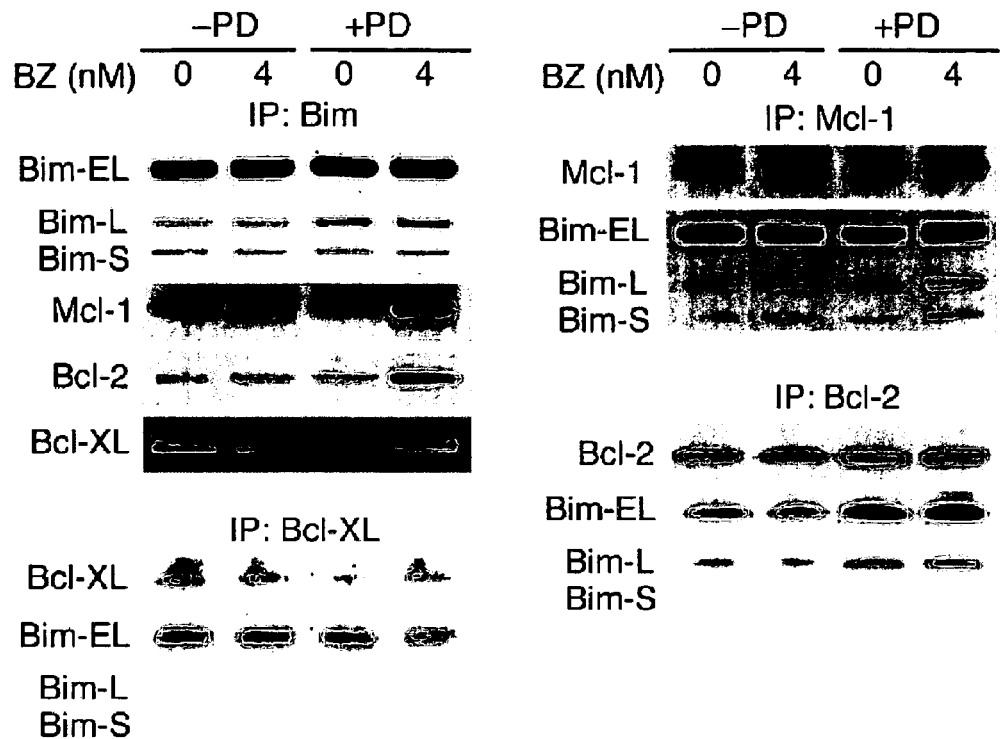
Figure 7D:
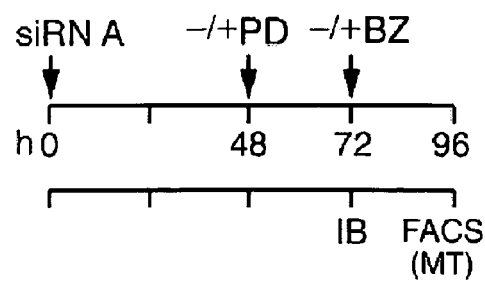
Figure 7E:
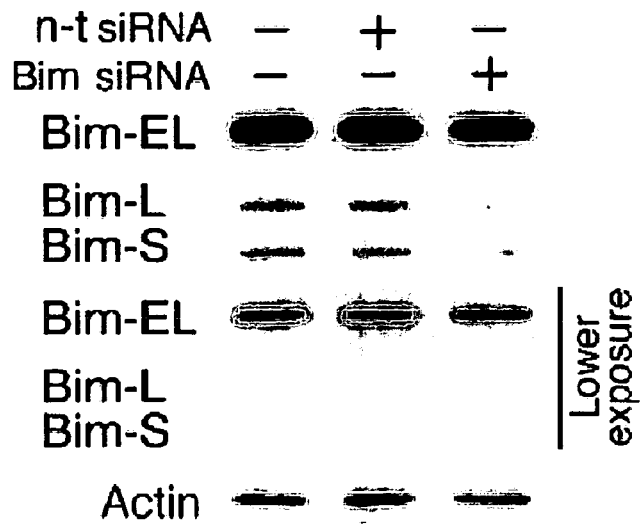
Figure 7F:
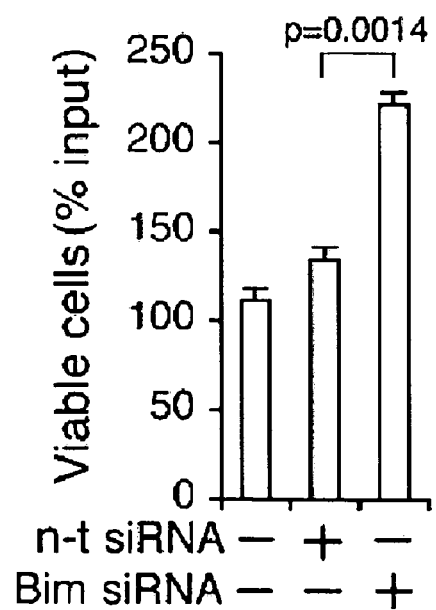
Figure 7G:
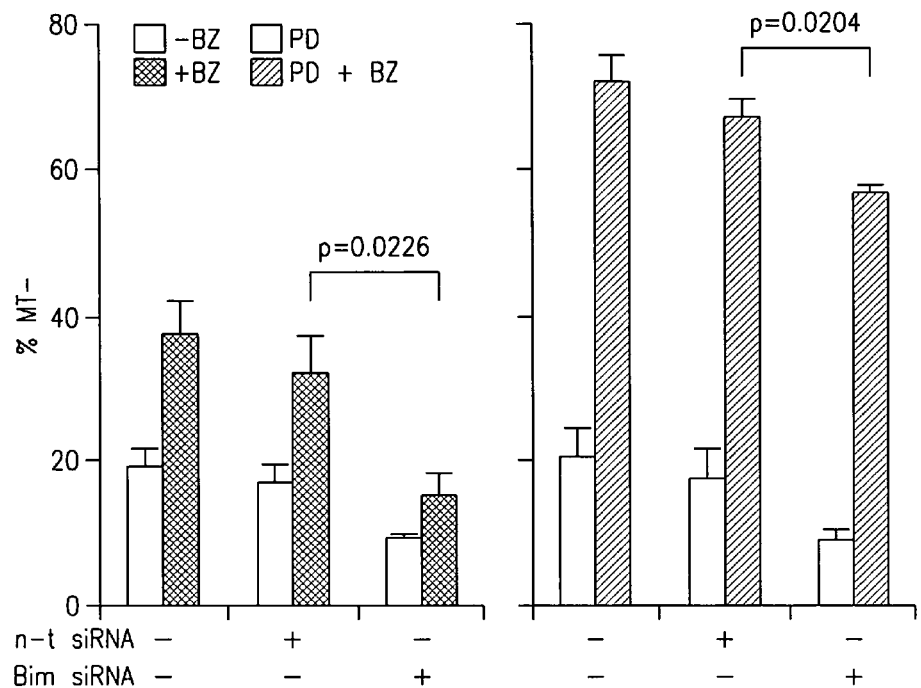

Bim is thought to mediate bortezomib killing of myeloma cells by neutralizing Mcl-1 and Bcl-2 (Gomez-Bougie et al., 2005). Reciprocal immunoprecipitation-immunoblotting revealed an increase in the association of Bim with Mcl-1 or Bcl-2, but not with Bcl-xL, in response to PD-B but not to either PD 0332991 or bortezomib (FIG. 7C). Confirming a role for Bim in the induction of apoptosis in PD-B, knocking down all three Bim isoforms by siRNA interference increased the viability and reduced MMD in myeloma cells, including those treated with PD 0332991 or bortezomib (FIG. 7D-F), or in combination when MMD was extensive (FIG. 7G). Taken together, these data indicate that Bim and Mcl-1 are coordinately increased upon disruption of IL-6 signaling and that through selective neutralization of Mcl-1 and Bcl-2, Bim mediates synergistic killing of myeloma cells by PD-B.

Figure 8A:
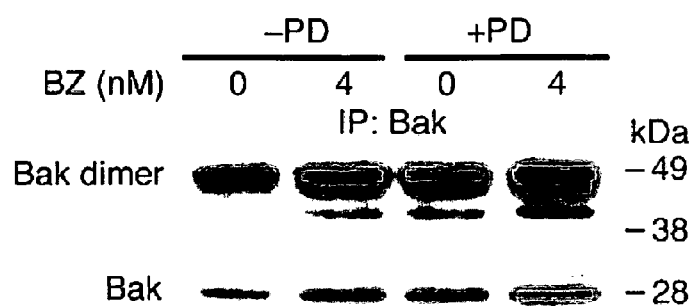
FIG. 8A—illustrates activation of Bak and release of Smac by PD 0332991-boretzomib in MM1.S cells incubated with bortezomib (4 nM) for 12 h after pretreatment with PD 0332991 (0.25 μM) for 24 h.
Figure 8B:
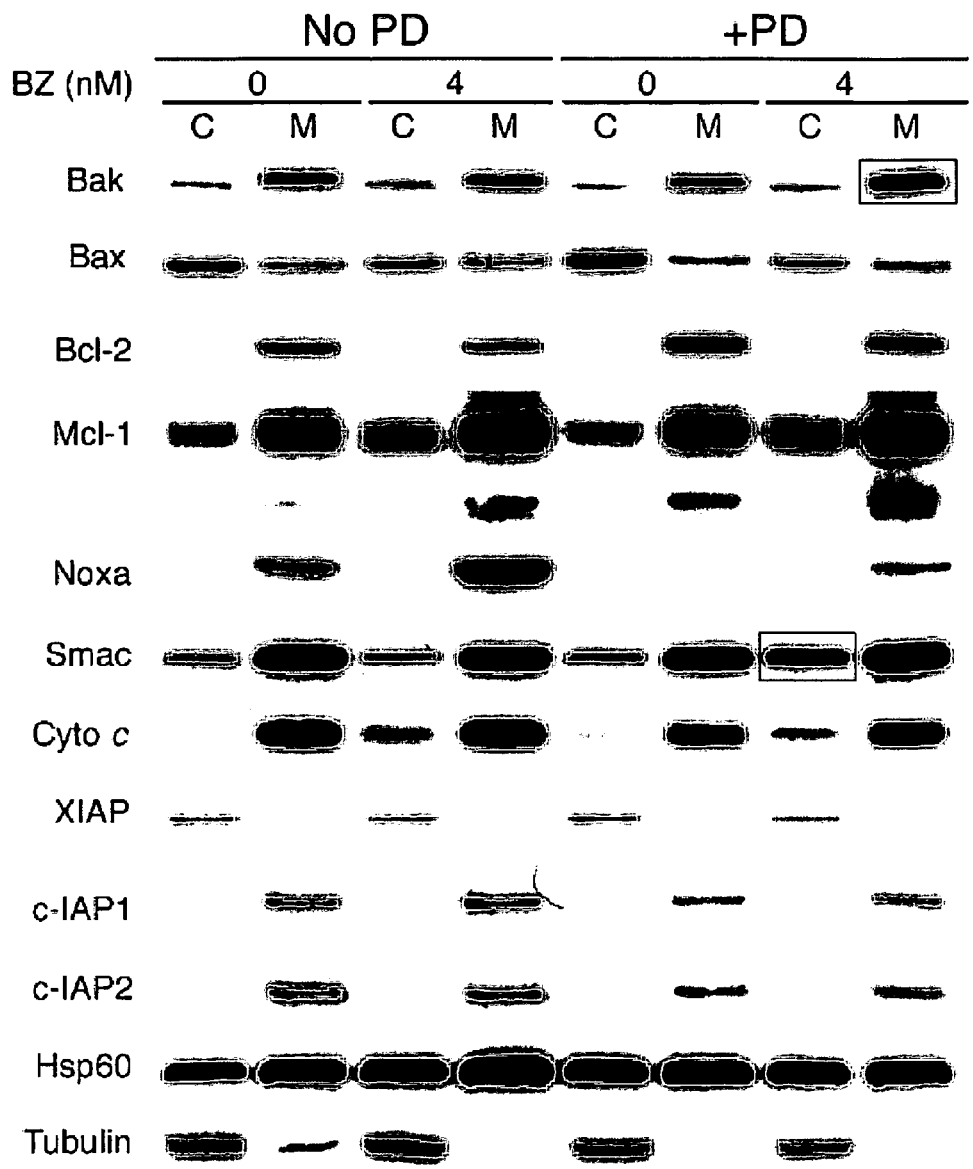
FIG. 8B shows an immunoblot of cellular proteins from these MM1.S cells where cytochrome c (Cyt c), Smac, Bcl-2-family and IAP-family were detected in cytosolic (C) or mitochondrial (M) fractions. 10 μg of protein was loaded in each lane. Tubulin and Hsp 60 were probed as loading controls for the cytosolic and the mitochondrial fraction, respectively. Data are representative of 4 independent experiments.

Preferential Activation of Bak and Release of Smac by Sustained G1 Arrest in Combination with Bortezomib Neutralization of Mcl-1 and Bcl-2 by Bim could lead to displacement and activation of the pro-apoptotic multi-domain Bak and Bax, which oligomerize on the outer mitochondrial membrane to increase membrane permeability and induce the release of apoptotic factors (Willis et al., 2005). Bak was appreciably increased and activated in myeloma cells, as evidenced by the enhanced formation of dimers (Willis et al., 2005) by 12 hours of bortezomib treatment following PD 0332991-induced G1 arrest (FIG. 8A). This correlated with enhanced association of Bak with the mitochondria, determined by immunoblotting of cytosolic extracts and membrane fractions enriched in intact mitochondria (at 6-fold cellular equivalent) (FIG. 8B). This was specific, because Bax remained predominantly localized to the cytosol, whereas Bcl-2, Mcl-1 and Noxa were largely associated with mitochondria, with Noxa being virtually absent in G1-arrested cells as expected (FIG. 8B).

Notably, the increase in the association of Bak with the mitochondrial membrane in PD-B was coincidental with enhanced release of the second mitochondrial-derived activator of caspase (Smac/DIABLO) (Du et al., 2000), but not cytochrome c (Cyto c) (Yang et al., 1997) (FIG. 8B). Smac relieves the inhibition of caspase activation by IAPs (inhibitors of apoptosis) (Roy et al., 1997), in part through binding to c-IAP1 and causing its rapid degradation (Yang and Du, 2004). Both c-IAP-1 and c-IAP-2, while marginally increased by bortezomib due to inhibition of proteasome-mediated degradation, were significantly reduced in G1-arrested MM1.S. cells, even in the presence of bortezomib. By contrast, the XIAP level did not vary (FIG. 8B). These data indicate that enhanced oligomerization of Bak on the mitochondrial membrane triggers synergistic mitochondrial membrane depolarization and preferential release of Smac, which, in concert with reduction of c-IAPs, promotes caspase activation in PD-B.

Summary

Through selective inhibition of CDK4 and CDK6 with PD 0332991, two novel strategies have been developed to target the cell cycle in order to prime myeloma cells for cytotoxic killing. In the first strategy, cytotoxic killing is enhanced by continuous inhibition of CDK4/6 with PD 0332991, which induces sustained cell cycle arrest in early G1 in the absence of apoptosis in myeloma cells (FIG. 1-2). While it is generally believed that non-cycling cells turn over more slowly than cycling cells under physiologic conditions, transformed cells seem to be exceptions to the rule. Myeloma cells become more vulnerable to cytotoxic killing when arrested in early G1, by either knocking down CDK4 and CDK6 expression by shRNA interference or inhibiting the CDK4/6 catalytic activity with PD 0332991 (FIG. 2). Synergistic killing was induced by exposure to bortezomib, briefly at a high concentration to simulate its rapid decay in vivo (Orlowski and Kuhn, 2008) or continuously at a sub-optimal concentration to rule out any off-target effect (FIGS. 1-2). It was also induced by other proteasome inhibitors and steroids with diverse mode of action also (FIG. 1-2 and data not shown). Priming of myeloma cells for cytotoxic killing by induction of sustained early G1 arrest, therefore, is likely rooted in the uncoupling of cellular function from cell cycle progression that results in lowering the threshold for apoptosis. This is particularly notable in the case of bortezomib, which preferentially kills myeloma cells during S phase entry (FIG. 2B) yet potently induces apoptosis at a sub-optimal concentration in early G1 in PD 0332991-treated myeloma cells, including primary bone marrow myeloma cells isolated from bortezomib-refractory patients (FIG. 2-4).

In the second strategy, removal of the G1 block induced by PD 0332991 leads to synchronous cell cycle progression and a dramatic increase in bortezomib killing in cells during G1-S transition or in S phase (FIG. 1 and data not shown). This suggests that myeloma cells are censored by apoptosis during G1-S transition. This apoptotic checkpoint is present in non-synchronized cells but does not extent to G2 or M phase of the cell cycle, given the loss of S phase cells and increase in the proportion of G2/M cells following bortezomib treatment (FIG. 2B). It is amplified by cell cycle synchronization, judging from the dramatic loss of cells in S, G2 and M in response to bortezomib (FIGS. 1E and 2B). Since the cytotoxic partners for targeting CDK4/6 may vary in myeloma and be specific for each disease, the selection of one or the other strategy for targeting CDK4/6 in combination therapy should take into consideration the cell cycle-specificity with which individual cytotoxic agents kill cancer cells and its interplay with the cell cycle-coupled apoptotic checkpoint.

The ability of PD 0332991 to induce exclusive and reversible G1 arrest in the absence of apoptosis (FIG. 1) further suggests that PD 0332991 is an ideal reagent for cell cycle synchronization. Genetic evidence indicated that CDK2 can compensate for the loss of both CDK4 and CDK6 in mouse embryonic fibroblasts to promote cell cycle entry and progression in response to serum stimulation (Malumbres et al., 2004). Induction of G1 arrest by inhibiting CDK4/6 demonstrates that the loss of CDK4/6 activity cannot be functionally compensated by CDK2 in myeloma cells. Possible explanations include a lack of compensatory increase in CDK2 or cyclin E, the marked elevation of p27$^{Kip1}$ (FIG. 2C and data not shown) and the intrinsic differences between embryonic and adult cells. However, optimal inhibition of CDK4/6 by PD 0332991 requires p18$^{INK4c}$, at least in antigen-activated, non-transformed primary B cells ex vivo (Baughn et al., 2006). It is not yet known whether this is the case in other cell types or transformed cells, or whether other INK4 CKIs can substitute for p18INK4c. Understanding the mechanism by which PD 0332991 cooperates with CKI and the cell type specificity should significantly advance studies of cell cycle coupled cellular function as well as targeting CDK4/6 in a clinical setting.

Figure 8C:
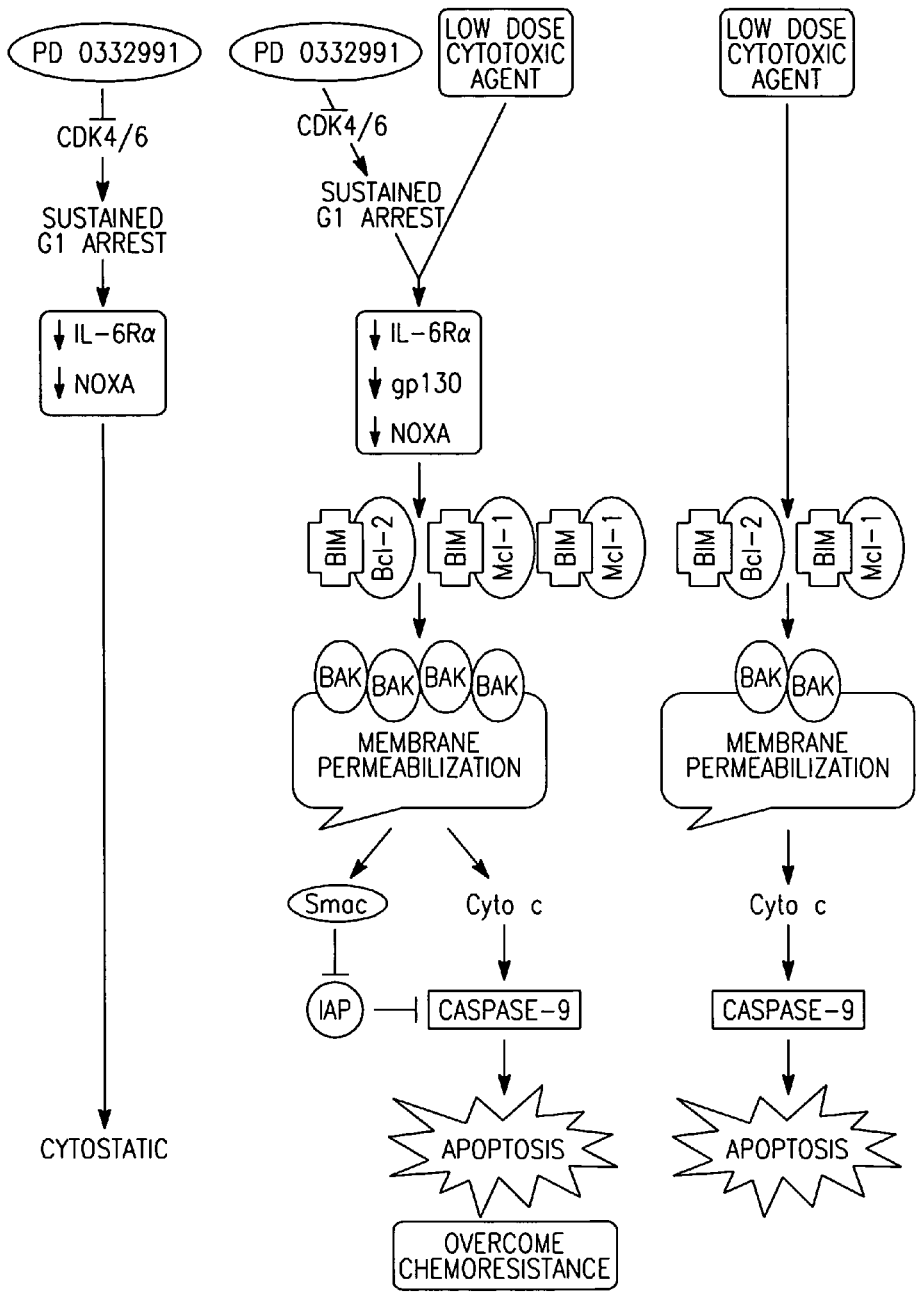
FIG. 8C is a schematic diagram illustrating the key events in synergistic induction of apoptosis by inhibition of CDK4 and CDK6 with PD 0332991 and induction of sustained G1 arrest in combination with induction of apoptosis by low dose cytotoxic agent.

The exceptional selectivity and potency with which PD 0332991 inhibits CDK4 and CDK6 further provides a unique system to address the coupling between the cell cycle and apoptosis. In this proof-of-concept study, we showed that induction of sustained early G1 arrest by PD 0332991 directs bortezomib to induce apoptosis in early G1, when bortezomib alone preferentially kills myeloma cells during S phase entry. Although induction of apoptosis by PD-B and bortezomib converge in mitochondrial dysfunction and caspase activation, the two pathways are distinct in part due to cell cycle-specific gene expression (FIG. 8C).

First, induction of early G1 arrest leads to coordinated suppression of surface IL-6Rα expression and reduction of Stat3, and primes myeloma cells for synergistic loss of surface gp130 in response to suboptimal concentration bortezomib (FIG. 6). The precise mechanism of IL-6Rα and gp130 regulation in G1 remains to be defined, but post-transcriptional regulation appears to play a major role (data not shown). gp130 has been reported to be cleaved by caspase in response to higher doses of bortezomib (Hideshima et al., 2003). However, synergistic reduction of surface gp130 in PD-B precedes significant caspase activation (data not shown) and knocking down gp130 expression activates the apoptosis pathway induced by PD-B (FIG. 6). On this basis, it is tempting to postulate that the impairment of IL-6 signaling is an early event in PD-B that triggers synergistic induction of apoptosis in the IL-6-rich bone marrow microenvironment. IL-6 is critical for the survival of cancer cells in general, gp130 is also a co-receptor for other cytokines such as oncostatin M and Stat3 mediates the signals of a large number of cytokines and growth factors. Cell cycle control of gp130 and Stat3 signaling may therefore have broader implications for the coupling of the cell cycle to apoptosis in cancer cells as well as non-transformed cells.

Second, genes of the Bcl-2 family are differentially regulated by the cell cycle. One prominent example is the silencing of Noxa RNA synthesis in early G1 arrest induced by PD 0332991, which overrides the increase of Noxa RNA by bortezomib and precludes a role for Noxa in mediating synergistic killing by PD-B (FIGS. 7-8C). By contrast, the increase in Bim and Mcl-1 RNA in response to bortezomib is markedly augmented in PD-B, which contributes to the enhanced neutralization of Mcl-1 by Bim in PD-B (FIG. 7). PD-B modestly augments bortezomib activation of Erk and inhibition of NF-κB (FIG. 6), in line with reduction of cyclin D2, a target of both pathways, and the absence of TNF-α and TRAIL that activate NF-κB (FIGS. 2 and 6). Activation of Bim RNA synthesis in PD-B appears to be mediated by the transcription factor C/EBP (data not shown), but the pathways linking early G1 arrest and impairment of IL-6 signaling to differential regulation of Noxa and Bim remain to be determined.

Third, induction of early G1 arrest leads to enhanced activation of Bak and association of Bak with the mitochondrial membrane as well as preferential release of SMAC and reduction of c-IAP, in contrast to the enhancement of Bax association with the mitochondrial membrane and preferential release of cytochrome c by boretezomib (FIG. 8A). Accordingly, synergistic induction of apoptosis by PD-B is further augmented by Smac-mimetics (Huang and Chen-Kiang unpublished).

Most importantly, induction of sustained early G1 arrest sensitizes primary bone marrow myeloma cells isolated from bortezomib-refractory patients to killing by low dose bortezomib and other cytotoxic agents (FIG. 3-4 and data not shown). Induction of synergistic killing is mediated by caspase activation and sustained in the presence of BMSCs (FIGS. 3-4 and 6A), suggesting that synergistic killing by PD-B is likely relevant in vivo. While it is not feasible to determine whether PD-B killing of primary BMMs is augmented further by induction of synchronous cell cycle progression due to limited proliferation ex vivo, we have addressed this possibility in two preclinical animal models. We demonstrated by BLI that treatment with a suboptimal concentration of bortezomib during G1 arrest induced by PD 0332991 and again during synchronous cell cycle progression led to synergistic suppression of human myeloma tumor development in a NOD/SCID xenograft model (FIG. 5). In a complementary study, we show in the immuno-competent 5T33 mouse myeloma model that sequential induction of G1 arrest and bortezmib treatment prolonged the survival of mice developing aggressive myeloma (Menu et al., 2008). Given that inhibition of cell proliferation by PD 0332991 is tissue-specific in mice (Ramsey et al., 2007), the tumor and cell type specificity are important considerations for targeting CDK4/6 with PD 0332991 in combination with cytotoxic killing.

On the basis of the superior selectivity, oral bioavailability and low toxicity of PD 0332991 and the novel approaches we have developed in this study, a proof-of-concept phaseI/II clinical trial targeting CDK4 and CDK6 in combination with bortezomib and dexamethasone is in progress in multiple myeloma. Already, preliminary data have validated that PD 0332991 completely inhibits CDK4 and CDK6 and halts tumor cell division within the tolerable dose in humans (data not shown). Mechanism-based targeting of CDK4/6 in combination therapy, therefore, may have significant therapeutic benefit for multiple myeloma and potentially other cancers.

Example 3

Inhibition of CDK4/6 by PD 0332991 Results in Abrogation of Osteoclast Formation This Example describes preliminary results on tests performed to ascertain whether PD 0332991, alone and in combination with bortezomib, may inhibit osteoclastogenesis.

Non-adherent mononuclear bone marrow cells from multiple myeloma patients were cultured in the presence of macrophage colony stimulating factor (M-CSF) and Receptor Activator for Nuclear Factor κB lingand (RANKL) for three weeks.

Treatment of human osteoclast cultures with PD 0332991 for 3 weeks decreased osteoclast formation in a dose-dependent manner with an $IC_{50}$ of 50 nM. The combination of PD 0332991 and bortezomib led to synergistic inhibition of osteoclast formation, and completely abrogated osteoclastogenesis using only low doses of PD 0332991 (25 nM) and bortezomib (2 nM). A time course study of PD 0332991 treatment indicated that a first week, but not second or the third week, was sufficient to inhibit osteoclast formation.

PD 0332991 is the only known selective inhibitor of CDK4 and CDK6, which at concentration below 5 uM does not cross react with at least 38 kinases or when used alone does not induce apoptosis. Taken together, these data indicate that by inducing G1 arrest and inhibiting progenitor expansion, PD 0332991 is a powerful and selective inhibitor for osteoclastogenesis. Therefore, targeting CDK4/6 with PD 0332291 in combination therapy is a promising therapeutic strategy to improve bone integrity in multiple myeloma patients.

REFERENCES

Adams, J., and Kauffman, M. (2004). Development of the proteasome inhibitor Velcade (Bortezomib). Cancer Invest 22, 304-311.

Adams, J. M., and Cory, S. (2007). The Bcl-2 apoptotic switch in cancer development and therapy. Oncogene 26, 1324-1337.

Altmeyer, A., Simmons, R. C., Krajewski, S., Reed, J. C., Bornkamm, G. W., and Chen-King, S. (1997). Reversal of EBV immortalization precedes apoptosis in IL-6-induced human B cell terminal differentiation. Immunity 7, 667-677.

Baughn, L. B., Di Liberto, M., Wu, K., Toogood, P. L., Louie, T., Gottschalk, R., Niesvizky, R., Cho, H., Ely, S., Moore, M. A., et al. (2006). A novel orally active small molecule potently induces G1 arrest in primary myeloma cells and prevents tumor growth by specific inhibition of cyclin-dependent kinase 4/6. Cancer Research 66, 7661-7667.

Chauhan, D., Uchiyama, H., Akbarali, Y., Urashima, M., Yamamoto, K., Libermann, T. A., and Anderson, K. C. (1996). Multiple myeloma cell adhesion-induced interleukin-6 expression in bone marrow stromal cells involves activation of NF-kappa B. Blood 87, 1104-1112.

Chen-Kiang, S. (2003). Cell-cycle control of plasma cell differentiation and tumorigenesis. Immunol Rev 194, 39-47.

Chesi, M., Bergsagel, P. L., Brents, L. A., Smith, C. M., Gerhard, D. S., and Kuehl, W. M. (1996). Dysregulation of cyclin D1 by translocation into an IgH gamma switch region in two multiple myeloma cell lines. Blood 88, 674-681.

Dib, A., Peterson, T. R., Raducha-Grace, L., Zingone, A., Zhan, F., Hanamura, I., Barlogie, B., Shaughnessy, J., Jr., and Kuehl, W. M. (2006). Paradoxical expression of INK4c in proliferative multiple myeloma tumors: bi-allelic deletion vs increased expression. Cell Div 1, 23.

Dijkers, P. F., Medema, R. H., Lammers, J. W., Koenderman, L., and Coffer, P. J. (2000). Expression of the pro-apoptotic Bcl-2 family member Bim is regulated by the forkhead transcription factor FKHR-L1. Curr Biol 10, 1201-1204.

Du, C., Fang, M., Li, Y., Li, L., and Wang, X. (2000). Smac, a mitochondrial protein that promotes cytochrome c-dependent caspase activation by eliminating IAP inhibition. Cell 102, 33-42.

Durie, B. G. (1986). Staging and kinetics of multiple myeloma. Semin Oncol 13, 300-309.

Ely, S. A., Di Liberto*, M., Niesvizky, R., Baughn, L. B., Cho, H., Hatada, E., Knowles, D. M., Lane, J., and Chen-Kiang, S. (2005). Mutually exclusive Cdk-4-Cyclin D1 and Cdk6-Cyclin D2 pairing inactivates Rb and promotes cell cycle dysregulation in multiple myeloma (*equal contribution). Cancer Research 65, 11345-11353.

Franklin, D. S., Godfrey, V. L., Lee, H., Kovalev, G. I., Schoonhoven, R., Chen-Kiang, S., Su, L., and Xiong, Y.

(1998). CDK inhibitors p18(INK4c) and p27(Kip1) mediate two separate pathways to collaboratively suppress pituitary tumorigenesis. Genes & Development 12, 2899-2911.

Fry, D. W., Harvey, P. J., Keller, P. R., Elliott, W. L., Meade, M., Trachet, E., Albassam, M., Zheng, X., Leopold, W. R., Pryer, N. K., et al. (2004). Specific inhibition of cyclin-dependent kinase 4/6 by PD 0332991 and associated antitumor activity in human tumor xenografts. Molecular Cancer Therapeutics 3, 1427-1438.

Gomez-Bougie, P., Bataille, R., and Amiot, M. (2004). The imbalance between Bim and Mcl-1 expression controls the survival of human myeloma cells. Eur J Immunol 34, 3156-3164.

Gomez-Bougie, P., Bataille, R., and Amiot, M. (2005). Endogenous association of Bim BH3-only protein with Mcl-1, Bcl-xL and Bcl-2 on mitochondria in human B cells. Eur J Immunol 35, 971-976.

Gomez-Bougie, P., Wuilleme-Toumi, S., Menoret, E., Trichet, V., Robillard, N., Philippe, M., Bataille, R., and Amiot, M. (2007). Noxa up-regulation and Mcl-1 cleavage are associated to apoptosis induction by bortezomib in multiple myeloma. Cancer Research 67, 5418-5424.

Guan, K. L., Jenkins, C. W., Li, Y., Nichols, M. A., Wu, X., O'Keefe, C. L., Matera, A. G., and Xiong, Y. (1994). Growth suppression by p18, a p16INK4/MTS1- and p14INK4B/MTS2-related CDK6 inhibitor, correlates with wild-type pRb function. Genes & Development 8, 2939-2952.

Hideshima, T., Chauhan, D., Hayashi, T., Akiyama, M., Mitsiades, N., Mitsiades, C., Podar, K., Munshi, N. C., Richardson, P. G., and Anderson, K. C. (2003). Proteasome inhibitor PS-341 abrogates IL-6 triggered signaling cascades via caspase-dependent downregulation of gp130 in multiple myeloma. Oncogene 22, 8386-8393.

Hideshima, T., Richardson, P., Chauhan, D., Palombella, V. J., Elliott, P. J., Adams, J., and Anderson, K. C. (2001). The proteasome inhibitor PS-341 inhibits growth, induces apoptosis, and overcomes drug resistance in human multiple myeloma cells. Cancer Research 61, 3071-3076.

Hirai, H., Roussel, M. F., Kato, J. Y., Ashmun, R. A., and Sherr, C. J. (1995). Novel INK4 proteins, p19 and p18, are specific inhibitors of the cyclin D-dependent kinases CDK4 and CDK6. Mol Cell Biol 15, 2672-2681.

Huang, X., Di Liberto, M., Cunningham, A. F., Kang, L., Cheng, S., Ely, S., Liou, H. C., Maclennan, I. C., and Chen-Kiang, S. (2004). Homeostatic cell-cycle control by BLyS: Induction of cell-cycle entry but not G1/S transition in opposition to p18INK4c and p27Kip1. Proc Natl Acad Sci USA 101, 17789-17794.

Jeffrey, P. D., Tong, L., and Pavletich, N. P. (2000). Structural basis of inhibition of CDK-cyclin complexes by INK4 inhibitors. Genes & Development 14, 3115-3125.

Landis, M. W., Pawlyk, B. S., Li, T., Sicinski, P., and Hinds, P. W. (2006). Cyclin D1-dependent kinase activity in murine development and mammary tumorigenesis. Cancer Cell 9, 13-22.

Ley, R., Balmanno, K., Hadfield, K., Weston, C., and Cook, S. J. (2003). Activation of the ERK1/2 signaling pathway promotes phosphorylation and proteasome-dependent degradation of the BH3-only protein, Bim. J Biol Chem 278, 18811-18816.

Lu, H., and Schulze-Gahmen, U. (2006). Toward understanding the structural basis of cyclin-dependent kinase 6 specific inhibition. Journal of medicinal chemistry 49, 3826-3831.

Malumbres, M., and Barbacid, M. (2007). Cell cycle kinases in cancer. Current Opinion in Genetics & Development 17, 60-65.

Malumbres, M., Pevarello, P., Barbacid, M., and Bischoff, J. R. (2008). CDK inhibitors in cancer therapy: what is next? Trends in Pharmacological Sciences 29, 16-21.

Malumbres, M., Sotillo, R., Santamaria, D., Galan, J., Cerezo, A., Ortega, S., Dubus, P., and Barbacid, M. (2004). Mammalian cells cycle without the D-type cyclin-dependent kinases Cdk4 and Cdk6. Cell 118, 493-504.

Marzec, M., Kasprzycka, M., Lai, R., Gladden, A. B., Wlodarski, P., Tomczak, E., Nowell, P., Deprimo, S. E., Sadis, S., Eck, S., et al. (2006). Mantle cell lymphoma cells express predominantly cyclin D1a isoform and are highly sensitive to selective inhibition of CDK4 kinase activity. Blood 108, 1744-1750.

Menu, E., Garcia, J., Huang, X., Di Liberto, M., Toogood, P. L., Chen, I., Vanderkerken, K., and Chen-Kiang, S. (2008). A novel therapeutic combination using PD 0332991 and bortezomib: study in the 5T33MM myeloma model. Cancer Research 68, 5519-5523.

Morse, L., Chen, D., Franklin, D., Xiong, Y., and Chen-Kiang, S. (1997). Induction of cell cycle arrest and B cell terminal differentiation by CDK inhibitor p18(INK4c) and IL-6. Immunity 6, 47-56.

Ng, M. H., Chung, Y. F., Lo, K. W., Wickham, N. W., Lee, J. C., and Huang, D. P. (1997). Frequent hypermethylation of p16 and p15 genes in multiple myeloma. Blood 89, 2500-2506.

Orlowski, R. Z., and Kuhn, D. J. (2008). Proteasome inhibitors in cancer therapy: lessons from the first decade. Clin Cancer Res 14, 1649-1657.

Petersen, S. L., Wang, L., Yalcin-Chin, A., Li, L., Peyton, M., Minna, J., Harran, P., and Wang, X. (2007). Autocrine TNFalpha signaling renders human cancer cells susceptible to Smac-mimetic-induced apoptosis. Cancer Cell 12, 445-456.

Puthalakath, H., O'Reilly, L. A., Gunn, P., Lee, L., Kelly, P. N., Huntington, N. D., Hughes, P. D., Michalak, E. M., McKimm-Breschkin, J., Motoyama, N., et al. (2007). ER stress triggers apoptosis by activating BH3-only protein Bim. Cell 129, 1337-1349.

Qin, J. Z., Ziffra, J., Stennett, L., Bodner, B., Bonish, B. K., Chaturvedi, V., Bennett, F., Pollock, P. M., Trent, J. M., Hendrix, M. J., et al. (2005). Proteasome inhibitors trigger NOXA-mediated apoptosis in melanoma and myeloma cells. Cancer Research 65, 6282-6293.

Ramsey, M. R., Krishnamurthy, J., Pei, X. H., Torrice, C., Lin, W., Carrasco, D. R., Ligon, K. L., Xiong, Y., and Sharpless, N. E. (2007). Expression of p16Ink4a compensates for p18Ink4c loss in cyclin-dependent kinase 4/6-dependent tumors and tissues. Cancer Research 67, 4732-4741.

Richardson, P. G., Mitsiades, C., Hideshima, T., and Anderson, K. C. (2006). Bortezomib: proteasome inhibition as an effective anticancer therapy. Annual Review of Medicine 57, 33-47.

Roecklein, B. A., and Torok-Storb, B. (1995). Functionally distinct human marrow stromal cell lines immortalized by transduction with the human papilloma virus E6/E7 genes. Blood 85, 997-1005.

Roy, N., Deveraux, Q. L., Takahashi, R., Salvesen, G. S., and Reed, J. C. (1997). The c-IAP-1 and c-IAP-2 proteins are direct inhibitors of specific caspases. Embo J 16, 6914-6925.

Shaughnessy, J., Jr., Gabrea, A., Qi, Y., Brents, L., Zhan, F., Tian, E., Sawyer, J., Barlogie, B., Bergsagel, P. L., and Kuehl, M. (2001). Cyclin D3 at 6p21 is dysregulated by recurrent chromosomal translocations to immunoglobulin loci in multiple myeloma. Blood 98, 217-223.

Sherr, C. J., and Roberts, J. M. (1999). CDK inhibitors: positive and negative regulators of G1-phase progression. Genes & Development 13, 1501-1512.

Slee, E. A., Harte, M. T., Kluck, R. M., Wolf, B. B., Casiano, C. A., Newmeyer, D. D., Wang, H. G., Reed, J. C., Nicholson, D. W., Alnemri, E. S., et al. (1999). Ordering the cytochrome c-initiated caspase cascade: hierarchical activation of caspases-2, -3, -6, -7, -8, and -10 in a caspase-9-dependent manner. The Journal of Cell Biology 144, 281-292.

Tourigny, M. R., Ursini-Siegel, J., Lee, H., Toellner, K. M., Cunningham, A. F., Franklin, D. S., Ely, S., Chen, M., Qin, X. F., Xiong, Y., et al. (2002). CDK inhibitor p18(INK4c) is required for the generation of functional plasma cells. Immunity 17, 179-189.

Varfolomeev, E., Blankenship, J. W., Wayson, S. M., Fedorova, A. V., Kayagaki, N., Garg, P., Zobel, K., Dynek, J. N., Elliott, L. O., Wallweber, H. J., et al. (2007). IAP antagonists induce autoubiquitination of c-IAPB, NF-kappaB activation, and TNFalpha-dependent apoptosis. Cell 131, 669-681.

Vince, J. E., Wong, W. W., Khan, N., Feltham, R., Chau, D., Ahmed, A. U., Benetatos, C. A., Chunduru, S. K., Condon, S. M., McKinlay, M., et al. (2007). IAP antagonists target cIAP1 to induce TNFalpha-dependent apoptosis. Cell 131, 682-693.

Wang, L., Wang, J., Blaser, B. W., Duchemin, A. M., Kusewitt, D. F., Liu, T., Caligiuri, M. A., and Briesewitz, R. (2007). Pharmacologic inhibition of CDK4/6: mechanistic evidence for selective activity or acquired resistance in acute myeloid leukemia. Blood 110, 2075-2083.

Weir, B. A., Woo, M. S., Getz, G., Perner, S., Ding, L., Beroukhim, R., Lin, W. M., Province, M. A., Kraja, A., Johnson, L. A., et al. (2007). Characterizing the cancer genome in lung adenocarcinoma. Nature 450, 893-898.

Wiedemeyer, R., Brennan, C., Heffernan, T. P., Xiao, Y., Mahoney, J., Protopopov, A., Zheng, H., Bignell, G., Furnari, F., Cavenee, W. K., et al. (2008). Feedback circuit among INK4 tumor suppressors constrains human glioblastoma development. Cancer Cell 13, 355-364.

Willis, S. N., Chen, L., Dewson, G., Wei, A., Naik, E., Fletcher, J. I., Adams, J. M., and Huang, D. C. (2005). Proapoptotic Bak is sequestered by Mcl-1 and Bcl-xL, but not Bcl-2, until displaced by BH3-only proteins. Genes & Development 19, 1294-1305.

Wu, K. D., Cho, Y. S., Katz, J., Ponomarev, V., Chen-Kiang, S., Danishefsky, S. J., and Moore, M. A. (2005). Investigation of antitumor effects of synthetic epothilone analogs in human myeloma models in vitro and in vivo. Proc Natl Acad Sci USA 102, 10640-10645.

Yang, J., Liu, X., Bhalla, K., Kim, C. N., Ibrado, A. M., Cai, J., Peng, T. I., Jones, D. P., and Wang, X. (1997). Prevention of apoptosis by Bcl-2: release of cytochrome c from mitochondria blocked. Science 275, 1129-1132.

Yang, Q. H., and Du, C. (2004). Smac/DIABLO selectively reduces the levels of c-IAP1 and c-IAP2 but not that of XIAP and livin in HeLa cells. J Biol Chem 279, 16963-16970.

Yu, Q., Sicinska, E., Geng, Y., Ahnstrom, M., Zagozdzon, A., Kong, Y., Gardner, H., Kiyokawa, H., Harris, L. N., Stal, O., et al. (2006). Requirement for CDK4 kinase function in breast cancer. Cancer Cell 9, 23-32.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "an antibody" includes a plurality (for example, a solution of antibodies or a series of antibody preparations) of such antibodies, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A method of treating or inducing remission of drug-resistant cancer or tumors in a mammal comprising:
   (a) administering PD 0332991 to the mammal for several days to several weeks;
   (b) periodically administering one or more chemotherapeutic agents, or radiation, to the mammal after at least three (3) days of administration of the PD 0332991;
   (c) temporarily terminating administration of the PD 0332991 after the several days to several weeks so that cancer or tumor cells in the mammal enter S phase synchronously;
   (d) repeating the administration of the PD 0332991 to the mammal for several days to several weeks; and
   (e) repeating the periodic administration of the one or more chemotherapeutic agents, or radiation;
   to thereby induce remission of the drug-resistant cancer or tumor in the mammal with fewer side effects than when the chemotherapeutic agent is administered without administration of the PD 0332991.

2. The method of claim 1, wherein the method is repeated until remission of the cancer and/or tumor.

3. The method of claim 1, wherein the PD 0332991 and the one or more chemotherapeutic agents are administered in an amount sufficient to induce apoptosis in the cancer and/or tumor cells in the mammal.

4. The method of claim 1, wherein one or more chemotherapeutic agents is administered and the one or more chemotherapeutic agents are selected from the group consisting of a proteasome inhibitor, cytotoxic agent, photosensitizing agent, folate antagonist, pyrimidine antimetabolite, purine antimetabolite, 5-aminolevulinic acid, alkylating agent, platinum anti-tumor agent, anthracycline, DNA intercalator, epipodophyllotoxin, DNA topoisomerase inhibitor, microtubule-targeting agent, vinca alkaloid, SMAC mimetic, taxane, epothilone, an asparaginase or a combination thereof.

5. The method of claim 1, wherein the chemotherapeutic agent is bortezomib, CEP 18770, carfilzomib, cytosine arabinoside or a combination thereof.

6. The method of claim 1, wherein the cancer or tumors in the mammal are resistant to more than one chemotherapeutic agent.

7. The method of claim 1, wherein the cancer and/or tumor comprises retinoblastoma-mediated cancer and/or tumor cells.

8. The method of claim 1, wherein the cancer and/or tumor comprises hematopoietic/blood cancer cells.

9. The method of claim 1, wherein the cancer and/or tumor is mantle cell lymphoma, diffused large B cell lymphoma, acute myeloid leukemia, chronic lymphatic leukemia, chronic myelocytic leukemia, polycythemia vera, malignant lymphoma, multiple myeloma, Hodgkin's lymphoma, non-Hodgkin's lymphoma or a combination thereof.

10. The method of claim 1, wherein the method induces apoptosis in cancer or tumors cells.

11. The method of claim 1, wherein the method also inhibits osteoclast differentiation.

12. The method of claim 1, wherein the amount of chemotherapeutic agent administered is lower than that used when the PD 0332991 is not administered.

* * * * *

SEQUENCE LISTING

<160> NUMBER OF SEQ ID NOS: 7

<210> SEQ ID NO 1
<211> LENGTH: 1474
<212> TYPE: DNA
<213> ORGANISM: Homo sapiens

<400> SEQUENCE: 1

| | | | | | |
|---|---|---|---|---|---|
| agccctccca | gtttccgcgc | gcctctttgg | cagctggtca | catggtgagg | gtggggtga    60 |
| ggggggcctct | ctagcttgcg | gcctgtgtct | atggtcgggc | cctctgcgtc | cagctgctcc  120 |
| ggaccgagct | cgggtgtatg | gggccgtagg | aaccggctcc | ggggccccga | taacgggccg  180 |
| cccccacagc | accccgggct | ggcgtgaggg | tctcccttga | tctgagaatg | gctacctctc  240 |
| gatatgagcc | agtggctgaa | attggtgtcg | gtgcctatgg | gacagtgtac | aaggcccgtg  300 |
| atccccacag | tggccacttt | gtggccctca | agagtgtgag | agtccccaat | ggaggaggag  360 |
| gtggaggagg | ccttcccatc | agcacagttc | gtgaggtggc | tttactgagg | cgactggagg  420 |
| cttttgagca | tcccaatgtt | gtccggctga | tggacgtctg | tgccacatcc | gaactgacc   480 |
| gggagatcaa | ggtaaccctg | gtgtttgagc | atgtagacca | ggacctaagg | acatatctgg  540 |
| acaaggcacc | cccaccaggc | ttgccagccg | aaacgatcaa | ggatctgatg | cgccagtttc  600 |
| taagaggcct | agatttcctt | catgccaatt | gcatcgttca | ccgagatctg | aagccagaga  660 |
| acattctggt | gacaagtggt | ggaacagtca | agctggctga | ctttggcctg | ccagaatct   720 |
| acagctacca | gatggcactt | acacccgtgg | ttgttacact | ctggtaccga | gctcccgaag  780 |
| ttcttctgca | gtccacatat | gcaacacctg | tggacatgtg | gagtgttggc | tgtatctttg  840 |
| cagagatgtt | tcgtcgaaag | cctctcttct | gtggaaactc | tgaagccgac | cagttgggca  900 |
| aaatctttga | cctgattggg | ctgcctccag | aggatgactg | gcctcgagat | gtatccctgc  960 |
| cccgtggagc | ctttcccccc | agagggcccc | gcccagtgca | gtcggtggta | cctgagatgg 1020 |
| aggagtcggg | agcacagctg | ctgctggaaa | tgctgacttt | taacccacac | aagcgaatct 1080 |
| ctgcctttcg | agctctgcag | cactcttatc | tacataagga | tgaaggtaat | ccggagtgag 1140 |
| caatggagtg | gctgccatgg | aaggaagaaa | agctgccatt | tcccttctgg | acactgagag 1200 |
| ggcaatcttt | gcctttatct | ctgaggctat | ggagggtcct | cctccatctt | tctacagaga 1260 |
| ttactttgct | gccttaatga | cattcccctc | ccacctctcc | ttttgaggct | tctccttctc 1320 |
| cttcccattt | ctctacacta | aggggtatgt | tccctcttgt | ccctttccct | acctttatat 1380 |
| ttggggtcct | tttttataca | ggaaaaacaa | aacaaagaaa | taatggtctt | ttttttttt  1440 |
| ttaaaaaaaa | aaaaaaaaaa | aaaaaaaaaa | aaaa | | 1474 |

<210> SEQ ID NO 2
<211> LENGTH: 303
<212> TYPE: PRT
<213> ORGANISM: Homo sapiens

<400> SEQUENCE: 2

Met Ala Thr Ser Arg Tyr Glu Pro Val Ala Glu Ile Gly Val Gly Ala
 1               5                  10                  15

Tyr Gly Thr Val Tyr Lys Ala Arg Asp Pro His Ser Gly His Phe Val
            20                  25                  30

Ala Leu Lys Ser Val Arg Val Pro Asn Gly Gly Gly Gly Gly Gly Gly
        35                  40                  45

Leu Pro Ile Ser Thr Val Arg Glu Val Ala Leu Leu Arg Arg Leu Glu
    50                  55                  60

```
Ala Phe Glu His Pro Asn Val Val Arg Leu Met Asp Val Cys Ala Thr
 65                  70                  75                  80

Ser Arg Thr Asp Arg Glu Ile Lys Val Thr Leu Val Phe Glu His Val
                 85                  90                  95

Asp Gln Asp Leu Arg Thr Tyr Leu Asp Lys Ala Pro Pro Gly Leu
            100                 105                 110

Pro Ala Glu Thr Ile Lys Asp Leu Met Arg Gln Phe Leu Arg Gly Leu
            115                 120                 125

Asp Phe Leu His Ala Asn Cys Ile Val His Arg Asp Leu Lys Pro Glu
    130                 135                 140

Asn Ile Leu Val Thr Ser Gly Gly Thr Val Lys Leu Ala Asp Phe Gly
145                 150                 155                 160

Leu Ala Arg Ile Tyr Ser Tyr Gln Met Ala Leu Thr Pro Val Val
                165                 170                 175

Thr Leu Trp Tyr Arg Ala Pro Glu Val Leu Leu Gln Ser Thr Tyr Ala
            180                 185                 190

Thr Pro Val Asp Met Trp Ser Val Gly Cys Ile Phe Ala Glu Met Phe
            195                 200                 205

Arg Arg Lys Pro Leu Phe Cys Gly Asn Ser Glu Ala Asp Gln Leu Gly
210                 215                 220

Lys Ile Phe Asp Leu Ile Gly Leu Pro Pro Glu Asp Asp Trp Pro Arg
225                 230                 235                 240

Asp Val Ser Leu Pro Arg Gly Ala Phe Pro Pro Arg Gly Pro Arg Pro
                245                 250                 255

Val Gln Ser Val Val Pro Glu Met Glu Ser Gly Ala Gln Leu Leu
            260                 265                 270

Leu Glu Met Leu Thr Phe Asn Pro His Lys Arg Ile Ser Ala Phe Arg
        275                 280                 285

Ala Leu Gln His Ser Tyr Leu His Lys Asp Glu Gly Asn Pro Glu
    290                 295                 300

<210> SEQ ID NO 3
<211> LENGTH: 11611
<212> TYPE: DNA
<213> ORGANISM: Homo sapiens

<400> SEQUENCE: 3
ggcttcagcc ctgcagggaa agaaaagtgc aatgattctg gactgagacg cgcttgggca      60
gaggctatgt aatcgtgtct gtgttgagga cttcgcttcg aggagggaag aggagggatc     120
ggctcgctcc tccggcggcg gcggcggcgg cgactctgca ggcggagttt cgcggcggcg     180
gcaccagggt tacgccagcc ccgcggggag gtctctccat ccagcttctg cagcggcgaa     240
agccccagcg cccgagcgcc tgagccggcg gggagcaagt aaagctagac cgatctccgg     300
ggagccccgg agtaggcgag cggcggccgc cagctagttg agcgcacccc ccgcccgccc     360
cagcggcgcc gcggcgggcg gcgtccaggc ggcatggaga aggacggcct gtgccgcgct     420
gaccagcagt acgaatgcgt ggcggagatc ggggagggcg cctatgggaa ggtgttcaag     480
gcccgcgact tgaagaacgg aggccgtttc gtggcgttga gcgcgtgcg ggtgcagacc     540 ggcgaggagg gcatgccgct ctccaccatc cgcgaggtgg cggtgctgag gcacctggag     600
accttcgagc accccaacgt ggtcaggttg tttgatgtgt gcacagtgtc acgaacagac     660
agagaaacca aactaacttt agtgtttgaa catgtcgatc aagacttgac cacttacttg     720
gataaagttc agagcctgga gtgcccact gaaaccataa aggatatgat gtttcagctt     780
```

```
ctccgaggtc tggactttct tcattcacac cgagtagtgc atcgcgatct aaaaccacag      840
aacattctgg tgaccagcag cggacaaata aaactcgctg acttcggcct tgcccgcatc      900
tatagtttcc agatggctct aacctcagtg gtcgtcacgc tgtggtacag agcacccgaa      960
gtcttgctcc agtccagcta cgccaccccc gtggatctct ggagtgttgg ctgcatattt     1020
gcagaaatgt ttcgtagaaa gcctcttttt cgtggaagtt cagatgttga tcaactagga     1080
aaaatcttgg acgtgattgg actcccagga gaagaagact ggcctagaga tgttgccctt     1140
cccaggcagg cttttcattc aaaatctgcc caaccaattg agaagtttgt aacagatatc     1200
gatgaactag gcaaagacct acttctgaag tgtttgacat taacccagc caaaagaata     1260 tctgcctaca gtgccctgtc tcacccatac ttccaggacc tggaaaggtg caaagaaaac     1320
ctggattccc acctgccgcc cagccagaac acctcggagc tgaatacagc ctgaggcctc     1380
agcagccgcc ttaagctgat cctgcggaga acacccttgg tggcttatgg gtcccctca     1440 gcaagcccta cagagctgtg gaggattgct atctggaggc cttccagctg ctgtcttctg     1500
gacaggctct gcttctccaa ggaaaccgcc tagtttactg ttttgaaatc aatgcaagag     1560
tgattgcagc tttatgttca tttgtttgtt tgtttgtctg tttgtttcaa gaacctggaa     1620
aaattccaga agaagagaag ctgctgacca attgtgctgc catttgattt ttctaacctt     1680
gaatgctgcc agtgtggagt gggtaatcca ggcacagctg agttatgatg taatctctct     1740
gcagctgccg ggcctgattt ggtacttttg agtgtgtgtg tgcatgtgtg tgtgtgtgtg     1800
tgtgtgtgtg tgtgtatg tgagagattc tgtgatcttt taaagtgtta cttttttgtaa     1860 acgacaagaa taattcaatt ttaaagactc aaggtggtca gtaaataaca ggcatttgtt     1920
cactgaaggt gattcaccaa atagtcttc tcaaattaga aagttaaccc catgtcctca     1980
gcatttcttt tctggccaaa agcagtaaat ttgctagcag taaaagatga agttttatac     2040
acacagcaaa aaggagaaaa aattctagta tattttaaga gatgtgcatg cattctattt     2100
agtcttcaga atgctgaatt tacttgttgt aagtctattt taaccttctg tatgacatca     2160
tgctttatca tttctttggg aaaatagcct gtaagctttt tattacttgc tataggttta     2220
gggagtgtac ctcagataga ttttaaaaaa aagaatagaa agcctttatt tcctggtttg     2280
aaattccttt cttccctttt tttgttgttg ttattgttgt tgttgttgt tattttgttt     2340 ttgttttag gaatttgtca gaaactcttt cctgttttgg tttggagagt agttctctct     2400
aactagagac aggagtggcc ttgaaatttt cctcatctat tacactgtac tttctgccac     2460
acactgcctt gttggcaaag tatccatctt gtctatctcc cggcacttct gaaatatatt     2520
gctaccattg tataactaat aacagattgc ttaagctgtt cccatgcacc acctgtttgc     2580
ttgctttcaa tgaaccttc ataaattcgc agtctcagct tatggtttat ggcctcgatt     2640
ctgcaaacct aacagggtca catatgttct ctaatgcagt ccttctacct ggtgtttact     2700
tttgctaccc aaataatgag taggatcttg ttttcgtata ccccccacca tcccattgct     2760
accaactgtc accttgtgca ctccttttt atagaagata ttttcagtgt ctttacctga     2820
gggtatgtct ttagctatgt tttagggcca tacattact ctatcaaatg atcttttctc     2880 catccccag gctgtgctta tttctagtgc cttgtgctca ctcctgctct ctacagagcc     2940
agcctggcct gggcattgta aacagctttt ccttttctc ttactgtttt ctctacagtc     3000
ctttatattt cataccatct ctgccttata agtggtttag tgctcagttg gctctagtaa     3060
ccagaggaca cagaaagtat cttttggaaa gtttagccac ctgtgctttc tgactcagag     3120
```

```
tgcatgcaac agttagatca tgcaacagtt agattatgtt tagggttagg attttcaaag    3180
aatggaggtt gctgcactca gaaaataatt cagatcatgt ttatgcatta ttaagttgta    3240
ctgaattctt tgcagcttaa tgtgatatat gactatcttg aacaagagaa aaaactagga    3300
gatgtttctc ctgaagagct ttggggttg  ggaactattc ttttttaatt gctgtactac    3360
ttaacattgt tctaattcag tagcttgagg aacaggaaca ttgttttcta gagcaagata    3420
ataaaggaga tgggccatac aaatgttttc tactttcgtt gtgacaacat tgattaggtg    3480
ttgtcagtac tataaatgct tgagatataa tgaatccaca gcattcaagg tcaggtctac    3540
tcaaagtctc acatggaaaa gtgagttctg cctttccttt gatcgagggt caaaatacaa    3600
agacattttt gctagggcct acaaattgaa tttaaaaact cactgcactg attcatctga    3660 gcttttggt  tagtattcat ggctagagtg aacatagctt tagttttttgc tgttgtaaaa    3720 gtgttttcat aagttcactc aagaaaaatg cagctgttct gaactggaat ttttcagcat    3780
tctttagaat tttaaatgag tagagagctc aacttttatt cctagcatct gcttttgact    3840
catttctagg cagtgcttat gaagaaaaat taaagcacaa acattctggc attcaatcgt    3900
tggcagatta tcttctgatg acacagaatg aaagggcatc tcagcctctc tgaactttgt    3960
aaaaatctgt ccccagttct tccatcggtg tagttgttgc atttgagtga atactctctt    4020
gatttatgta ttttatgtcc agattcgcca tttctgaaat ccagatccaa cacaagcagt    4080
cttgccgtta gggcattttg aagcagatag tagagtaaga acttagtgac tacagcttat    4140
tcttctgtaa catatggttt caaacatctt tgccaaaagc taagcagtgg tgaactgaaa    4200
agggcatatt gccccaaggt tacactgaag cagctcatag caagttaaaa tattgtgaca    4260
gatttgaaat catgtttgaa tttcatagta ggaccagtac aagaatgtcc ctgctagttt    4320
ctgtttgatg tttggttctg gcggctcagg cattttggga actgttgcac agggtgcagt    4380
caaaacaacc tacatataaa aattacataa aagaaccttg tccatttagc tttcataaga    4440
aatcccatgg caaagagtaa taaaaaggac ctaatcttaa aaatacaatt tctaagcact    4500
tgtaagaacc cagtggggttg gagcctccca ctttgtccct cctttgaagt ggatgggaac    4560
tcaaggtgca agaacctgt  tttggaagaa agcttgggc  catttcagcc ccctgtattc    4620
tcatgatttt ctctcaggaa gcacacactg tgaatggcag acttttcatt tagccccagg    4680
tgacttacta aaaatagttg aaaattattc acctaagaat agaatctcag cattgtgtta    4740
aataaaaatg aaagctttag aaggcatgag atgttcctat cttaaataaa gcatgtttct    4800
tttctataga gaaatgtata gtttgactct ccagaatgta ctatccatct tgatgagaaa    4860
actcttaaat agtaccaaac attttgaact ttaaattatg tatttaaagt gagtgtttaa    4920
gaaactgtag ctgcttcttt tacaagtggt gcctattaaa gtcagtaatg gccattattg    4980
ttccattgtg gaaattaaat tatgtaagct tcctaatatc ataaacatat taaaattctt    5040 ctaaatatt  gcttttcttt taagtgacaa tttgactatt cttatgataa gcacatgaga    5100
gtgtcttaca ttttccaaaa gcaggcttta attgcatagt tgagtctagg aaaaaataat    5160
gttaaaagtg aatatgccac cataattact taattatgtt agtatagaaa ctacagaata    5220
tttaccctgg aaagaaaata ttggaatgtt attataaact cttagatatt tatataattc    5280
aaaagaatgc atgtttcaca ttgtgacaga taaagatgta tgatttctaa ggctttaaaa    5340
attattcata aaacagtggg caatagataa aggaaattct ggagaaaatg aaggtattta    5400
aagggtagtt tcaaagctat atatattttg aaggatatat tctttatgaa caaatatatt    5460
gtaaaaattt atactaaggt catctggtaa ctgtgggatt aatatggtcg aaaacaaatg    5520
```

```
ttatggagaa gctgtcccaa gcaaactaaa ttacctgtac tttttttccca tttcaaggga   5580 agaggcaacc acatgaagca atacttctta cacatgccta agaacgttca ttgaaaaaat   5640
aaatttttaa aaggcatgtg tttcctatgc caccaatact tttgaaaaat tgtgaacctt   5700
acccaaaacc atttatcatg tccattaagt atatttgggt atataattag gaagatattt   5760
acatgttcca tctccacagt ggaaaaactt attgaggcta ccaaagtgtg ccaagaaatg   5820
taagtcctta gagtaattag aaatgctgtt ttcctcaaaa gcatgagaaa ctagcatttt   5880
catttcttat ttactccctt tctatatcaa tgcaattcac aacccaattt taatacatcc   5940
ctatatctca agcatttcta tcttgtactt tttcagaaaa taaccaaaa ataatccttt   6000 ggtctctcta tcttctgacc tttgtaagca acagaaatgt aaaaacagaa ggggtccaat   6060
ttttacacgt ttttttctca agtagccttt ctggggattt ttattttctt aatgaagtgc   6120
caatcagctt ttcaaaatgt tttctatttc tcagcatttc caggaagtga taacgtttag   6180
ctaaatgagt agaagtggac ttccttcaac atattgttac cttgtctagc cttaggaaga   6240
aaacaagagc cacctgaaaa taaatacagg ctctttttcga gcatctgctg aaatactgtt   6300
acagcaattt gaagttgatg tggtaggaaa ggaaggtgac ttttcttgca aaagtctttc   6360
taaacattca cactgtccta agagatgagc tttcttgttt tattccggta tattccacaa   6420
ggtggcactt ttagagaaaa acaaatctga tgaagactaa agaggtactt ctaaaagaga   6480
tttcattcta actttatttt tctgcgcata tttaactctt tcctagcact tgttttttgg   6540
gatgattaat agtctctata atgttctgta acttcaatat tttacttgtt acctaggttc   6600
tgaacaattg tctgcaaata aattgttctt aaggatggat aatacaccca ttttgatcat   6660
ttaagtaaag aaagcctagt cattcattca gtcaagaaaa aatttttgaa gtacccagtt   6720
accttacttt tctagattaa aacaggctta gttactaaaa aggcagtcct catctgtgaa   6780
caggatagtt tcgttagaag tataaaactc ctttagtggc cccagttaaa acacacatac   6840
cctctctgct gctttcaaat tccctagcat ggtggccttt caacattgat taaattttaa   6900
aatcctaatt taaagatcag gtgagcaaaa tgagtagcac atcagtaatt cagtagacaa   6960
aacttttgtc tgaaaaattg ctgtattgaa acagagccct aaaataccaa aagaccaggt   7020
aattttaaca tttgtggaat cacaaatgta aattcataag aagctctaat taaaaaaaaa   7080
aagtctgaag tatatgagca taacaactta ggagtgtgtc tacatactta acttttgaag   7140 tttttttggca actttatata cttttttttaa atttacaagt ctacttaaag acttcttata   7200
ccccaaatga ttaagttaat tttagaggtc acctttctca cagcagtgtc acttgaaatt   7260
tagtagggaa ggatattgca gtattttttca gtttccttag cacagcacca cagaaagcag   7320
cttattcctt ttgagtggca gacactcgac ggtgcctgcc caactttcct cctgagtggc   7380
aagcagatga gtctcagtaa ttcatactga accaaaatgc cacatacact aggggcagtc   7440
agaaactggc tgagaaatcc cccgcctcat tcgcccctct gctcccagga actagagtcc   7500
agttaaagcc cctatgcgaa aggccgaatt ccaccccagg gtttgttata acagtggcca   7560
gtctgaaccc catttgctcg tgctcaaaac ttgattccca cttgaaagcc ttccgggcgc   7620
gctgcctcgt tgccccgccc ctttggcagg agagaggcag tgggcgaggc cgggctgggg   7680
ccccgcctcc cactcacctg ccggtgcctg aaattatgtg cggccccgcg ggctgctttc   7740
cgaggtcaga gtgccctgct gctgtctcag aggcatctgt tctgcaaatc ttaggaagaa   7800
aaatgtccct agtagcaaac gggtgtcttc tgtgcataaa taagtacaac acaattctcc   7860
```

```
gaaagttcgg gtaaaaagag atgcggtagc agctgccctg tgtgaagctg tctaccccgc   7920
atctctcagg cgctaagctc agttttttgtt tttgttttttg ttttttttaaa gaaaagatgt   7980
ataattgcag gaattttttt ttattttttt attttccatc attctatata tgtgatggtg   8040
aaagatatgc ctggaaaagt tttgttttga aaagtttatt ttctgcttcg tcttcagttg   8100
gcaaaagctc tcaattcttt agcttccagt ttcttttctc tcttttttctt tgttaggtaa   8160
ttaaaggtat gtaaacaaat tatctcatgt agcaggggat tttcatgttg agaggaatct   8220
tccgtgtgag ttgtttggtc acacaaataa ccctttctca attttaggag tttggattgt   8280
caaatgtagg tttttctcaa aggggcata taactacata ttgactgcca agaactatga   8340
ctgtagcact aatcagcaca catagagcca cacaattatt taatttctaa ctctctgtgg   8400
tccctagaaa aattccgttg atgtgcttag gttaaagttc tgaagatacc cgttgtaccc   8460
ttacttgaaa gtttctaatc ttaagtttta tgaaatgcaa taatatgtat cagctagcaa   8520
tatttctgtg atcaccaaca actctcagtt tgatcttaaa gtctgaataa taaaacaaat   8580
cccagcagta atacatttct taaacctcac agtgcatgat atatcttttc attctgatcc   8640
tgtgttttgca aaaatataca catgtatatc atagttcctc acttttttatt catttgttttt   8700
cctattacct gtagtaaata tattagttag tacatggaat ttatagcatc agctacccccc   8760
aggaacagca cctgacaggc gggggatttt ttttcaagtt gttctacatt tgcataaatt   8820
atttctatta ttattcatgt atgttattta tttctgaatc acactagtcc tgtgaaagta   8880
caactgaagg cagaaagtgt taggattttg catctaatgt tcattatcat ggtattgatg   8940
gacctaagaa aataaaaatt agactaagcc cccaaataag ctgcatgcat ttgtaacatg   9000
attagtagat ttgaatatat agatgtagta ttttgggtat ctaggtgttt tatcattatg   9060
taaaggaatt aaagtaaagg actttgtagt tgttttattt aaatatgcat atagtagagt   9120
gcaaaaatat agcaaaaata aaaactaaag gtagaaaagc attttagata tgccttaatt   9180
tagaaactgt gccaggtggc cctcggaata gatgccaggc agagaccagt gcctgggtgg   9240
tgcctcctct tgtctgccct catgaagaag cttccctcac gtgatgtagt gccctcgtag   9300
gtgtcatgtg gagtagtggg aacaggcagt actgttgaga ggagagcagt gtgagagttt   9360
ttctgtagaa gcagaactgt cagcttgtgc cttgaggctt ccagaacgtg tcagatggag   9420
aagtccaagt ttccatgctt caggcaactt agctgtgtac agaagcaatc cagtgtggta   9480
ataaaagca aggattgcct gtataattta ttataaaata aaagggattt taacaaccaa   9540
caattcccaa cacctcaaaa gcttgttgca ttttttggta tttgaggttt ttatctgaag   9600
gttaaagggc aagtgtttgg tatagaagag cagtatgtgt taagaaaaga aaaatattgg   9660
ttcacgtaga gtgcaaatta gaactagaaa gttttatacg attatcatttt tgagatgtgt   9720
taaagtaggt tttcactgta aaatgtatta gtgtttctgc attgccatag ggcctggtta   9780
aaactttctc ttaggtttca ggaagactgt cacatacagt aagcttttt ccttctgact   9840
tataatagaa aatgttttga aagtaaaaaa aaaaatcta atttggaaat ttgacttgtt   9900
agtttctgtg tttgaaatca tggttctaga aatgtagaaa ttgtgtatat cagatactca   9960
tctaggctgt gtgaaccagc ccaagatgac caacatcccc acacctctac atctctgtcc  10020
cctgtatctc ttcctttcta ccactaaagt gttccctgct accatcctgg cttgtccaca  10080
tggtgctctc catcttcctc cacatcatgg accacaggtg tgcctgtcta ggcctggcca  10140
ccactcccaa cttgacctag ccacattcat ctagagatgg ttcctgatgc tgggcacaga  10200
ctgtgctcat ggcacccatt agaaatgcct ctagcatctt tgtatgcatc ttgattttta  10260
```

```
aaccaagtca ttgtacagag cattcagttt tggctgtggt accaagagaa aaactaatca    10320
agaatataaa ccacattcca ggctgctgtt ttctctccat ctacaggcca cacttttact    10380
gtatttcttc atacttgaaa ttcattctgc tattttcata tcagggtaca gacttataag    10440
ggtgcatgtt ccttaaaggt gcataattat tcttattccg tttgcttata ttgctacaga    10500
atgctctgtt ttggtgcttt gagttctgca gacccaagaa gcagtgtgga aattcactgc    10560
ctgggacaca gtcttataag aatgttggca ggtgactttg tatcagatgt tgcttctctt    10620
ttctctgtac acagattgag agttaccaca gtggcctgtc gggtccaccc tgtgggtgca    10680
gcacagctct ctgaaagcaa gaaccttcct acctattcta acgttttgc cctctaagaa     10740 aaatggcctc aggtatggta tagacatagc aagaggggaa gggctgtctc actctagcaa    10800
ccatccctcc attacacaca gaaagccctc ttgaagcaaa agaagaagaa agaaagaaag    10860
cttatctcta aggctactgt cttcagaatg ctctgagctg aatgctcttg ctcctttccc    10920
aagaggcaga tgaaaatata gccagtttat ctataccctt cctatctgag gaggagaata    10980
gaaaagtagg gtaaatatgt aacgtaaaat atgtcattca aggaccacca aaactttaag    11040
taccctatca ttaaaaatct ggttttaaaa gtagctcaag taagggatgc tttgtgaccc    11100
agggtttctg aagtcagata gccattctta cctgcccctt actctgactt attgggaaag    11160
ggagaactgc agtggtgttt ctgttgcagt ggcaaaggta acatgtcaga aaattcagag    11220
ggttgcatac caataatcct ttggaaactg gatgtcttac tgggtgctag aatgaaaatg    11280
taggtattta ttgtcagatg atgaagttca ttgtttttttt caaaattggt gttgaaatat    11340
cactgtccaa tgtgttcact tatgtgaaag ctaaattgaa tgaggcaaaa agagcaaata    11400
gtttgtatat ttgtaatacc ttttgtattt cttacaataa aaatattggt agcaaataaa    11460
aataataaaa acaataactt taaactgctt tctggagatg aattactctc ctggctattt    11520
tcttttttac tttaatgtaa aatgagtata actgtagtga gtaaaattca ttaaattcca    11580
agttttagca gaaaaaaaaa aaaaaaaaaa a                                    11611
```

<210> SEQ ID NO 4
<211> LENGTH: 326
<212> TYPE: PRT
<213> ORGANISM: Homo sapiens

<400> SEQUENCE: 4

```
Met Glu Lys Asp Gly Leu Cys Arg Ala Asp Gln Gln Tyr Glu Cys Val
 1               5                  10                  15

Ala Glu Ile Gly Glu Gly Ala Tyr Gly Lys Val Phe Lys Ala Arg Asp
                20                  25                  30

Leu Lys Asn Gly Gly Arg Phe Val Ala Leu Lys Arg Val Arg Val Gln
            35                  40                  45

Thr Gly Glu Glu Gly Met Pro Leu Ser Thr Ile Arg Glu Val Ala Val
        50                  55                  60

Leu Arg His Leu Glu Thr Phe Glu His Pro Asn Val Val Arg Leu Phe
    65                  70                  75                  80

Asp Val Cys Thr Val Ser Arg Thr Asp Arg Glu Thr Lys Leu Thr Leu
                85                  90                  95

Val Phe Glu His Val Asp Gln Asp Leu Thr Thr Tyr Leu Asp Lys Val
                100                 105                 110

Pro Glu Pro Gly Val Pro Thr Glu Thr Ile Lys Asp Met Met Phe Gln
            115                 120                 125
```

Leu Leu Arg Gly Leu Asp Phe Leu His Ser His Arg Val Val His Arg
130                 135                 140

Asp Leu Lys Pro Gln Asn Ile Leu Val Thr Ser Ser Gly Gln Ile Lys
145                 150                 155                 160

Leu Ala Asp Phe Gly Leu Ala Arg Ile Tyr Ser Phe Gln Met Ala Leu
                165                 170                 175

Thr Ser Val Val Val Thr Leu Trp Tyr Arg Ala Pro Glu Val Leu Leu
            180                 185                 190

Gln Ser Ser Tyr Ala Thr Pro Val Asp Leu Trp Ser Val Gly Cys Ile
        195                 200                 205

Phe Ala Glu Met Phe Arg Arg Lys Pro Leu Phe Arg Gly Ser Ser Asp
    210                 215                 220

Val Asp Gln Leu Gly Lys Ile Leu Asp Val Ile Gly Leu Pro Gly Glu
225                 230                 235                 240

Glu Asp Trp Pro Arg Asp Val Ala Leu Pro Arg Gln Ala Phe His Ser
                245                 250                 255

Lys Ser Ala Gln Pro Ile Glu Lys Phe Val Thr Asp Ile Asp Glu Leu
            260                 265                 270

Gly Lys Asp Leu Leu Leu Lys Cys Leu Thr Phe Asn Pro Ala Lys Arg
        275                 280                 285

Ile Ser Ala Tyr Ser Ala Leu Ser His Pro Tyr Phe Gln Asp Leu Glu
    290                 295                 300

Arg Cys Lys Glu Asn Leu Asp Ser His Leu Pro Pro Ser Gln Asn Thr
305                 310                 315                 320

Ser Glu Leu Asn Thr Ala
                325

<210> SEQ ID NO 5
<211> LENGTH: 57
<212> TYPE: DNA
<213> ORGANISM: Artificial Sequence
<220> FEATURE:
<223> OTHER INFORMATION: A synthetic oligonucleotide

<400> SEQUENCE: 5
ccggacagtt cgtgaggtgg ctttactcga gtaaagccac ctcacgaact gttttt      57

<210> SEQ ID NO 6
<211> LENGTH: 58
<212> TYPE: DNA
<213> ORGANISM: Artificial Sequence
<220> FEATURE:
<223> OTHER INFORMATION: A synthetic oligonucleotide

<400> SEQUENCE: 6
ccgggacctg gaaaggtgca agaactcga gttctttgca cctttccagg tcttttg      58

<210> SEQ ID NO 7
<211> LENGTH: 9
<212> TYPE: RNA
<213> ORGANISM: Artificial Sequence
<220> FEATURE:
<223> OTHER INFORMATION: A synthetic oligonucleotide

<400> SEQUENCE: 7 uucaagaga      9